(12) United States Patent
De Peretti et al.

(10) Patent No.: US 8,598,166 B2
(45) Date of Patent: Dec. 3, 2013

(54) POLYSUBSTITUTED DERIVATIVES OF 6-HETEROARYLIMIDAZO[1,2-A]PYRIDINES, AND PREPARATION AND THERAPEUTIC USE THEREOF

(75) Inventors: Danielle De Peretti, Antony (FR); Yannick Evanno, Dannemois (FR); David Machnik, Paris (FR); Nathalie Rakotoarisoa, Longjumeau (FR)

(73) Assignee: Sanofi, Paris (FR)

( * ) Notice: Subject to any disclaimer, the term of this patent is extended or adjusted under 35 U.S.C. 154(b) by 114 days.

(21) Appl. No.: 13/291,660

(22) Filed: Nov. 8, 2011

(65) Prior Publication Data

US 2012/0053202 A1    Mar. 1, 2012

Related U.S. Application Data

(63) Continuation of application No. 12/881,820, filed on Sep. 14, 2010, now Pat. No. 8,088,765, which is a continuation of application No. PCT/FR2009/000298, filed on Mar. 20, 2009.

(30) Foreign Application Priority Data

Mar. 21, 2008  (FR) ..................... 08 01585

(51) Int. Cl.
*A61K 31/535* (2006.01)
*A01N 43/42* (2006.01)
*A61K 31/44* (2006.01)

(52) U.S. Cl.
USPC ..................... 514/233.2; 514/300

(58) Field of Classification Search
USPC .............................. 514/233.2, 300
See application file for complete search history.

(56) References Cited

U.S. PATENT DOCUMENTS

| | | | |
|---|---|---|---|
| 7,902,219 B2 | 3/2011 | Peyronel et al. | |
| 2009/0253735 A1 | 10/2009 | Almario-Garcia et al. | |
| 2010/0168155 A1 | 7/2010 | El-Ahmad et al. | |
| 2011/0065699 A1 | 3/2011 | De Peretti et al. | |
| 2011/0065727 A1 | 3/2011 | De Peretti et al. | |
| 2011/0065745 A1 | 3/2011 | De Peretti et al. | |

FOREIGN PATENT DOCUMENTS

| | | |
|---|---|---|
| FR | 2 903 105 | 1/2006 |
| FR | 2 903 107 | 1/2008 |
| WO | WO 2004/076412 A2 | 9/2004 |
| WO | WO 2008/034974 A1 | 3/2008 |
| WO | WO 2008/104077 | 9/2008 |

OTHER PUBLICATIONS (Jankovic et al., Progress in Neurobiology, vol. 77 (2005), pp. 128-138.*
International Search Report for WO2009/114392 dated Dec. 3, 2009.
Gudmundsson et al, An Improved Synthesis of 2-Chlorinated Imidazo[1,2-a]pyridines and the Application of this Proceedure for the Synthesis of Several New Polychlorinated Imidazo[1,2-a]pyridines, Syn. Comm., 1997(27) 10, pp. 1763-1775.
Barder et al, Catalysts for Suzuki-Miyaura Coupling Processes: Scope and Studies of the Effect of Ligand Structure, JACS, 2005(127) pp. 4685-4696.
Cai et al, Synthesis and Structure-Affinity Relationship of New 4-(6-Iodo-H-Imidazo[1,2-a] pyridin-2-yl)-N-dimethylbenzeneamine Derivatives as Ligands for Human b-Amyloid plaques, J. Med. Chem., 2007(50) pp. 4746-4758.
DiMauro et al, Microwave-Assisted Preparation of Fused Bicyclic Heteroaryl Bororiates: Application in One-Pot Suzuki Couplings, JOC, 2006(71) pp. 3959-5962.
Enguehard et al, (Hetero)Arylation of 6-Halogenoimidazo [1,2-a]Pyridines Differently Substituted at C(2): Influence of the 2-Substituent on the Suzuki Cross-Coupling Reaction, Helvetica Chimica Acta, 2001(84) pp. 3610-3615.
FIsher et al, Imidazo[1,2-a]pyridine Anthelmintic and Antifungal Agents, J.Med.Chem., 1972 (15) 9, p. 982-985.

* cited by examiner

*Primary Examiner* — Niloofar Rahmani
(74) *Attorney, Agent, or Firm* — Kelly L. Bender

(57) ABSTRACT

Compounds of formula (I):

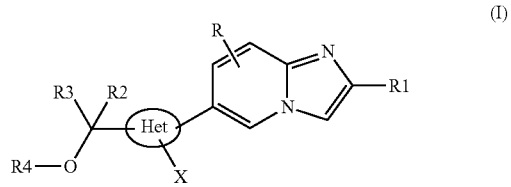

wherein $R_1$, $R_2$, $R_3$, $R_4$, Het and X are as defined in the disclosure, or an acid addition salt thereof, and the therapeutic use and process of synthesis thereof.

9 Claims, No Drawings

POLYSUBSTITUTED DERIVATIVES OF 6-HETEROARYLIMIDAZO[1,2-A]PYRIDINES, AND PREPARATION AND THERAPEUTIC USE THEREOF

This application is a continuation U.S. patent application Ser. No. 12/881,820, filed Sep. 14, 2010, now allowed, which is a continuation of International Application No. PCT/FR2009/000298, filed Mar. 20, 2009, which are incorporated herein by reference in their entirety; and which claims the benefit of priority of French Patent Application No. 0801585, filed Mar. 21, 2008.

The present invention relates to polysubstituted 6-heteroarylimidazo[1,2-a]pyridine derivatives, to the preparation thereof and to the therapeutic use thereof in the treatment or prevention of diseases involving Nurr-1 nuclear receptors, also known as NR4A2, NOT, TINUR, RN-1 and HZF3.

The subject of the present invention is the compounds of formula (I):

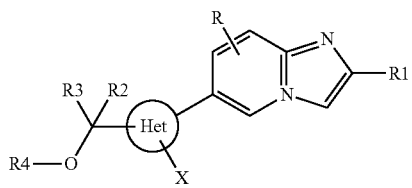

in which:

$R_1$ represents:
a phenyl or naphthyl group, a heteroaryl group or a heterocyclic group, it being possible for these groups to be optionally substituted with one or more atoms or groups chosen, independently of one another, from the following atoms or groups: halogen, $(C_1-C_{10})$alkyl, halo$(C_1-C_{10})$alkyl, $(C_1-C_{10})$alkoxy, halo$(C_1-C_{10})$alkoxy, $(C_1-C_{10})$thioalkyl, —S(O)$(C_1-C_{10})$alkyl, —S(O)$_2$$(C_1-C_{10})$alkyl), hydroxyl, oxo, cyano, nitro, hydroxy$(C_1-C_{10})$alkylene, NRaRb$(C_1-C_{10})$alkylene, $(C_1-C_{10})$alkoxy$(C_1-C_{10})$alkyleneoxy, NRaRb, CONRaRb, SO$_2$NRaRb, NRcCORd, OC(O)NRaRb, OCO$(C_1-C_{10})$alkyl, NRcC(O)Ore, NRcSO$_2$Re, aryl$(C_1-C_{10})$alkylene, monocyclic heteroaryl or aryl, the monocyclic heteroaryl or aryl being optionally substituted with one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, oxo, nitro, cyano or OCO$(C_1-C_{10})$alkyl group, and $R_1$ is linked to the imidazo[1,2-a]pyridine by an aromatic carbon;

Het represents a monocyclic heteroaryl group containing from 5 to 6 atoms, including from 1 to 3 heteroatoms chosen from N, O and S;

X represents from 1 to 3 substituents, which are identical to or different from one another, chosen from a hydrogen, a halogen, $(C_1-C_{10})$alkyl, $(C_1-C_{10})$alkoxy, NRaRb, nitro and cyano, it being possible for the $(C_1-C_{10})$alkyl to be optionally substituted with one or more groups chosen from a halogen, $(C_1-C_{10})$alkoxy, $(C_1-C_{10})$haloalkoxy, NRaRb or hydroxyl;

R represents, at position 3, 5, 7 or 8 of the imidazo[1,2-a]pyridine, from 1 to 4 substituents, which are identical to or different from one another, chosen from a hydrogen, a halogen, $(C_1-C_{10})$alkyl, halo$(C_1-C_{10})$alkyl and $(C_1-C_{10})$alkoxy;

$R_2$ and $R_3$ represent, independently of one another,
a hydrogen atom,
a $(C_1-C_{10})$alkyl group, optionally substituted with an Rf group;
an aryl group, optionally substituted with one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;

$R_4$ represents:
a hydrogen atom,
a $(C_1-C_{10})$alkyl group, optionally substituted with an Rf group;
an aryl group, optionally substituted with one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano, $(C_1-C_{10})$alkyl(CO)—, CONRaRb, NRcCORd, OC(O)NRaRb, OCO$(C_1-C_{10})$alkyl, NRcC(O)ORe or aryl group, the aryl being optionally substituted with one or more substituents chosen from a halogen and a $(C_1-C_{10})$alkyl halo$(C_1-C_{10})$, alkyl, $(C_1-C_{10})$alkoxy, halo$(C_1-C_{10})$alkoxy, NRaRb, hydroxyl, nitro or cyano group;

Ra and Rb represent, independently of one another, a hydrogen atom or a $(C_1-C_{10})$alkyl, aryl$(C_1-C_{10})$alkylene or aryl group;

or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1-C_{10})$alkyl, aryl or aryl$(C_1-C_{10})$alkylene group;

Rc and Rd represent, independently of one another, a hydrogen atom or a $(C_1-C_{10})$alkyl, aryl$(C_1-C_{10})$alkylene or aryl group;

or Rc and Rd together form a $(C_2-C_5)$alkylene group;

Re represents a $(C_1-C_{10})$alkyl, aryl$(C_1-C_{10})$alkylene or aryl group;

or Rc and Re together form a $(C_2-C_5)$alkylene group;

Rf represents a halogen atom or a $(C_1-C_{10})$alkoxy, halo$(C_1-C_{10})$alkoxy, hydroxyl, cyano, NRaRb, C(O)NRaRb, NRcCORd, OC(O)NRaRb, OCO$(C_1-C_{10})$alkyl, NRcCOORe, SO$_2$NRaRb, NRcSO$_2$Re, aryl$(C_1-C_{10})$alkylene or aryl group, the aryl being optionally substituted with one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano or OCO$(C_1-C_{10})$alkyl group;

in the form of a base or of an addition salt with an acid.

The compounds of formula (I) may comprise one or more asymmetrical carbon atoms. They may therefore exist in the form of enantiomers or of diastereoisomers. These enantiomers and diastereoisomers, and also mixtures thereof, including racemic mixtures, are part of the invention.

The compounds of formula (I) may exist in the form of bases or of addition salts with acids. Such addition salts are part of the invention.

The salts may be prepared with pharmaceutically acceptable acids, but the salts of other acids that are useful, for example, for purifying or isolating the compounds of formula (I) are also part of the invention.

The compounds of formula (I) may also exist in the form of hydrates or of solvates, i.e. in the form of associations or of combinations with one or more molecules of water or with a solvent. Such hydrates and solvates are also part of the invention.

In the context of the present invention:
the term "a $(C_x-C_t)$ group" is intended to mean: a group comprising between x and t carbon atoms;
the term "a halogen atom" is intended to mean: a fluorine, a chlorine, a bromine or an iodine;

the term "an alkyl group" is intended to mean: a linear, branched or cyclic, saturated aliphatic group, optionally substituted with a linear, branched or cyclic, saturated alkyl group. By way of examples, mention may be made of methyl, ethyl, propyl, isopropyl, butyl, isobutyl, tert-butyl, cyclopropyl, cyclobutyl, cyclopentyl, cyclohexyl, methylcyclopropyl, cyclopropylmethyl, etc. groups;

the term "an alkylene group" is intended to mean: a divalent alkyl group;

the term "an alkoxy group" is intended to mean: an —O— alkyl radical where the alkyl group is as defined above;

the term "a haloalkyl group" is intended to mean: an alkyl group substituted with one or more halogen atoms which are identical or different. By way of examples, mention may be made of $CF_3$, $CH_2CF_3$, $CHF_2$ or $CCl_3$ groups;

the term "a haloalkoxy group" is intended to mean: an —O— alkyl radical where the alkyl group is as defined above and substituted with one or more halogen atoms, which are identical or different. By way of examples, mention may be made of $OCF_3$, $OCHF_2$ or $OCCl_3$ groups;

the term "a thioalkyl group" is intended to mean: an S-alkyl group where the alkyl group is as defined above;

the term "an aryl group" is intended to mean: a monocyclic or bicyclic aromatic group containing from 6 to 10 atoms. By way of examples of an aryl group, mention may be made of phenyl and naphthyl groups;

the term "a heteroaryl group" is intended to mean: a monocyclic or bicyclic aromatic group containing from 5 to 10 atoms, including from 1 to 4 heteroatoms chosen from N, O and S. By way of examples of heteroaryl groups, mention may be made of: pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine, triazine, thienothiophene, furofuran, thienofuran, furopyrrole, thienopyrrole, pyrrolopyrrole, pyrroloisoxazole, furoisoxazole, thienoisoxazole, isoxazoloisoxazole, pyrrolooxazole, furooxazole, thienooxazole, oxazoloisoxazole, oxazolooxazole, pyrroloisothiazole, furoisothiazole, thienoisothiazole, isothiazoloisoxazole, isothiazolooxazole, isothiazolo-isothiazole, pyrrolothiazole, furothiazole, thienothiazole, thiazolooxazole, thiazolo-isoxazole, thiazoloisothiazole, thiazolothiazole, pyrrolopyrazole, furopyrazole, thienopyrazole, pyrazoloisoxazole, pyrazolooxazole, pyrazoloisothiazole, pyrazolothiazole, pyrazolopyrazole, pyrroloimidazole, furoimidazole, thienoimidazole, imidazoisoxazole, imidazooxazole, imidazoisothiazole, imidazothiazole, imidazopyrazole, imidazo-imidazole, pyrrolooxadiazole, furooxadiazole, thienooxadiazole, pyrazolooxadiazole, imidazooxadiazole, furothiadiazole, thienothiadiazole, pyrrolothiadiazole, imidazothiadiazole, pyrazolothiadiazole, thienotriazole, pyrrolotriazole, furotriazole, oxazolotriazole, isoxazolotriazole, thiazolotriazole, isothiazolotriazole, pyrazolotriazole, imidazotriazole, indole, isoindole, benzimidazole, indazole, indolizine, benzofuran, isobenzofuran, benzothiophene, benzo[c]thiophene, pyrrolopyridine, imidazopyridine, pyrazolopyridine, triazolopyridine, tetrazolopyridine, pyrrolopyrimidine, imidazopyrimidine, pyrazolopyrimidine, triazolopyrimidine, pyrrolopyrazine, imidazopyrazine, pyrazolopyrazine, triazolopyrazine, pyrrolopyridazine, imidazopyridazine, pyrazolopyridazine, triazolopyridazine, pyrrolotriazine, imidazotriazine, pyrazolotriazine, furopyridine, furopyrimidine, furopyrazine, furopyridazine, furotriazine, oxazolopyridine, oxazolopyrimidine, oxazolopyrazine, oxazolopyridazine, isoxazolopyridine, isoxazolopyrimidine, isoxazolopyrazine, isoxazolopyridazine, oxadiazolopyridine, benzoxazole, benzisoxazole, benzoxadiazole, thienopyridine, thienopyrimidine, thienopyrazine, thienopyridazine, thienotriazine, thiazolopyridine, thiazolopyrimidine, thiazolopyrazine, thiazolopyridazine, isothiazolopyridine, isothiazolopyrimidine, isothiazolopyrazine, isothiazolopyridazine, thiadiazolopyridine, benzothiazole, benzoisothiazole, benzothiadiazole, benzotriazole, quinoline, isoquinoline, cinnoline, phthalazine, quinoxaline, quinazoline, naphthyridine, benzotriazine, pyridopyrimidine, pyridopyrazine, pyridopyridazine, pyridotriazine, pyrimidopyrimidine, pyrimidopyrazine, pyrimidopyridazine, pyrazinopyrazine, pyrazinopyridazine, pyridazinopyridazine.

the term "a heterocyclic group" is intended to mean: a bicyclic group containing from 9 to 10 atoms comprising from 1 to 4 heteroatoms chosen from N, O and S, one ring of which is aromatic and the other ring of which is saturated or partially saturated, each of the rings comprising at most only 2 heteroatoms. By way of examples of bicyclic groups, mention may be made of: benzodioxole, benzoxathiole, benzopyran, benzothiopyran, benzoxazine, benzothiazine, benzodioxine, benzothioxine, dioxolopyridine, oxathiolo-pyridine, pyranopyridine, thiopyranopyridine, oxazinopyridine, thiazinopyridine, dioxinopyridine, thioxinopyridine, dioxolopyrimidine, oxathiolopyrimidine, pyranopyrimidine, thiopyranopyrimidine, oxazinopyrimidine, thiazinopyrimidine, dioxinopyrimidine, thioxinopyrimidine, dioxolopyrazine, oxathiolopyrazine, pyranopyrazine, thiopyranopyrazine, oxazinopyrazine, thiazinopyrazine, dioxinopyrazine, thioxinopyrazine, dioxolopyridazine, oxathiolopyridazine, pyranopyridazine, thiopyranopyridazine, oxazinopyridazine, thiazinopyridazine, dioxinopyridazine, thioxinopyridazine, indole, isoindole, benzimidazole, indazole, indolizine, benzofuran, isobenzofuran, benzothiophene, benzo[c]thiophene, pyrrolopyridine, imidazopyridine, pyrazolopyridine, pyrrolopyrimidine, imidazopyrimidine, pyrazolopyrimidine, pyrrolopyrazine, imidazopyrazine, pyrazolopyrazine, pyrrolopyridazine, imidazopyridazine, pyrazolopyridazine, furopyridine, furopyrimidine, furopyrazine, furopyridazine, oxazolopyridine, oxazolopyrimidine, oxazolopyrazine, oxazolopyridazine, isoxazolopyridine, isoxazolopyrimidine, isoxazolopyrazine, isoxazolopyridazine, benzoxazole, benzisoxazole, benzoxadiazole, thienopyridine, thienopyrimidine, thienopyrazine, thienopyridazine, thiazolopyridine, thiazolopyrimidine, thiazolopyrazine, thiazolopyridazine, isothiazolopyridine, isothiazolopyrimidine, isothiazolopyrazine, isothiazolopyridazine, benzothiazole, benzoisothiazole, quinoline, isoquinoline, cinnoline, phthalazine, quinoxaline, quinazoline, naphthyridine, pyridopyrimidine, pyridopyrazine, pyridopyridazine, pyrimidopyrimidine, pyrimidopyrazine, pyrimidopyridazine, pyrazinopyrazine, pyrazinopyridazine, pyridazinopyridazine, one of the rings of these bicyclic groups being in saturated or partially saturated form, for example dihydrobenzofuran, tetrahydroquinoline, dihydrobenzoxazole or benzodioxole;

the sulphur and nitrogen atoms may be in the oxidized state (N-oxide, sulphoxide, sulphone).

Among the compounds of formula (I) which are subjects of the invention, a first group of compounds is constituted of the compounds for which:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, it being possible for these groups to be optionally substituted with one or more groups or atoms chosen, independently of one another, from halogen, $(C_1\text{-}C_{10})$alkyl, $(C_1\text{-}C_{10})$alkoxy, CONRaRb, NRaRb, $(C_1\text{-}C_{10})$thioalkyl, $-S(O)_2(C_1\text{-}C_{10}\text{-}$alkyl), halo$(C_1\text{-}C_{10})$alkyl, hydroxy$(C_1\text{-}C_{10})$alkylene, NRaRb $(C_1\text{-}C_{10})$alkylene, NRcCORd, SO$_2$NRaRb, cyano and nitro;

Ra and Rb represent, independently of one another, a hydrogen atom or a $(C_1\text{-}C_{10})$alkyl group;

or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1\text{-}C_{10})$alkyl, aryl or aryl$(C_1\text{-}C_{10})$alkylene group;

Rc and Rd represent, independently of one another, a hydrogen atom or a $(C_1\text{-}C_{10})$alkyl group;

the other substituents being as defined above.

Among the compounds of formula (I) which are subjects of the invention, a second group of compounds is constituted of the compounds for which:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, it being possible for these groups to be optionally substituted with one or more groups or atoms chosen, independently of one another, from halogen, $(C_1\text{-}C_{10})$alkyl, $(C_1\text{-}C_{10})$alkoxy, CONRaRb, NRaRb, $(C_1\text{-}C_{10})$thioalkyl, $-S(O)_2(C_1\text{-}C_{10}\text{-}$alkyl), halo$(C_1\text{-}C_{10})$alkyl, hydroxy$(C_1\text{-}C_{10})$alkylene, NRaRb $(C_1\text{-}C_{10})$alkylene, NRcCORd, SO$_2$NRaRb, cyano and nitro;

Ra and Rb represent, independently of one another, a hydrogen atom or a $(C_1\text{-}C_{10})$alkyl group;

Rc and Rd represent, independently of one another, a hydrogen atom or a $(C_1\text{-}C_{10})$alkyl group;

the other substituents being as defined above.

Among the compounds of formula (I) which are subjects of the invention, a third group of compounds is constituted of the compounds for which:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, it being possible for these groups to be optionally substituted with one or more atoms or groups chosen, independently of one another, from halogen, methyl, methoxy, hydroxymethyl, CON(CH$_3$)$_2$, morpholinyl, pyrrolidinylethyl, NHCO—CH (CH$_3$)$_2$, CH$_2$N(CH$_3$)$_2$, NH$_2$, CONHCH(CH$_3$)$_2$, pyrrolidinyl, methylsulphonyl, trifluoromethyl, methylthio, cyano, nitro, —NHCO(CH$_3$), CONH(CH$_3$), CONHC(CH$_3$)$_3$, —SO$_2$N(CH$_3$)$_2$ and isopentyl;

the other substituents being as defined above.

Among the compounds of formula (I) which are subjects of the invention, a fourth group of compounds is constituted of the compounds for which:

Het represents a furyl, thienyl, pyridinyl, thiazolyl, pyrazolyl or imidazolyl group; the other substituents being as defined above.

Among the compounds of formula (I) which are subjects of the invention, a fifth group of compounds is constituted of the compounds for which:

X represents from 1 to 3 substituents, which are identical to or different from one another, chosen from a hydrogen, a halogen and $(C_1\text{-}C_{10})$alkyl groups;

the other substituents being as defined above.

Among the compounds of formula (I) which are subjects of the invention, a sixth group of compounds is constituted of the compounds for which:

X represents from 1 to 3 substituents, which are identical to or different from one another, chosen from a hydrogen, a fluorine and a methyl group;

the other substituents being as defined above.

Among the compounds of formula (I) which are subjects of the invention, a seventh group of compounds is constituted of the compounds for which:

R represents, at position 3, 5, 7 or 8 of the imidazo[1,2-a]pyridine, from 1 to 4 substituents, which are identical to or different from one another, chosen from a hydrogen and $(C_1\text{-}C_{10})$alkyl;

the other substituents being as defined above.

Among the compounds of formula (I) which are subjects of the invention, an eighth group of compounds is constituted of the compounds for which:

R represents, at position 3, 5, 7 or 8 of the imidazo[1,2-a]pyridine, from 1 to 4 hydrogen atoms, or 1 methyl group;

the other substituents being as defined above.

Among the compounds of formula (I) which are subjects of the invention, a ninth group of compounds is constituted of the compounds for which:

R represents, at position 3 of the imidazo[1,2-a]pyridine, 1 hydrogen atom or 1 methyl group;

the other substituents being as defined above.

Among the compounds of formula (I) which are subjects of the invention, a tenth group of compounds is constituted of the compounds for which:

$R_2$ and $R_3$ represent, independently of one another, a hydrogen atom or a $(C_1\text{-}C_{10})$alkyl group;

the other substituents being as defined above.

Among the compounds of formula (I) which are subjects of the invention, an eleventh group of compounds is constituted of the compounds for which:

$R_2$ and $R_3$ represent, independently of one another, a hydrogen atom or a methyl group; the other substituents being as defined above.

Among the compounds of formula (I) which are subjects of the invention, a twelfth group of compounds is constituted of the compounds for which:

$R_4$ represents: a hydrogen atom or a $(C_1\text{-}C_{10})$alkyl group;

the other substituents being as defined above.

Among the compounds of formula (I) which are subjects of the invention, a thirteenth group of compounds is constituted of the compounds for which:

$R_4$ represents: a hydrogen atom or a methyl group;

the other substituents being as defined above.

Among the compounds of formula (I) which are subjects of the invention, a fourteenth group of compounds is constituted of the compounds for which:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, it being possible for these groups to be optionally substituted with one or more atoms or groups chosen, independently of one another, from halogen, $(C_1\text{-}C_{10})$alkyl, $(C_1\text{-}C_{10})$alkoxy, —CONRaRb, —NRaRb, $(C_1\text{-}C_{10})$thio alkyl, —S(O)$_2$(C$_1$-C$_{10}$-alkyl), halo$(C_1\text{-}C_{10})$alkyl, hydroxy$(C_1\text{-}C_{10})$alkylene, NRaRb$(C_1\text{-}C_{10})$alkylene, NRcCORd, SO$_2$NRaRb, cyano and nitro;

Ra and Rb represent, independently of one another, a hydrogen atom or a $(C_1-C_{10})$alkyl group;

or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1-C_{10})$alkyl, aryl or aryl$(C_1-C_{10})$alkylene group;

Rc and Rd represent, independently of one another, a hydrogen atom or a $(C_1-C_{10})$alkyl group;

Het represents a furyl, thienyl, pyridinyl, thiazolyl, pyrazolyl or imidazolyl group;

X represents from 1 to 3 substituents, which are identical to or different from one another, chosen from a hydrogen, a halogen and $(C_1-C_{10})$alkyl groups;

R represents, at position 3, 5, 7 or 8 of the imidazo[1,2-a]pyridine, from 1 to 4 substituents, which are identical to or different from one another, chosen from a hydrogen, a halogen and $(C_1-C_{10})$alkyl;

$R_2$ and $R_3$ represent, independently of one another, a hydrogen atom or a $(C_1-C_{10})$alkyl group;

$R_4$ represents: a hydrogen atom or a $(C_1-C_{10})$alkyl group;

in the form of a base or of an addition salt with an acid.

Among the compounds of formula (I) which are subjects of the invention, a fifteenth group of compounds is constituted of the compounds for which:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, it being possible for these groups to be optionally substituted with one or more groups or atoms chosen, independently of one another, from halogen, $(C_1-C_{10})$alkyl, $(C_1-C_{10})$alkoxy, CONRaRb, NRaRb, $(C_1-C_{10})$thioalkyl, —S(O)$_2$($C_1-C_{10}$-alkyl), halo$(C_1-C_{10})$alkyl, hydroxy$(C_1-C_{10})$alkylene, NRaRb $(C_1-C_{10})$alkylene, NRcCORd, SO$_2$NRaRb, cyano and nitro;

Ra and Rb represent, independently of one another, a hydrogen atom or a $(C_1-C_{10})$alkyl group;

Rc and Rd represent, independently of one another, a hydrogen atom or a $(C_1-C_{10})$alkyl group;

Het represents a furyl, thienyl, pyridinyl, thiazolyl, pyrazolyl or imidazolyl group;

X represents from 1 to 3 substituents, which are identical to or different from one another, chosen from a hydrogen, a halogen and $(C_1-C_{10})$alkyl groups;

R represents, at position 3, 5, 7 or 8 of the imidazo[1,2-a]pyridine, from 1 to 4 substituents, which are identical to or different from one another, chosen from a hydrogen, a halogen and $(C_1-C_{10})$alkyl;

$R_2$ and $R_3$ represent, independently of one another, a hydrogen atom or a $(C_1-C_{10})$alkyl group;

$R_4$ represents: a hydrogen atom or a $(C_1-C_{10})$alkyl group;

in the form of a base or of addition salt with an acid.

Among the compounds of formula (I) which are subjects of the invention, a sixteenth group of compounds is constituted of the compounds for which:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, it being possible for these groups to be optionally substituted with one or more atoms or groups chosen, independently of one another, from halogen, methyl, methoxy, hydroxymethyl, —CON(CH$_3$)$_2$, morpholinyl, pyrrolidinylethyl, —NHCO—CH(CH$_3$)$_2$, —CH$_2$N(CH$_3$)$_2$, —NH$_2$, —CONHCH(CH$_3$)$_2$, pyrrolidinyl, methylsulphonyl, trifluoromethyl, methylthio, cyano, nitro, —NHCO(CH$_3$), CONH(CH$_3$), CONHC(CH$_3$)$_3$, —SO$_2$N(CH$_3$)$_2$ and isopentyl;

Het represents a furyl, thienyl, pyridinyl, thiazolyl, pyrazolyl or imidazolyl group;

X represents from 1 to 3 substituents, which are identical to or different from one another, chosen from a hydrogen, a fluorine and a methyl group;

R represents, at position 3, 5, 7 or 8 of the imidazo[1,2-a]pyridine, from 1 to 4 hydrogen atoms or methyl groups;

$R_2$ and $R_3$ represent, independently of one another, a hydrogen atom or a methyl group;

$R_4$ represents: a hydrogen atom or a methyl group;

in the form of a base or of an addition salt with an acid.

Among the compounds of formula (I) which are subjects of the invention, a seventeenth group of compounds is constituted of the compounds for which:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, it being possible for these groups to be optionally substituted with one or more atoms or groups chosen, independently of one another, from halogen, methyl, methoxy, hydroxymethyl, —CON(CH$_3$)$_2$, morpholinyl, pyrrolidinylethyl, —NHCO—CH(CH$_3$)$_2$, —CH$_2$N(CH$_3$)$_2$, —NH$_2$, —CONHCH(CH$_3$)$_2$, pyrrolidinyl, methylsulphonyl, trifluoromethyl, methylthio, cyano, nitro, —NHCO(CH$_3$), CONH(CH$_3$), CONHC(CH$_3$)$_3$, —SO$_2$N(CH$_3$)$_2$ and isopentyl;

Het represents a furyl, thienyl, pyridinyl, thiazolyl, pyrazolyl or imidazolyl group;

X represents from 1 to 3 substituents, which are identical to or different from one another, chosen from a hydrogen, a fluorine and a methyl group;

R represents, at position 3, 5, 7 or 8 of the imidazo[1,2-a]pyridine, from 1 to 4 hydrogen atoms, or 1 methyl group;

$R_2$ and $R_3$ represent, independently of one another, a hydrogen atom or a methyl group;

$R_4$ represents: a hydrogen atom or a methyl group;

in the form of a base or of an addition salt with an acid.

Among the compounds of formula (I) which are subjects of the invention, an eighteenth group of compounds is constituted of the compounds for which:

$R_1$ represents a phenyl, furyl or quinolinyl group, it being possible for these groups to be optionally substituted with one or more atoms or groups chosen, independently of one another, from halogen and $(C_1-C_{10})$alkyl;

Het represents a furyl group, a thienyl group, a pyridinyl group or a thiazolyl group;

X represents a hydrogen;

R is a hydrogen;

$R_2$ and $R_3$ represent, independently of one another, a hydrogen atom;

$R_4$ represents a hydrogen atom, in the form of a base or of an addition salt with an acid.

Among the compounds of formula (I) which are subjects of the invention, mention may in particular be made of the following compounds:

{5-[2-(4-Chlorophenyl)imidazo[1,2-a]pyridin-6-yl]furan-2-yl}methanol;

{4-[2-(4-Chlorophenyl)imidazo[1,2-a]pyridin-6-yl]thien-2-yl}methanol;

{5-[2-(4-Chlorophenyl)imidazo[1,2-a]pyridin-6-yl]thien-2-yl}methanol;

{2-[2-(4-Chlorophenyl)imidazo[1,2-a]pyridin-6-yl]pyridin-4-yl}methanol;

{5-[2-(4-Chlorophenyl)imidazo[1,2-a]pyridin-6-yl]pyridin-3-yl}methanol;

{4-[2-(4-Chlorophenyl)imidazo[1,2-a]pyridin-6-yl]furan-2-yl}methanol;

{6-[2-(4-Chlorophenyl)imidazo[1,2-a]pyridin-6-yl]pyridin-2-yl}methanol;

{5-[2-(4-Chlorophenyl)imidazo[1,2-a]pyridin-6-yl]thien-3-yl}methanol;

{2-[2-(4-Chlorophenyl)imidazo[1,2-a]pyridin-6-yl]thiazol-5-yl}methanol;

{2-[2-(4-Chlorophenyl)imidazo[1,2-a]pyridin-6-yl]thiazol-4-yl}methanol;

{4-[2-(4-Chlorophenyl)imidazo[1,2-a]pyridin-6-yl]thiazol-2-yl}methanol;

[2-(2-Furan-3-ylimidazo[1,2-a]pyridin-6-yl)pyridin-4-yl]methanol and the hydrochloride thereof;

[5-(2-Quinolin-3-ylimidazo[1,2-a]pyridin-6-yl)furan-2-yl]methanol and the hydrochloride thereof;

[4-(2-p-Tolylimidazo[1,2-a]pyridin-6-yl)thien-2-yl]methanol;

[2-(2-Quinolin-3-ylimidazo[1,2-a]pyridin-6-yl)pyridin-4-yl]methanol and the hydrochloride thereof;

[4-(2-Quinolin-3-ylimidazo[1,2-a]pyridin-6-yl)thien-2-yl]methanol and the hydrochloride thereof;

{4-[2-(1H-Indol-5-yl)imidazo[1,2-a]pyridin-6-yl]thien-2-yl}methanol;

{5-[2-(1H-Indol-5-yl)imidazo[1,2-a]pyridin-6-yl]furan-2-yl}methanol and the hydrochloride thereof;

[4-(2-Phenylimidazo[1,2-a]pyridin-6-yl)thien-2-yl]methanol and the hydrochloride thereof;

{4-[2-(1H-Pyrrolo[2,3-i]pyridin-5-yl)imidazo[1,2-a]pyridin-6-yl]thien-2-yl}methanol and the hydrochloride thereof;

{4-[2-(3-Methoxyphenyl)imidazo[1,2-a]pyridin-6-yl]thien-2-yl}methanol and the hydrochloride thereof;

{2-[2-(1H-Pyrrolo[2,3-i]pyridin-5-yl)imidazo[1,2-a]pyridin-6-yl]pyridin-4-yl}methanol and the hydrochloride thereof;

[2-(2-Phenylimidazo[1,2-a]pyridin-6-yl)pyridin-4-yl]methanol;

[5-(2-p-Tolylimidazo[1,2-a]pyridin-6-yl)furan-2-yl]methanol;

[5-(2-Phenylimidazo[1,2-a]pyridin-6-yl)furan-2-yl]methanol;

{5-[2-(3-Methoxyphenyl)imidazo[1,2-a]pyridin-6-yl]furan-2-yl}methanol;

{5-[2-(2,4-Difluorophenyl)imidazo[1,2-a]pyridin-6-yl]furan-2-yl}methanol;

{5-[2-(4-Chlorophenyl)imidazo[1,2-a]pyridin-6-yl]furan-3-yl}methanol;

2-(4-Chlorophenyl)-6-(4-methoxymethyl-furan-2-yl)imidazo[1,2-a]pyridine;

{5-[2-(4-Hydroxymethylphenyl)imidazo[1,2-a]pyridin-6-yl]furan-2-yl}methanol;

4-[6-(5-Hydroxymethylfuran-2-yl)imidazo[1,2-a]pyridin-2-yl]-N,N-dimethylbenzamide;

{5-[2-(1H-Indol-6-yl)imidazo[1,2-a]pyridin-6-yl]furan-2-yl}methanol;

{5-[2-(2-Methoxypyridin-3-yl)imidazo[1,2-a]pyridin-6-yl]furan-2-yl}methanol;

[5-(2-Quinolin-5-ylimidazo[1,2-a]pyridin-6-yl)furan-2-yl]methanol;

{5-[2-(4-Morpholin-4-ylphenyl)imidazo[1,2-a]pyridin-6-yl]furan-2-yl}methanol;

[5-(2-Isoquinolin-5-ylimidazo[1,2-a]pyridin-6-yl)furan-2-yl]methanol;

(5-{2-[4-(1-Pyrrolidin-1-ylethyl)phenyl]imidazo[1,2-a]pyridin-6-yl}furan-2-yl)methanol;

4-[6-(5-Hydroxymethylthien-3-yl)imidazo[1,2-a]pyridin-2-yl]-N,N-dimethylbenzamide;

{4-[2-(2-Methoxypyridin-3-yl)imidazo[1,2-a]pyridin-6-yl]thien-2-yl}methanol;

[4-(2-Isoquinolin-5-ylimidazo[1,2-a]pyridin-6-yl)thien-2-yl]methanol;

N-{3-[6-(5-Hydroxymethylthien-3-yl)imidazo[1,2-a]pyridin-2-yl]phenyl}isobutyramide;

(4-{2-[4-(1-Pyrrolidin-1-ylethyl)phenyl]imidazo[1,2-a]pyridin-6-yl}thien-2-yl)methanol;

{4-[2-(4-Dimethylaminomethylphenyl)imidazo[1,2-a]pyridin-6-yl]thien-2-yl}methanol;

2-Fluoro-4-[6-(5-hydroxymethylthien-3-yl)imidazo[1,2-a]pyridin-2-yl]-N,N-dimethylbenzamide;

{4-[2-(3-Aminophenyl)imidazo[1,2-a]pyridin-6-yl]thien-2-yl}methanol;

N-tert-Butyl-5-[6-(5-hydroxymethylthien-3-yl)imidazo[1,2-a]pyridin-2-yl]nicotinamide;

[5-(3-Methyl-2-phenylimidazo[1,2-a]pyridin-6-yl)furan-2-yl]methanol;

[5-(3-Methyl-2-thien-2-ylimidazo[1,2-a]pyridin-6-yl)furan-2-yl]methanol;

{5-[2-(3-Chlorophenyl)-3-methylimidazo[1,2-a]pyridin-6-yl]furan-2-yl}methanol;

{5-[2-(4-Pyrrolidin-1-ylphenyl)imidazo[1,2-a]pyridin-6-yl]furan-2-yl}methanol;

3-[6-(5-Hydroxymethylfuran-2-yl)imidazo[1,2-a]pyridin-2-yl]benzonitrile;

[5-(2-Benzofuran-2-ylimidazo[1,2-a]pyridin-6-yl)furan-2-yl]methanol;

[5-(2-Benzothiazol-2-ylimidazo[1,2-a]pyridin-6-yl)furan-2-yl]methanol;

[5-(2-Benzo[b]thien-2-ylimidazo[1,2-a]pyridin-6-yl)furan-2-yl]methanol;

{4-[2-(4-Nitrophenyl)imidazo[1,2-a]pyridin-6-yl]thien-2-yl}methanol;

[4-(2-Thien-3-ylimidazo[1,2-a]pyridin-6-yl)thien-2-yl]methanol;

{4-[2-(4-Methylthiophenyl)imidazo[1,2-a]pyridin-6-yl]thien-2-yl}methanol;

{4-[2-(5-Chlorothien-2-yl)imidazo[1,2-a]pyridin-6-yl]thien-2-yl}methanol;

{4-[2-(4-Methylsulphonylphenyl)imidazo[1,2-a]pyridin-6-yl]thien-2-yl}methanol;

[4-(2-Benzo[b]thien-2-ylimidazo[1,2-a]pyridin-6-yl)thien-2-yl]methanol;

[4-(2-Benzo[b]thien-5-ylimidazo[1,2-a]pyridin-6-yl)thien-2-yl]methanol;

[4-(3-Methyl-2-phenylimidazo[1,2-a]pyridin-6-yl)thiazol-2-yl]methanol;

[4-(3-Methyl-2-thien-2-ylimidazo[1,2-a]pyridin-6-yl)thiazol-2-yl]methanol;

{4-[2-(4-Methoxyphenyl)-3-methylimidazo[1,2-a]pyridin-6-yl]thiazol-2-yl}methanol;

{4-[2-(4-Pyrrolidin-1-ylphenyl)imidazo[1,2-a]pyridin-6-yl]thiazol-2-yl}methanol;

{4-[2-(2-Fluorophenyl)imidazo[1,2-a]pyridin-6-yl]thiazol-2-yl}methanol;

{4-[2-(4-Methylsulphonylphenyl)imidazo[1,2-a]pyridin-6-yl]thiazol-2-yl}methanol;

[4-(2-Benzofuran-2-ylimidazo[1,2-a]pyridin-6-yl)thiazol-2-yl]methanol;

[4-(2-Benzo[b]thien-2-ylimidazo[1,2-a]pyridin-6-yl)thiazol-2-yl]methanol;

[4-(2-Furan-2-ylimidazo[1,2-a]pyridin-6-yl)thiazol-2-yl]methanol;

[4-(2-Benzo[b]thien-5-ylimidazo[1,2-a]pyridin-6-yl)thiazol-2-yl]methanol;

{4-[2-(4-Pyrrolidin-1-ylphenyl)imidazo[1,2-a]pyridin-6-yl]thien-2-yl}methanol;
1-{4-[2-(4-Chlorophenyl)imidazo[1,2-a]pyridin-6-yl]thien-2-yl}ethanol;
2-{4-[2-(4-Chlorophenyl)imidazo[1,2-a]pyridin-6-yl]thien-2-yl}propan-2-ol;
{5-[2-(4-Methoxyphenyl)-3-methylimidazo[1,2-a]pyridin-6-yl]furan-2-yl}methanol;
{5-[2-(4-Trifluoromethylphenyl)imidazo[1,2-a]pyridin-6-yl]furan-2-yl-methanol;
{5-[2-(4-Methoxyphenyl)imidazo[1,2-a]pyridin-6-yl]furan-2-yl}methanol;
{5-[2-(4-Fluorophenyl)imidazo[1,2-a]pyridin-6-yl]furan-2-yl}methanol;
{5-[2-(3,4-Difluorophenyl)imidazo[1,2-a]pyridin-6-yl]furan-2-yl}methanol;
[5-(2-Thien-3-ylimidazo[1,2-a]pyridin-6-yl)furan-2-yl]methanol;
{5-[2-(5-Chlorothien-2-yl)imidazo[1,2-a]pyridin-6-yl]furan-2-yl}methanol;
{5-[2-(2-Fluorophenyl)imidazo[1,2-a]pyridin-6-yl]furan-2-yl}methanol;
{5-[2-(3-Bromophenyl)imidazo[1,2-a]pyridin-6-yl]furan-2-yl}methanol;
{5-[2-(4-Chloro-3-methylphenyl)imidazo[1,2-a]pyridin-6-yl]furan-2-yl}methanol;
{5-[2-(4-Methylsulphonylphenyl)imidazo[1,2-a]pyridin-6-yl]furan-2-yl}methanol;
[5-(2-Thien-2-ylimidazo[1,2-a]pyridin-6-yl)furan-2-yl]methanol;
[5-(2-Benzofuran-3-ylimidazo[1,2-a]pyridin-6-yl)furan-2-yl]methanol;
{5-[2-(2,3-Dihydrobenzofuran-5-yl)imidazo[1,2-a]pyridin-6-yl]furan-2-yl}methanol;
[5-(2-Furan-2-ylimidazo[1,2-a]pyridin-6-yl)furan-2-yl]methanol;
[5-(2-Benzofuran-5-ylimidazo[1,2-a]pyridin-6-yl)furan-2-yl]methanol;
[5-(2-Thiazol-2-ylimidazo[1,2-a]pyridin-6-yl)furan-2-yl]methanol;
{5-[2-(4-Methylthiophenyl)imidazo[1,2-a]pyridin-6-yl]furan-2-yl}methanol;
{4-[2-(4-Chlorophenyl)-3-methylimidazo[1,2-a]pyridin-6-yl]thien-2-yl}methanol;
[4-(3-Methyl-2-thien-2-ylimidazo[1,2-a]pyridin-6-yl)thien-2-yl]methanol;
{4-[2-(3-Chlorophenyl)-3-methylimidazo[1,2-a]pyridin-6-yl]thien-2-yl}methanol;
{4-[2-(2,4-Difluorophenyl)-3-methylimidazo[1,2-a]pyridin-6-yl]thien-2-yl}methanol;
{4-[2-(4-Fluorophenyl)imidazo[1,2-a]pyridin-6-yl]thien-2-yl}methanol;
{4-[2-(3,4-Difluorophenyl)imidazo[1,2-a]pyridin-6-yl]thien-2-yl}methanol;
3-[6-(5-Hydroxymethylthien-3-yl)imidazo[1,2-a]pyridin-2-yl]benzonitrile;
{4-[2-(2-Fluorophenyl)imidazo[1,2-a]pyridin-6-yl]thien-2-yl}methanol;
{4-[2-(3-Bromophenyl)imidazo[1,2-a]pyridin-6-yl]thien-2-yl}methanol;
[4-(2-Benzofuran-2-ylimidazo[1,2-a]pyridin-6-yl)thien-2-yl]methanol;
[4-(2-Thien-2-ylimidazo[1,2-a]pyridin-6-yl)thien-2-yl]methanol;
[4-(2-Benzofuran-3-ylimidazo[1,2-a]pyridin-6-yl)thien-2-yl]methanol;
{4-[2-(1-Methyl-1H-benzimidazol-2-yl)imidazo[1,2-a]pyridin-6-yl]thien-2-yl}methanol;
{4-[2-(2,3-Dihydrobenzofuran-5-yl)imidazo[1,2-a]pyridin-6-yl]thien-2-yl}methanol;
[4-(2-Furan-2-ylimidazo[1,2-a]pyridin-6-yl)thien-2-yl]methanol;
[4-(2-Benzofuran-5-ylimidazo[1,2-a]pyridin-6-yl)thien-2-yl]methanol;
[4-(2-Thiazol-2-ylimidazo[1,2-a]pyridin-6-yl)thien-2-yl]methanol;
{4-[2-(4-Chlorophenyl)-3-methylimidazo[1,2-a]pyridin-6-yl]thiazol-2-yl}methanol;
{4-[2-(3-Chlorophenyl)-3-methylimidazo[1,2-a]pyridin-6-yl]thiazol-2-yl}methanol;
{4-[2-(4-Trifluoromethylphenyl)imidazo[1,2-a]pyridin-6-yl]thiazol-2-yl}methanol;
{4-[2-(4-Fluorophenyl)imidazo[1,2-a]pyridin-6-yl]thiazol-2-yl}methanol;
{4-[2-(3,4-Difluorophenyl)imidazo[1,2-a]pyridin-6-yl]thiazol-2-yl}methanol;
[4-(2-Thien-3-ylimidazo[1,2-a]pyridin-6-yl)thiazol-2-yl]methanol;
[4-(2-Pyridin-2-ylimidazo[1,2-a]pyridin-6-yl)thiazol-2-yl]methanol;
{4-[2-(5-Chlorothien-2-yl)imidazo[1,2-a]pyridin-6-yl]thiazol-2-yl}methanol;
{4-[2-(3-Bromophenyl)imidazo[1,2-a]pyridin-6-yl]thiazol-2-yl}methanol;
{4-[2-(4-Chloro-3-methylphenyl)imidazo[1,2-a]pyridin-6-yl]thiazol-2-yl}methanol;
[4-(2-Thien-2-ylimidazo[1,2-a]pyridin-6-yl)thiazol-2-yl]methanol;
[4-(2-Benzofuran-3-ylimidazo[1,2-a]pyridin-6-yl)thiazol-2-yl]methanol;
{4-[2-(2,3-Dihydrobenzofuran-5-yl)imidazo[1,2-a]pyridin-6-yl]thiazol-2-yl}methanol;
[4-(2-Benzofuran-5-ylimidazo[1,2-a]pyridin-6-yl)thiazol-2-yl]methanol;
[4-(2-Thiazol-2-ylimidazo[1,2-a]pyridin-6-yl)thiazol-2-yl]methanol;
{5-[2-(3-Hydroxymethylphenyl)imidazo[1,2-a]pyridin-6-yl]furan-2-yl}methanol;
N-{3-[6-(5-Hydroxymethylfuran-2-yl)imidazo[1,2-a]pyridin-2-yl]phenyl}isobutyramide;
2-Fluoro-4-[6-(5-hydroxymethylfuran-2-yl)imidazo[1,2-a]pyridin-2-yl]-N,N-dimethylbenzamide;
2-{4-[2-(1H-Indol-6-yl)imidazo[1,2-a]pyridin-6-yl]thien-2-yl}propan-2-ol;
N-{3-[6-(2-Hydroxymethylthiazol-4-yl)imidazo[1,2-a]pyridin-2-yl]phenyl}acetamide;
{4-[2-(4-Hydroxymethylphenyl)imidazo[1,2-a]pyridin-6-yl]thiazol-2-yl}methanol;
{4-[2-(3-Hydroxymethylphenyl)imidazo[1,2-a]pyridin-6-yl]thiazol-2-yl}methanol;
{4-[2-(1H-Indol-5-yl)imidazo[1,2-a]pyridin-6-yl]thiazol-2-yl}methanol;
{4-[2-(4-Methylthien-2-yl)imidazo[1,2-a]pyridin-6-yl]thiazol-2-yl}methanol;
{4-[2-(1H-Indol-4-yl)imidazo[1,2-a]pyridin-6-yl]thiazol-2-yl}methanol;
{4-[2-(2-Fluoropyridin-3-yl)imidazo[1,2-a]pyridin-6-yl]thiazol-2-yl}methanol;
3-[6-(2-Hydroxymethylthiazol-4-yl)imidazo[1,2-a]pyridin-2-yl]-N,N-dimethylbenzamide;
{4-[2-(1H-Indol-6-yl)imidazo[1,2-a]pyridin-6-yl]thiazol-2-yl}methanol;

{4-[2-(2-Methoxypyridin-3-yl)imidazo[1,2-a]pyridin-6-yl]thiazol-2-yl}methanol;
4-[6-(2-Hydroxymethylthiazol-4-yl)imidazo[1,2-a]pyridin-2-yl]-N-methylbenzamide;
{4-[2-(4-Methylthien-3-yl)imidazo[1,2-a]pyridin-6-yl]thiazol-2-yl}methanol;
{4-[2-(1-Methyl-1H-indol-5-yl)imidazo[1,2-a]pyridin-6-yl]thiazol-2-yl}methanol;
[4-(2-Quinolin-5-ylimidazo[1,2-a]pyridin-6-yl)-thiazol-2-yl]methanol;
N-{4-[6-(2-Hydroxymethylthiazol-4-yl)imidazo[1,2-a]pyridin-2-yl]phenyl}acetamide;
{4-[2-(4-Morpholin-4-ylphenyl)imidazo[1,2-a]pyridin-6-yl]thiazol-2-yl}methanol;
[4-(2-Isoquinolin-5-ylimidazo[1,2-a]pyridin-6-yl)thiazol-2-yl]methanol;
N-{3-[6-(2-Hydroxymethyl-thiazol-4-yl)imidazo[1,2-a]pyridin-2-yl]phenyl}isobutyramide;
3-[6-(2-Hydroxymethylthiazol-4-yl)imidazo[1,2-a]pyridin-2-yl]-N,N-dimethylbenzenesulphonamide;
{4-[2-(2,6-Difluoropyridin-4-yl)imidazo[1,2-a]pyridin-6-yl]thiazol-2-yl}methanol;
(4-{2-[1-(3-Methylbutyl)-1H-pyrazol-4-yl]imidazo[1,2-a]pyridin-6-yl}thiazol-2-yl)methanol;
2-{4-[2-(1H-Indol-6-yl)imidazo[1,2-a]pyridin-6-yl]-1H-pyrazol-3-yl}propan-2-ol;
2-{5-Fluoro-2-[2-(1H-indol-6-yl)imidazo[1,2-a]pyridin-6-yl]pyridin-4-yl}propan-2-ol;
2-{2-[2-(1H-Indol-6-yl)imidazo[1,2-a]pyridin-6-yl]pyridin-4-yl}propan-2-ol;
2-{2-[2-(1H-Indazol-3-yl)imidazo[1,2-a]pyridin-6-yl]pyridin-4-yl}propan-2-ol;
2-{2-[2-(5-Methylisoxazol-3-yl)imidazo[1,2-a]pyridin-6-yl]pyridin-4-yl}propan-2-ol;
{5-[2-(1H-Indol-6-yl)imidazo[1,2-a]pyridin-6-yl]-1-methyl-1H-imidazol-2-yl}methanol;
2-{5-[2-(4-Chlorophenyl)imidazo[1,2-a]pyridin-6-yl]furan-2-yl}propan-2-ol.

In accordance with the invention, the compounds of general formula (I) can be prepared according to the process described in Scheme 1.

The compounds of the invention can be prepared according to Scheme 1 (pathway A) by means of a coupling reaction, catalysed by a metal such as palladium, between an imidazopyridine of general formula (II), in which R and R1 are defined as above and Y represents a halogen atom or a boron derivative, and a derivative of general formula (III) in which Het and X are defined as above, Z represents a boron or tin derivative if Y represents a halogen atom, or else a halogen atom if Y represents a boron derivative, and R5 represents the group

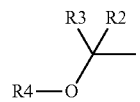

so as to obtain the compounds of general formula (I), for example, according to the method described by A. Gueiffier in *Helv. Chim. Acta* 2001, 84, 3610-3615.

The compounds of the invention can also be prepared according to Scheme 1 (pathway A') by means of a coupling reaction, catalysed by a metal such as palladium, between an imidazopyridine of general formula (II), in which R and R1 are defined as above and Y represents a halogen atom or a boron derivative, and a derivative of general formula (III'), in which Het and X are defined as above, Z represents a boron or tin derivative if Y represents a halogen atom, or else a halogen atom if Y represents a boron derivative, and R5' represents a carbonylated derivative R2CO, in which R2 is defined as above, or represents a $CO_2$-alkyl group, so as to obtain the compounds of general formula (IV), for example, according to the method described by A. Gueiffier in *Helv. Chim. Acta* 2001, 84, 3610-3615.

Next, the compounds of general formula (IV) can be converted to compounds of general formula (I), in which R4 represents a hydrogen atom, through the action of an organometallic derivative such as an organomagnesium compound, for example $R_3MgBr$, in which R3 is defined as above, or by reduction of the carbonyl group by means of a metal hydride, Scheme 1

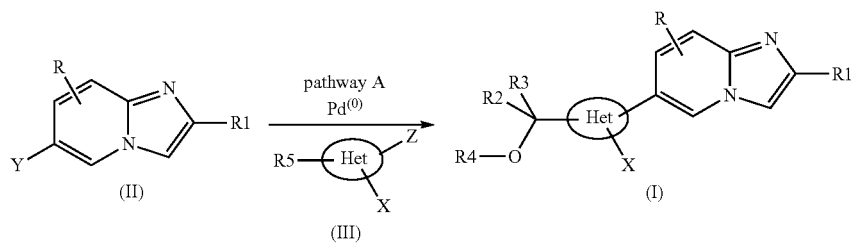

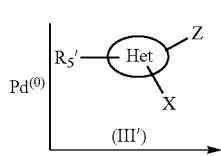

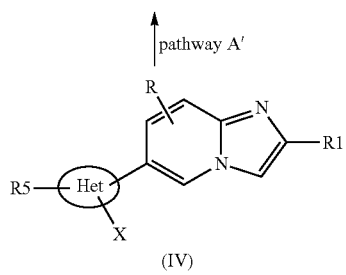

for example sodium borohydride or a derivative thereof, or any other method known to those skilled in the art.

In Scheme 1, the starting compounds and the reactants, when the method for preparing them is not described, are commercially available or described in the literature, or else can be prepared according to methods which are described therein or which are known to those skilled in the art. In particular, the imidazopyridines of general formula (II), in which Y represents a boron derivative, can be obtained, for example, according to the method described by E. DiMauro in *J. Org. Chem.* 2006, 71, 3959.

In accordance with the invention, the compounds of general formula (I) can also be prepared according to the process described in Scheme 2.

described by S. Buchwald in *J.A.C.S.* 2005, 127, 4685. Next, the compounds of general formula (IX) can be converted to compounds of general formula (I), in which R4 represents a hydrogen atom, by carrying out a deprotection reaction as described, for example, by T. Greene in "*Protective Groups in Organic Synthesis*" (Wiley Interscience), or by any method known to those skilled in the art.

The imidazopyridines of general formula (VII) can be obtained by means of a coupling reaction, catalysed by a metal such as palladium, between an imidazopyridine of general formula (V), in which R is defined as above and Y represents a boron derivative, and a derivative of general formula (VI), in which Het, R2, R3 and X are defined as above, R6 represents the group OR4 or a group OPG, in which

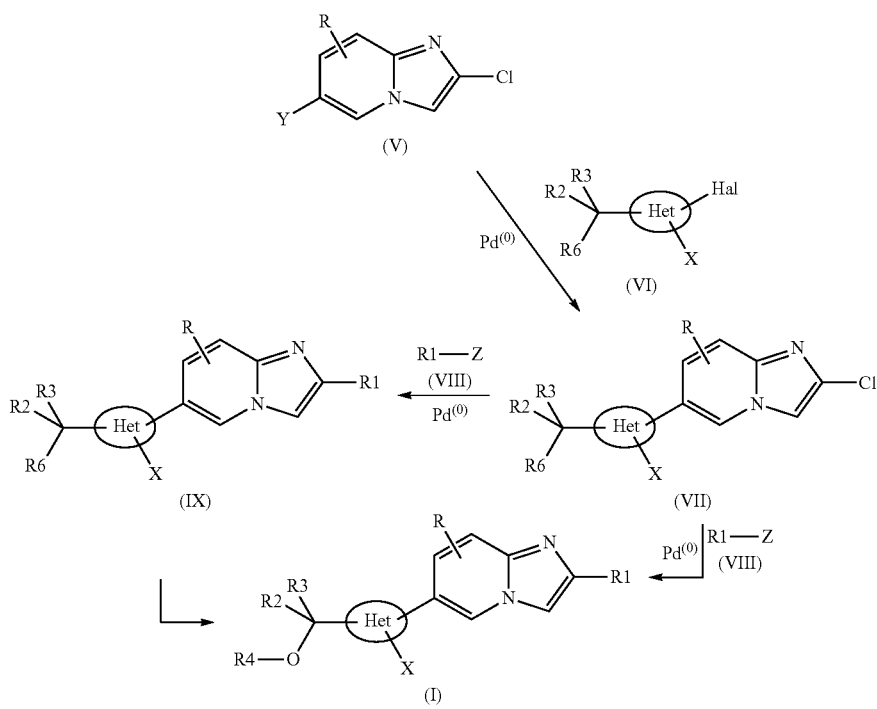

Scheme 2

The compounds of the invention can be prepared according to Scheme 2 by means of a coupling reaction, catalysed by a metal such as palladium, between an imidazopyridine of general formula (VII), in which Het, R, X, R2 and R3 are defined as above and R6 represents the group OR4, and a derivative of general formula (VIII), in which R1 is defined as above and Z represents a boron or tin derivative, so as to obtain the compounds of general formula (I), for example, according to the method described by S. Buchwald in *J.A.C.S.* 2005, 127, 4685.

The compounds of the invention can also be prepared according to Scheme 2 by means of a coupling reaction, catalysed by a metal such as palladium, between an imidazopyridine of general formula (VII), in which Het, R, X, R2 and R3 are defined as above and R6 represents OPG, in which PG represents a group protecting hydroxyl, as described, for example, by T. Greene in "*Protective Groups in Organic Synthesis*" (Wiley Interscience), and a derivative of general formula (VIII), in which R1 is defined as above and Z represents a boron or tin derivative, so as to obtain the compounds of general formula (IX), for example, according to the method PG represents a group protecting hydroxyl, and Hal represents a halogen atom other than chlorine, so as to obtain the compounds of general formula (VII), for example, according to the method described by A. Gueiffier in *Helv. Chim. Acta* 2001, 84, 3610-3615.

In Scheme 2, the starting compounds and the reactants, when the method for preparing them is not described, are commercially available or described in the literature, or else can be prepared according to methods which are described therein or which are known to those skilled in the art. In particular, the chlorinated imidazopyridines of general formula (V) can be obtained, for example, according to the method described by C. Townsend in *Syn. Commun.* 1997, 27, 1763-1765.

In accordance with the invention, the compounds of general formula (I), in which R represents a hydrogen atom or an alkyl group in the 3-position with respect to the imidazopyridine nucleus, can also be prepared according to the process described in Scheme 3.

Scheme 3

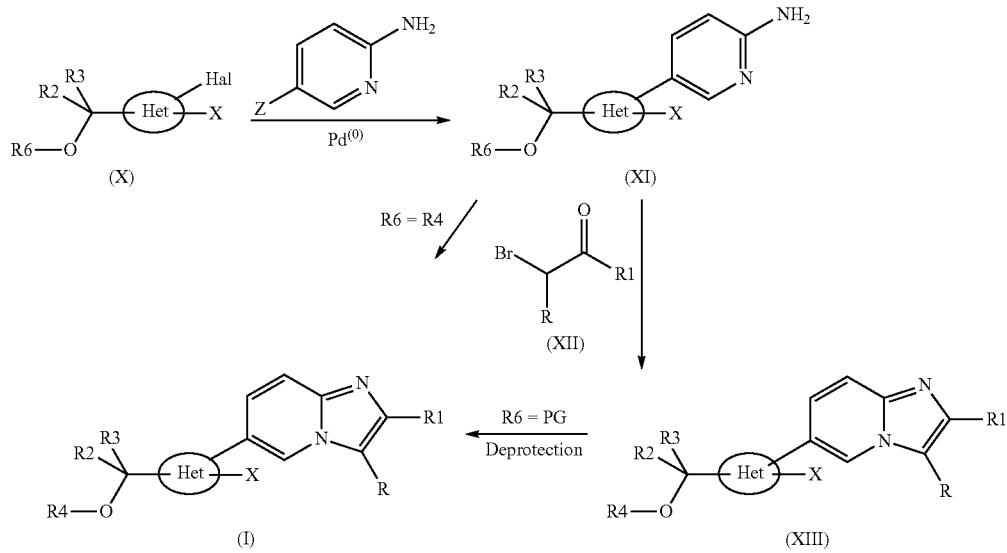

The compounds of the invention can be prepared according to Scheme 3 by means of a condensation reaction between an aminopyridine of general formula (XI), in which R2, R3 and X are defined as above, and R6 represents R4 or a hydroxyl function-protecting group PG, and a bromoketone of general formula (XII), in which R1 is defined as above and R represents a hydrogen atom or an alkyl group, so as to obtain either an imidazopyridine of general formula (I), in which R, R1, R2, R3, R4 and X are defined as above, or an imidazopyridine of general formula (XIII), in which R6 represents PG, for example according to the method described by M. Fisher in *J. Med. Chem.* 1972, 15, 982. As hydroxyl function protecting group, mention may be made of those described, for example, by T. Greene in "*Protective Groups in Organic Synthesis*" (Wiley Interscience), for example a tert-butyldimethylsilyl group.

Moreover, when R6 represents a hydroxyl function-protecting group PG, the compounds of general formula (XIII) are subjected to a deprotection reaction, as described, for example, by T. Greene in "*Protective Groups in Organic Synthesis*" (Wiley Interscience), so as to obtain the compounds of general formula (I), in which R is in the 3-position with respect to the imidazopyridine nucleus and R4 represents a hydrogen atom.

The compounds of general formula (XI) can be obtained by means of a coupling reaction, catalysed by a metal such as palladium, between a halogenated derivative of general formula (X), in which R2, R3, X and Hal are defined as above, and R6 represents R4 or a hydroxyl function-protecting group PG, and a 2-aminopyridine substituted with a group Z which represents a boron or tin derivative, such as, for example, 5-(4,4,5,5-tetramethyl-1,3,2-dioxaborolan-2-yl)pyridin-2-ylamine.

In general, the above intermediates can be subjected, if desired and if necessary, to any protection/deprotection reactions known to those skilled in the art before and/or after any reactions described in the schemes above.

The products of formula (I) can be subjected, if desired and if necessary, to any reactions known to those skilled in the art, in any order, in order to be converted into other products of formula (I).

By way of examples of reactions, mention may be made of: reactions for esterification or amidation of an acid function, carbamoylation reactions, ester function hydrolysis reactions, reactions for conversion of a hydroxyl function to an alkoxyl function, coupling reactions catalysed by a transition metal, reactions for protecting reactive functions, reactions for removing the protective groups that the protected reactive functions may bear, salification reactions with an inorganic or organic acid or with a base so as to obtain the corresponding salt, reactions for resolving racemic forms into enantiomers, said products of formula (I) thus obtained being, where appropriate, in all the possible racemic, enantiomeric and diastereoisomeric isomer forms.

According to another of its aspects, a subject of the invention is also the compounds of formulae (II-1), (II-2), (II-3), (II-4), (II-5), (II-6), (II-7), (V-1), (VII-1), (VII-2), (VII-3), (VII-4), (X-1), (X-2) and (X-3) and (X4). These compounds are of use as synthesis intermediates of the compounds of formula (I).

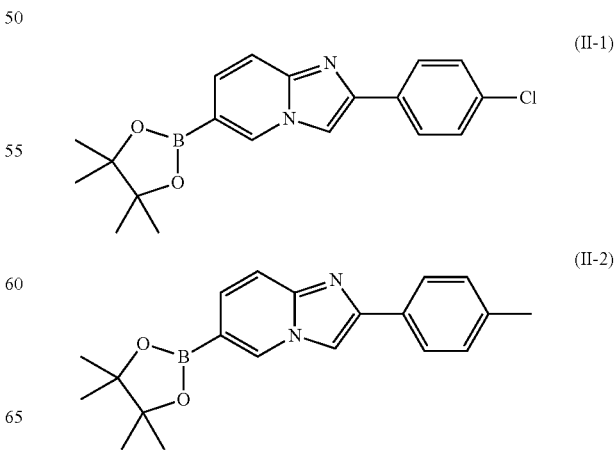

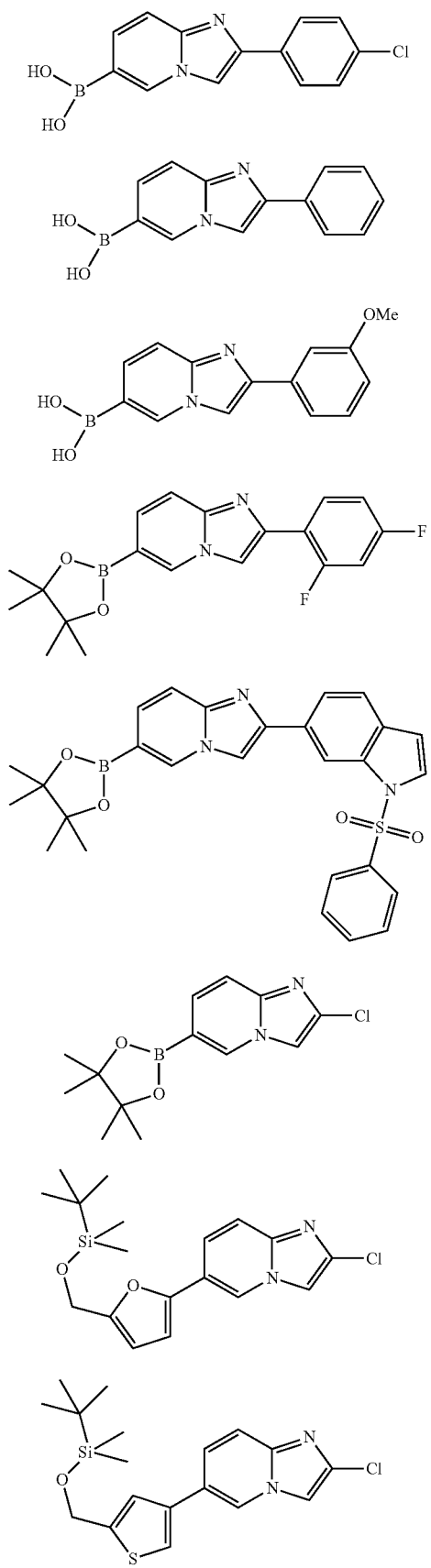
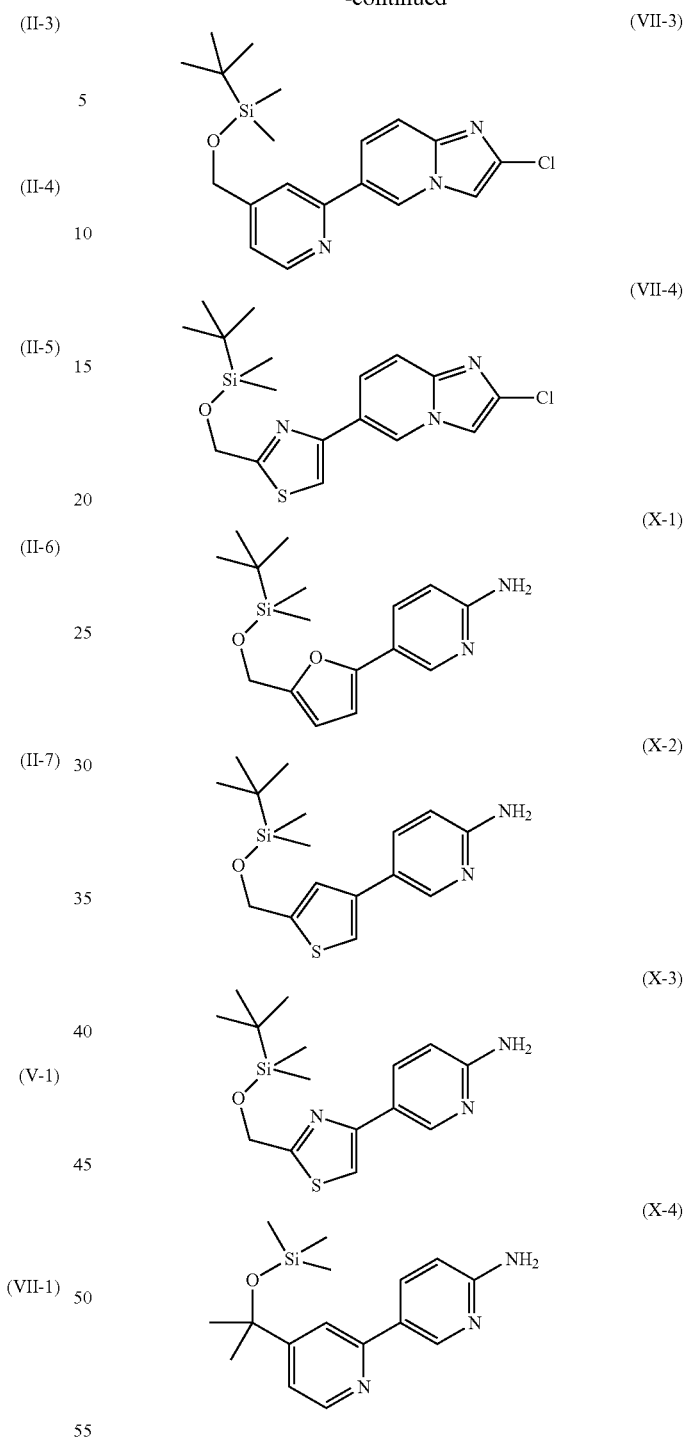

The compounds of formulae (II-1), (II-2), (II-3), (II-4), (II-5), (II-6) and (II-7) can be prepared in one stage (boronic esters) or two stages (boronic acids), for example according to the process described in Examples No. 2 and No. 6. In a first stage, a condensation can be carried out between an aminopyridine substituted with a boron derivative, such as, for example, a 5-(4,4,5,5-tetramethyl-1,3,2-dioxaborolan-2-yl) pyridin-2-ylamine, and an alpha-bromoketone, such as a 2-bromo-1-(aryl)ethanone, for example in a solvent such as n-propanol, in the presence of a base such as, for example, sodium hydrogen carbonate, so as to obtain the corresponding boronate esters. Next, in a second stage, the boronic esters are hydrolysed to the corresponding boronic acids, for example in a mixture of acetone, water and hydrochloric acid.

The compound of formula (V-1) can be prepared, for example, according to the process described in Example No. 3. In a first stage, a condensation can be carried out between an aminopyridine substituted with a boron derivative, such as, for example, 5-(4,4,5,5-tetramethyl-1,3,2-dioxaborolan-2-yl)pyridin-2-ylamine, and ethyl 2-bromoacetate. In a second stage, the compound is subjected to a reaction of cyclisation and of chlorination in the presence of a chlorinating agent such as phosphorus oxychloride, which gives the compound (V-1).

The compounds of formulae (VII-1), (VII-2), (VII-3) and (VII-4) can be prepared by means of a coupling reaction, catalysed by a metal such as palladium, between, for example, the compound (V-1) and a halogenated, for example brominated, heterocycle comprising a protected alcohol function, for example protected with a tert-butyldimethylsilanyl group, as described in Examples No. 3 and 4.

The compounds of formulae (X-1), (X-2), (X-3) and (X-4) can be prepared by condensation between an aminopyridine substituted with a boron derivative, such as, for example, 5-(4,4,5,5-tetramethyl-1,3,2-dioxaborolan-2-yl)pyridin-2-ylamine, and a halogenated, for example, brominated, heterocycle comprising a protected alcohol function, for example protected with a tert-butyldimethylsilanyl or trimethylsilanyl group, for example according to the process described in Examples No. 5, 6 and 7.

The compounds of formulae (II-1), (II-2), (II-3), (II-4), (II-5), (II-6), (V-1), (VII-1), (VII-2), (VII-3), (VII-4), (X-1), (X-2), (X-3) and (X-4) were prepared in the form of a powder or of an oil, in the form of a base or of an addition salt with an acid. Table 1 gives some physicochemical data of these intermediates.

In this table, in the "salt/base" column, "-" represents a compound in free base form, whereas "HCl" represents a compound in hydrochloride form, and the ratio between parentheses is the (acid:base) ratio.

TABLE 1

| No. | $^1$H NMR (DMSO-d6, δ ppm); M + H; Mp | Salt/base |
|---|---|---|
| (II-1) | 1.35 (s, 12H); 7.35 (d, 1H); from 7.5 to 7.6 (m, 3H); 7.95 (d, 2H); 8.45 (d, 1H); 7.85 (s, 1H). M + H = 355. | — |
| (II-2) | 1.45 (s, 12H); 2.45 (s, 3H); 7.3 (d, 2H); from 7.5 to 7.7 (m, 2H); from 7.85 to 8 (m, 3H); 8.6 (s, 1H); M + H = 335 | — |
| (II-3) | From 7.6 to 7.75 (m, 2H); 7.95 (m, 1H); from 8.05 to 8.15 (m, 2H); 8.2 (m, 1H); 8.9 (s, 1H); 9.1 (s, 1H). M + H = 273. | HCl (1:1) |
| (II-4) | 7.55 (m, 1H); 7.6 (m, 2H); 8.0 (m, 1H); 8.1 (m, 2H); 8.25 (d, 1H); 8.9 (s, 1H); 9.1 (s, 1H). M + H = 275 | HCl (1:1) |
| (II-5) | 3.75 (s, 3H); 6.95 (d, 1H); from 7.3 to 7.65 (m, 3H); 7.8 (d, 1H); 8.05 (d, 1H); 8.75 (s, 1H); 8.9 (s, 1H). M + H = 325 | HCl (1:1) |
| (II-6) | 1.35 (s, 12H); 7.25 (t, 1H); from 7.35 to 7.45 (m, 2H); 7.6 (d, 1H); from 8.25 to 8.35 (m, 1H); 8.45 (s, 1H); 8.9 (s, 1H) M+ = 356. | — |
| (II-7) | 1.4 (s, 12H); 6.95 (d, 1H); from 7.55 to 7.85 (m, 7H); 7.95 (d, 1H); 8.05 (m, 2H); 8.55 (s, 1H); 8.75 (s, 1H); 9.05 (s, 1H). | HBr(1:1) |
| (V-1) | 1.35 (m, 12H); 7.4 (d, 1H); 7.5 (d, 1H); 8.1 (s, 1H); 8.85 (s, 1H); M + H = 279; Mp = 115-120° C. | — |
| (VII-1) | 0.0 (s, 6H); 0.8 (s, 9H); 4.6 (s, 2H); 6.2 (d, 1H); 6.45 (d, 1H); 7.3 (d, 1H); from 7.4 to 7.45 (m, 2H); 8.25 (s, 1H | — |
| (VII-2) | 0.0 (s, 6H); 0.8 (s, 9H); 4.8 (s, 2H); 7.3 (s, 1H); 7.45 (d, 1H); 7.6 (d, 1H); 7.75 (s, 1H); 7.9 (s, 1H); 8.8 (s, 1H). | — |
| (VII-3) | (CDCl$_3$, δ in ppm): 0 (s, 6H); 0.85 (s, 9H); 4.65 (s, 2H); 7.1 (m, 1H); 7.45 to 7.55 (m, 3H); 7.65 (dd, 1H); 8.45 (d, 1H); 8.7 (s, 1H). M + H = 374; Mp = 111-114° C. | — |
| (VII-4) | 0.0 (s, 6H); 0.8 (s, 9H); 4.85 (s, 2H); 7.45 (d, 1H); 7.75 (d, 1H); 8.0 (m, 2H); 8.95 (s, 1H). | — |
| (X-1) | 0.0 (s, 6H); 0.8 (s, 9H); 4.55 (s, 2H); 6.05 (s, 2H); 6.3 (s, 1H); 6.4 (d, 1H); 6.5 (s, 1H); 7.55 (d, 1H); 8.2 (s, 1H). M + H = 305 | — |
| (X-2) | 0.0 (s, 6H); 0.8 (s, 9H); 4.85 (s, 2H); 5.85 (s, 2H); 6.4 (d, 1H); 7.2 (s, 1H); 7.4 (s, 1H); 7.55 (d, 1H); 8.15 (s, 1H). | — |
| (X-3) | 0.0 (s, 6H); 0.8 (s, 9H); 4.85 (s, 2H); 5.95 (s, 2H); 6.35 (d, 1H); 7.6 (s, 1H); 7.75 (d, 1H); 8.35 (s, 1H). | — |
| (X-4) | (CDCl$_3$, δ in ppm): 0 (s, 9H); 1.4 (s, 6H); 4.4 (s, 2H); 6.45 (d, 1H); 7.05 (m, 1H); 7.55 (s, 1H); 7.95 (m, 1H); 8.4 (d, 1H); 8.5 (m, 1H). M + H = 302 | — |

The following examples describe the preparation of certain compounds in accordance with the invention. These examples are not limiting and merely illustrate the present invention.

The nomenclature of the compounds was established on the basis of the Autonom software.

EXAMPLE 1

{5-[2-(4-Chlorophenyl)imidazo[1,2-a]pyridin-6-yl]furan-2-yl}methanol (Compound 1 of the Table)

1.1 2-(4-Chlorophenyl)-6-iodoimidazo[1,2-a]pyridine 5.0 g of 2-amino-5-iodopyridine, 5.3 g of 2-bromo-1-(4-chlorophenyl)ethanone and 2.67 g of sodium hydrogen carbonate in 150 ml of n-propanol are placed in a round-bottomed flask. The mixture is heated at 80° C. for 40 h and left to cool, and 700 ml of water are added. The precipitate is recovered by filtration, washed with water and dried under reduced pressure. 5.51 g of compound are obtained.

$^1$H NMR (DMSO-d6, δ in ppm): 7.45 (s, 2H); 7.55 (d, 2H); 8 (d, 2H); 8.35 (s, 1H); 8.95 (s, 1H). M+H=355.

1.2 5-[2-(4-Chlorophenyl)imidazo[1,2-a]pyridin-6-yl]furan-2-carbaldehyde 300 mg of 2-(4-chlorophenyl)-6-iodoimidazo[1,2-a]pyridine, 118 mg of 5-formyl-2-furanboronic acid, 89 mg of [1,1'-bis(diphenylphosphino)ferrocene]dichloropalladium, 280 mg of potassium carbonate, 1.5 ml of ethanol and 1 ml of water are placed in a microwave tube and degassed with argon. The tube is placed in a microwave apparatus and irradiated at 90° C. for 30 min. After cooling, the catalyst is removed by filtration and washed with ethyl acetate. The organic phase is separated and dried and the filtrate is concentrated under reduced pressure. The residue is purified by silica gel chromatography, elution being carried out with a dichloromethane/methanol mixture. 104 mg of compound are obtained.

$^1$H NMR (DMSO-d6, δ in ppm): 7.30 (d, 1H); 7.54 (m, 2H); 7.71 (d, 1H); from 7.74 to 7.79 (m, 2H); 8.01 (m, 2H); 8.55 (s, 1H); 9.16 (m, 1H); 9.65 (s, 1H). M+H=323.

1.3 {5-[2-(4-Chlorophenyl)imidazo[1,2-a]pyridin-6-yl]furan-2-yl}methanol 122 mg of sodium borohydride are added, in small portions, to 104 mg of 5-[2-(4-chlorophenyl)imidazo[1,2-a]pyridin-6-yl]furan-2-carbaldehyde dissolved in 20 ml of methanol. The mixture is subsequently stirred at ambient temperature for 2 hours, and the solvent is then evaporated off under reduced pressure. The residue is taken up between dichloromethane and water. The organic phase is separated, dried over sodium sulphate and concentrated under reduced pressure. 39 mg of compound are obtained.

Mp=197-199° C. $^1$H NMR (DMSO-d6, δ in ppm): 4.5 (d, 2H); 5.3 (t, 1H); 6.5 (m, 1H); 7.95 (m, 1H); 7.55 (m, 2H); from 7.60 to 7.70 (m, 2H); 8 (m, 2H); 8.5 (s, 1H); 8.85 (s, 1H). M+H=325

EXAMPLE 2

{4-[2-(4-Chlorophenyl)imidazo[1,2-a]pyridin-6-yl]thiazol-2-yl}methanol (Compound 11 of the Table)

2.1 2-(4-Chlorophenyl)-6-(4,4,5,5-tetramethyl-1,3,2-dioxaborolan-2-yl)imidazo[1,2-a]pyridine 2.5 g of 5-(4,4,5,5-tetramethyl-1,3,2-dioxaborolan-2-yl)pyridin-2-ylamine and 2.65 g of 2-bromo-1-(4-chlorophenyl)ethanone in 76 ml of n-propanol are placed in a round-bottomed flask. 1.33 g of sodium hydrogen carbonate are added thereto. The mixture is heated at 80° C. for 16 h. The reaction mixture is left to cool and concentrated under reduced pressure. The residue is taken up between water and ethyl acetate, the organic phase is then separated by settling out and dried over magnesium sulphate, and the solvent is then evaporated off under reduced pressure. 3.75 g of compound are obtained.

$^1$H NMR (DMSO-d6, δ in ppm): 1.35 (s, 12H); 7.35 (d, 1H); from 7.5 to 7.6 (m, 3H); 7.95 (d, 2H); 8.45 (d, 1H); 7.85 (s, 1H). M+H=355.

2.2 [2-(4-chlorophenyl)imidazo[1,2-a]pyridin-6-yl]boronic acid hydrochloride (1:1)

3.60 g of 2-(4-chlorophenyl)-6-(4,4,5,5-tetramethyl-1,3,2-dioxaborolan-2-yl)imidazo[1,2-a]pyridine are dissolved in 112 ml of acetone and 56 ml of water; 101 ml of 1N hydrochloric acid are added thereto, dropwise and with stirring, and the mixture is stirred at ambient temperature for 24 h. The reaction mixture is then concentrated under reduced pressure. The solid obtained is titurated with diethyl ether and recovered by filtration, and then dried in an oven under reduced pressure at 60° C. 3.12 g of compound are obtained.

$^1$H NMR (DMSO-d6, δ in ppm): from 7.6 to 7.75 (m, 2H); 7.95 (m, 1H); from 8.05 to 8.15 (m, 2H); 8.2 (m, 1H); 8.9 (s, 1H); 9.1 (s, 1H). M+H=273.

2.3 {4-[2-(4-Chlorophenyl)imidazo[1,2-a]pyridin-6-yl]thiazol-2-yl}methanol 28 ml of dimethoxyethane and 14 ml of a 2M solution of sodium carbonate are placed in a round-bottomed flask and the mixture is degassed with argon for 10 min. 768 mg of [2-(4-chlorophenyl)imidazo[1,2-a]pyridin-6-yl]boronic acid, 482 mg of (4-bromothiazol-2-yl)methanol and 144 mg of tetrakis(triphenylphosphine)palladium are added. The mixture is left to stir for 16 h at 80° C. The solvent is then evaporated off under reduced pressure. The residue obtained is taken up with ethyl acetate. A precipitate forms, and is recovered by filtration and washed with ethyl acetate. The compound is then purified by silica gel chromatography, elution being carried out with a dichloromethane/methanol mixture. The solid obtained is titurated with diethyl ether and recovered by filtration, and then oven-dried under reduced pressure at 50° C. 350 mg of compound are obtained.

Mp=190-192° C. $^1$H NMR (DMSO-d6, δ in ppm): 4.85 (s, 2H); 6.2 (t, 1H), from 7.50 to 7.60 (m, 2H); 7.7 (d, 1H); 7.85 (d, 1H); from 7.95 to 8.05 (m, 2H); 8.1 (s, 1H); 8.5 (s, 1H); 9.1 (s, 1H). M+H=342.

EXAMPLE 3

[4-[2-quinolin-3-yl)imidazo[1,2-a]pyridin-6-yl]thien-2-yl]methanol hydrochloride (1:2) (Compound 16 of the Table)

3.1 [4-(Bromothien-2-yl)methyloxy]-tert-butyldimethylsilane 900 mg of (4-bromothien-2-yl)methanol are placed in a round-bottomed flask and dissolved in 45 ml of tetrahydrofuran. 440 mg of 1H-imidazole are added thereto, followed by 910 mg of tert-butyl(chloro)dimethylsilane, and the mixture is left to stir at ambient temperature for 48 hours. The reaction mixture is then hydrolysed with water, and the organic phase, which has been extracted with ethyl acetate, is separated, dried over magnesium sulphate and concentrated under reduced pressure. The residue obtained is purified by silica gel chromatography, elution being carried out with a heptane/ethyl acetate mixture. 1.2 g of compound are obtained.

$^1$H NMR spectrum (CDCl$_3$, δ in ppm): 0 (s, 6H); 0.85 (s, 9H); 4.7 (s, 2H); 6.7 (s, 1H); 7.0 (s, 1H). M+H=308.

3.2 Ethyl[2-imino-5-(4,4,5,5-tetramethyl-1,3,2-dioxaborolan-2-yl)-2H-pyridin-1-yl]acetate hydrobromide 5.0 g of 5-(4,4,5,5-tetramethyl-1,3,2-dioxaborolan-2-yl)pyridin-2-ylamine in 7.6 ml of ethyl 2-bromoacetate are placed in a round-bottomed flask and the mixture is stirred at ambient temperature for 20 h. A precipitate forms, and is recovered by filtration, washed with diethyl ether and then with ethanol, and oven-dried under reduced pressure. 8.78 g of compound are obtained.

$^1$H NMR spectrum (DMSO-d6, δ in ppm): 1.3 (m, 15H); from 4.1 to 4.25 (m, 2H); 5.2 (s, 2H); 7.1 (d, 1H); 8.0 (d, 1H); 8.3 (s, 1H); 9.0 (s, 1H). M+H=388.

3.3 2-Chloro-6-(4,4,5,5-tetramethyl-1,3,2-dioxaborolan-2-yl)imidazo[1,2-a]pyridine 8.78 g of ethyl [2-imino-5-(4,4,5,5-tetramethyl-1,3,2-dioxaborolan-2-yl)-1H-pyridin-1-yl]acetate hydrobromide in 20 ml of POCl$_3$ are placed in a round-bottomed flask. The reaction mixture is heated at 105° C. for 16 h, cooled to ambient temperature and concentrated under reduced pressure. The residue is taken up between dichloromethane and water at 0° C., and a 30% aqueous solution of NH$_4$OH is added until a basic pH is obtained. The organic phase is separated, dried over magnesium sulphate and concentrated under reduced pressure. 4.3 g of compound are obtained.

Mp=115-120° C. $^1$H NMR spectrum (DMSO-d6, δ in ppm): 1.35 (m, 12H); 7.4 (d, 1H); 7.5 (d, 1H); 8.1 (s, 1H); 8.85 (s, 1H). M+H=279.

3.4 6-[5-[(tert-Butyldimethylsilanyl)oxymethyl]thien-3-yl]-2-chloroimidazo[1,2-a]pyridine 1.0 g of [(4-bromothien-2-yl)methyloxy]tert-butyldimethylsilane in 16 ml of tetrahydrofuran and 4 ml of water are placed in a round-bottomed flask and degassed under a stream of argon for 10 min. 1.0 g of 2-chloro-6-(4,4,5,5-tetramethyl-1,3,2-dioxaborolan-2-yl)imidazo[1,2-a]pyridine, 210 mg of [1,1'-bis(diphenyl-phosphino)ferrocene]dichloropalladium and 3.2 g of caesium carbonate are added thereto, and the mixture is heated at 80° C. for 16 hours. After cooling, the reaction mixture is concentrated under reduced pressure. The residue obtained is purified by silica gel chromatography, elution being carried out with a heptane/ethyl acetate mixture. 450 mg of compound are obtained.

Mp=100-104° C. $^1$H NMR spectrum (CDCl$_3$, δ in ppm): 0 (s, 6H); 0.8 (s, 9H); 4.8 (s, 2H); 7.3 (s, 1H); 7.45 (d, 1H); 7.6 (d, 1H); 7.75 (s, 1H); 7.9 (s, 1H); 8.75 (s, 1H). M+H=379.

3.5 3-{6-[5-((tert-Butyldimethylsilanyl)oxymethyl)thien-3-yl]imidazo[1,2-a]pyridin-2-yl}quinoline In a reactor, 150 mg of 6-[5-[(tert-butyldimethylsilanyl)oxymethyl]thien-3-yl]-2-chloroimidazo[1,2-a]pyridine are placed in 2 ml of toluene and the mixture is degassed with argon for 10 min. 3 mg of palladium acetate, 11 mg of 2-dicyclohexylphosphino-2',6'-dimethoxy-1,1'-biphenyl, 170 mg of K$_3$PO$_4$, 110 mg of 3-quinolineboronic acid and a few drops of ethanol are then added. The reaction mixture is heated at 115° C. for 16 h, cooled to ambient temperature and concentrated under reduced pressure. The residue is then purified by silica gel chromatography, elution being carried out with a heptane/ethyl acetate mixture. 200 mg of compound are obtained.

M+H=472.

3.6 [4-(2-Quinolin-3-yl)imidazo[1,2-a]pyridin-6-yl]thien-2-yl]methanol 190 mg of 3-{6-[5-[(tert-butyldimethylsilanyl)oxymethyl]thien-3-yl]imidazo[1,2-a]pyridin-2-yl}quinoline in 4 ml of tetrahydrofuran are placed in a round-bottomed flask, and 210 mg of tetrabutylammonium fluoride are added. After stirring for 48 hours at ambient temperature, the reaction mixture is concentrated under reduced pressure. The residue is then purified by silica gel chromatography, elution being carried out with a dichloromethane/methanol mixture. 100 mg of compound are obtained.

$^1$H NMR spectrum (DMSO-d6, δ in ppm): 4.7 (d, 2H); 5.55 (t, 1H); 7.5 (s, 1H); from 7.65 to 7.8 (m, 4H); from 7.9 (s, 1H); 8.05 to 8.15 (m, 2H); 8.65 (s, 1H); 8.9 (s, 1H); 9.0 (s, 1H); 9.55 (1H). M+H=358.

3.7 [4-[(2-Quinolin-3-yl)imidazo[1,2-a]pyridin-6-yl]thien-2-yl]methanol hydrochloride (1:2)

100 mg of [4-[(2-quinolin-3-yl)imidazo[1,2-a]pyridin-6-yl]thien-2-yl]methanol are suspended in dichloromethane and methanol. The solution is passed through a frit and 5.6 ml of a 0.1N solution of hydrochloric acid in isopropanol are added to the filtrate. The reaction mixture is then concentrated under reduced pressure and the residue is then taken up in diethyl ether. The precipitate is recovered by filtration and oven-dried under reduced pressure. 106 mg of compound are obtained.

Mp=310-315° C. $^1$H NMR spectrum (DMSO-d6, δ in ppm): 4.75 (s, 2H); 7.55 (s, 1H); 7.8 (t, 1H); from 7.9 to 8.0 (m, 2H); 8.05 (s, 1H); from 8.17 to 8.25 (m, 3H); 8.9 (s, 1H); 9.28 (s, 1H); 9.32 (s, 1H); 9.67 (s, 1H). M+H=431.

EXAMPLE 4

{5-[2-(1H-Indol-6-yl)imidazo[1,2-a]pyridin-6-yl]furan-2-yl}methanol (Compound 32 of the Table)

4.1 (5-Bromofuran-2-yl)methanol

In a 1 l round-bottomed flask, 10 g (0.052 mol) of 5-bromofuroic acid are dissolved in 350 ml of THF, 5.8 g (0.057 mol) of N-methylmorpholine are added, and the mixture is cooled using an ice bath. 7.5 g (0.055 mol) of isobutyl chloroformate in solution in 50 ml of THF are added using a dropping funnel. When the addition is complete, the mixture is left to stir for one hour in the cold, and then the solid formed is removed by filtration through celite. The filtrate is cooled with an ice bath, and then 4.95 g of sodium borohydride and, finally, very slowly, 50 ml of methanol are added. The mixture is left to stir for one hour in the cold and then the solvents are evaporated off under reduced pressure. The residue is taken up between water and diethyl ether, and the organic phase is separated by settling out, washed with water and dried over sodium sulphate. After evaporation of the solvent, 9.1 g of oil are obtained, and used without purification for the subsequent stage.

4.2 [(5-Bromofuran-2-yl)methyloxy]-tert-butyldimethylsilane 9.1 g (0.051 mol) of the compound obtained in 4.1 are dissolved in 150 ml of THF. 5.2 g (0.077 mol) of imidazole are added thereto, followed by 10 g of chloro-tert-butyldimethylsilane, and the mixture is left to stir for 16 hours at ambient temperature. The solvent is then evaporated off under reduced pressure, the residue is taken up between water and diethyl ether, the resulting product is separated by settling out, and the organic phase is washed with water and dried over sodium sulphate. After evaporation of the solvent, the product is purified by chromatography, elution being carried out with a heptane/ethyl acetate mixture. 10.1 g of compound are obtained.

¹H NMR (CDCl₃, δ in ppm): 0.0 (s, 6H); 0.8 (s, 9H); 4.45 (s, 2H); 6.2 (s, 1H); 7.2 (s, 1H)

4.3 6-[5-(tert-Butyldimethylsilanyloxymethyl)furan-2-yl]-2-chloroimidazo[1,2-a]pyridine In a 150 ml round-bottomed flask, 68 ml of THF and 12 ml of water are degassed for 15 minutes under argon, and then 4.56 g (15.7 mmol) of the compound obtained in 4.2, 4.36 g (15.7 mmol) of the compound obtained in 3.3, 15.3 g (47 mmol) of caesium carbonate and 0.38 g of [1,1'-bis(diphenylphosphino)ferrocene]dichloropalladium are added and the mixture is heated in a thermostated bath at 80° C. for 1 h 30. The solvents are then evaporated off under reduced pressure, the residue is taken up between water and diethyl ether, and the resulting product is separated by settling out and dried over sodium sulphate. After evaporation of the solvent, the product is purified by chromatography, elution being carried out with a dichloromethane/methanol mixture, and then recrystallization from cyclohexane. 4.2 g of compound are obtained.

¹H NMR (DMSO-d6, δ in ppm): 0.0 (s, 6H); 0.8 (s, 9H); 4.6 (s, 2H); 6.2 (d, 1H); 6.45 (d, 1H); 7.3 (d, 1H); from 7.4 to 7.45 (m, 2H); 8.25 (s, 1H).

4.4 6-[5-(tert-Butyldimethylsilanyloxymethyl)furan-2-yl]-2-(1H-indol-6-yl)imidazo[1,2-a]pyridine 108 mg (0.3 mmol) of the compound obtained in 4.3 are placed in a tube, and 0.35 mmol of potassium phosphate, 1 ml of n-butanol and 30 mg of indole-6-boronic acid in solution in 2 ml of degassed toluene are added. The tube is flushed with argon and a solution of 0.0036 mmol of palladium acetate and of 0.0072 mmol of 2-dicyclohexylphosphino-2',6'-dimethoxy-1,1'-biphenyl in 1 ml of toluene is added thereto. The tube is closed and stirred for 16 h at 110° C. The cooled solution is diluted with 5 ml of ethyl acetate, 100 mg of silica-propanethiol are added thereto, and the mixture is stirred for 4 h at ambient temperature. The solid is separated by filtration and washed with ethyl acetate. The filtrate is evaporated to dryness and used as it is for the next stage.

4.5 {5-[2-(1H-Indol-6-yl)imidazo[1,2-a]pyridin-6-yl]furan-2-yl}methanol

The compound obtained in 4.4 is dissolved in 5 ml of THF containing 0.36 mmol of tetrabutylammonium fluoride hydrate. The mixture is stirred for 16 h at ambient temperature, and the solvent is then evaporated off under reduced pressure. The compound is purified by chromatography. 3.9 mg of compound are obtained.

¹H NMR (DMSO-d6, δ in ppm): 4.45 (m, 2H); 5.3 (m, 1H); 6.45 (m, 2H); 6.9 (s, 1H); 7.4 (m, 1H); 7.55 to 7.65 (m, 4H); 8 (s, 1H); 8.4 (m, 1H); 8.85 (s, 1H); 11.2 (s, 1H). M+H=330.

EXAMPLE 5

{4-[2-(2-Fluorophenyl)imidazo[1,2-a]pyridin-6-yl]thiazol-2-yl}methanol (Compound 66 of the Table)

5.1 4-Bromo-2-(tert-butyldimethylsilanyloxymethyl)thiazole

By carrying out the process as in Example 4.2 and using 5.0 g of (4-bromothiazol-2-yl)methanol dissolved in 255 ml of tetrahydrofuran, 2.28 g of 1H-imidazole and 4.66 g of tert-butylchlorodimethylsilane, 8.18 g of compound are obtained.

¹H NMR (DMSO-d6, δ in ppm): 0.0 (s, 6H); 0.8 (s, 9H); 4.85 (s, 2H); 7.7 (s, 1H).

5.2 5-[2-(tert-Butyl-dimethylsilanyloxymethyl)thiazol-4-yl]pyridin-2-ylamine 8.0 g of the compound obtained in stage 5.1, 6.56 g of 5-(4,4,5,5-tetramethyl-1,3,2-dioxaborolan-2-yl)pyridin-2-ylamine, 49.7 ml of 2M solution of sodium carbonate and 1.01 g of [1,1'-bis(diphenylphosphino)ferrocene]dichloropalladium are dissolved in 310 ml of N,N-dimethylformamide and placed in a round-bottomed flask under an argon stream. The mixture is heated for 2 h30 at 80° C. After cooling to ambient temperature, 600 ml of ethyl acetate are added to the reaction medium, and the resulting mixture is filtered through celite. The organic phase is then separated, washed three times with a saturated solution of sodium chloride, dried over magnesium sulphate and concentrated under reduced pressure. The residue is purified by silica gel chromatography, elution being carried out with a dichloromethane/ethyl acetate mixture. The solid obtained is titurated from diisopropyl ether, recovered by filtration and then oven-dried under reduced pressure. 4.5 g of compound are obtained.

¹H NMR (DMSO-d6, δ in ppm): 0.0 (s, 6H); 0.8 (s, 9H); 4.85 (s, 2H); 5.95 (s, 2H); 6.35 (d, 1H); 7.6 (s, 1H); 7.75 (d, 1H); 8.35 (s, 1H).

5.3 6-[2-(tert-Butyldimethylsilanyloxymethyl)thiazol-4-yl]-2-(2-fluorophenyl)imidazo[1,2-a]pyridine 58.8 mg (0.7 mmol) of sodium bicarbonate are weighed into a microwave tube. 57 mg (0.25 mmol) of the compound obtained in 5.2, in solution in 2 ml of propan-1-ol, are added thereto, followed by 92 mg (0.375 mmol) of 2-bromo-1-(2-fluorophenyl)ethanone in solution in 1 ml of propan-1-ol. The tube is sealed and then stirred for 16 h at 80° C. The reaction mixture is cooled to ambient temperature, 200 mg of propanethiol supported on silica (Biotage Si-Thiol) are added thereto and the mixture is stirred for 6 h at ambient temperature and then filtered. The residue is washed with twice 2 ml of propan-1-ol and then the filtrate is evaporated. The crude compound is used as it is in the next stage.

5.4 {4-[2-(2-Fluorophenyl)imidazo[1,2-a]pyridin-6-yl]thiazol-2-yl}methanol

The crude compound obtained in 5.3 is dissolved in 5 ml of THF containing 0.5 mmol of tetrabutylammonium fluoride hydrate. The mixture is stirred for 16 h at ambient temperature, and the solvent is then evaporated off under reduced pressure. The compound is purified by chromatography. 4.1 mg of compound are obtained.

¹H NMR (DMSO-d6, δ in ppm): 4.82 (s, 2H); 6.19 (m, 1H); 7.31 (m, 2H); 7.38 (m, 1H); 7.67 (d, 1H); 7.84 (d, 1H); 8.08 (s, 1H); 8.38 (t, 1H); 8.45 (d, 1H); 9.22 (s, 1H).

EXAMPLE 6

2-{2-[2-(1H-Indol-6-yl)imidazo[1,2-a]pyridin-6-yl]pyridin-4-yl}propan-2-ol (Compound 152 of the Table)

6.1 N-Methoxy-N-methylindole-6-carboxamide

In a round-bottomed flask, 5.0 g of indole-6-carboxylic acid, 3.3 g of N,O-dimethylhydroxylamine hydrochloride, 11.9 g of 1-(3-dimethylaminopropyl)-3-ethylcarbodiimide and 10 ml of pyridine are placed in 150 ml of tetrahydrofuran. The mixture is stirred at ambient temperature for 40 h. The mixture is concentrated, and the residue is taken up in 150 ml of ethyl acetate and 50 ml of water. The organic phase is washed with 50 ml of a 1N solution of sodium hydroxide and 50 ml of a saturated solution of sodium chloride, dried over magnesium sulphate and then concentrated under reduced pressure. 6.8 g of compound are obtained.

$^1$H NMR (CDCl$_3$, δ in ppm): 3.3 (s, 3H); 3.5 (s, 3H); 6.45 (m, 1H); 7.25 (t, 1H); 7.4 (dd, 1H); 7.55 (d, 1H); 7.75 (s, 1H); 8.8 (s, 1H). M+H=205.

6.2 N-Methoxy-N-methyl-1-(phenylsulphonyl)indole-6-carboxamide

In a round-bottomed flask, 6.8 g of compound obtained in 6.1 are placed in 100 ml of N,N-dimethylformamide at 0° C. 1.45 g of NaH are added portionwise, followed by 6.52 g of benzenesulphonyl chloride. The mixture is stirred at ambient temperature for 40 h. 150 ml of water are added and the mixture is then extracted with 60 ml of ethyl acetate. The organic phase is washed with 50 ml of a saturated solution of sodium chloride, dried over magnesium sulphate and then concentrated under reduced pressure. The residue is purified by silica gel chromatography, elution being carried out with a heptane/ethyl acetate mixture. 9.5 g of compound are obtained.

$^1$H NMR (CDCl$_3$, δ in ppm): 3.4 (s, 3H); 3.55 (s, 3H); 6.7 (d, 1H); 7.45 to 7.6 (m, 5H); 7.7 (d, 1H); 7.95 (m, 2H); 8.4 (s, 1H). M+H=345.

6.3 6-acetyl-1-(phenylsulphonyl)indole

In a round-bottomed flask, 9.2 g of compound obtained in 6.2 are placed in 250 ml of tetrahydrofuran at 0° C. and under argon. 27 ml of methylmagnesium bromide (3M in diethyl ether) are added dropwise. The mixture is stirred for one hour at 0° C. and 20 h at ambient temperature. The mixture is cooled to 0° C. and 150 ml of water and 50 ml of a saturated solution of ammonium chloride are added. The mixture is extracted with 60 ml of ethyl acetate. The organic phase is washed with 40 ml of a saturated solution of sodium chloride, dried over magnesium sulphate and then concentrated under reduced pressure. 7.3 g of compound are obtained.

$^1$H NMR (CDCl$_3$, δ in ppm): 2.7 (s, 3H); 6.75 (d, 1H); 7.45 to 7.65 (m, 4H); 7.8 (d, 1H); 7.95 (m, 3H); 8.65 (s, 1H). M+H=300; Mp=160-163° C.

6.4 2-Bromo-1-[1-(phenylsulphonyl)indol-6-yl]ethanone

In a round-bottomed flask, 3 g of copper bromide are placed in 120 ml of ethyl acetate and the mixture is refluxed. 2 g of 6-acetyl-1-(phenylsulphonyl)indole are added. The mixture is stirred for 4 hours at reflux. The mixture is filtered through paper and then the filtrate is poured into 150 ml of a 20% solution of sodium thiosulphate. The mixture is extracted with 60 ml of ethyl acetate. The organic phase is washed with 40 ml of a saturated solution of sodium chloride, dried over magnesium sulphate and then concentrated under reduced pressure. 2.6 g of compound are obtained.

$^1$H NMR (CDCl$_3$, δ in ppm): 4.45 (s, 2H); 6.65 (d, 1H); 7.35 to 7.55 (m, 4H); 7.7 (d, 1H); 7.9 (m, 3H); 8.6 (s, 1H). M+H=378

6.5 2-(1-Phenylsulphonyl-1H-indol-6-yl)-6-(4,4,5,5-tetramethyl-[1,3,2]dioxaborolan-2-yl)imidazo[1,2-a]pyridine hydrobromide 1.6 g of 5-(4,4,5,5-tetramethyl-1,3,2-dioxaborolan-2-yl)pyridin-2-ylamine and 2.7 g of 2-bromo-1-[1-(phenylsulphonyl)indol-6-yl]ethanone are placed in 70 ml of ethanol and the mixture is refluxed for 20 h. A precipitate forms and is recovered by filtration, washed with diethyl ether and oven-dried under reduced pressure. 2.3 g of compound are obtained.

$^1$H NMR (DMSO-d6, δ in ppm): 1.4 (s, 12H); 6.95 (d, 1H); from 7.55 to 7.85 (m, 7H); 7.95 (d, 1H); 8.05 (m, 2H); 8.55 (s, 1H); 8.75 (s, 1H); 9.05 (s, 1H).

6.6 2-Bromo-N-methoxy-N-methylisonicotinamide

In a round-bottomed flask, 2.0 g of 2-bromoisonicotinic acid, 1.1 g of N,O-dimethylhydroxylamine hydrochloride, 3.8 g of 1-(3-dimethylaminopropyl)-3-ethylcarbodiimide and 3.2 ml of pyridine are placed in 50 ml of tetrahydrofuran. The mixture is stirred at ambient temperature for 40 h. The mixture is concentrated, and the residue is taken up in 50 ml of ethyl acetate and 50 ml of water. The organic phase is washed with 50 ml of a 1N solution of sodium hydroxide and 50 ml of a saturated solution of sodium chloride, dried over magnesium sulphate and then concentrated under reduced pressure. 2.0 g of compound are obtained.

$^1$H NMR (CDCl$_3$, δ in ppm): 3.3 (s, 3H); 3.5 (s, 3H); 7.4 (d, 1H); 7.65 (s, 1H); 8.4 (d, 1H). M+H=245.

6.7 2-Bromo-4-acetylpyridine

In a round-bottomed flask, 2.0 g of compound obtained in 6.6 are placed in 80 ml of tetrahydrofuran at 0° C. and under argon. 8 ml of methylmagnesium bromide (3M in ethyl ether) are added dropwise. The mixture is stirred for one hour at 0° C. and 20 h at ambient temperature. It is cooled to 0° C. and 80 ml of water and 40 ml of a saturated solution of ammonium chloride are added. The mixture is extracted with 40 ml of ethyl acetate. The organic phase is washed with 40 ml of a saturated solution of sodium chloride, dried over magnesium sulphate and then concentrated under reduced pressure. 1.6 g of compound are obtained.

$^1$H NMR (CDCl$_3$, δ in ppm): 2.55 (s, 3H); 7.6 (d, 1H); 7.85 (s, 1H); 8.5 (d, 1H). M+H=200.

6.8 2-(2-Bromopyridin-4-yl)propan-2-ol

In a round-bottomed flask, 1.1 g of compound obtained in 6.7 are placed in 60 ml of tetrahydrofuran at 0° C. and under argon. 13 ml of methylmagnesium bromide (3M in ethyl ether) are added dropwise. The mixture is stirred for one hour at 0° C. and 20 h at ambient temperature. It is cooled to 0° C. and 60 ml of water and 30 ml of a saturated solution of ammonium chloride are added. The mixture is extracted with 40 ml of ethyl acetate. The organic phase is washed with 40 ml of a saturated solution of sodium chloride, dried over magnesium sulphate and then concentrated under reduced pressure. 1.5 g of compound are obtained.

$^1$H NMR (CDCl$_3$, δ in ppm): 1.55 (s, 6H); 7.35 (d, 1H); 7.6 (s, 1H); 8.3 (d, 1H).

6.9 2-Bromo-4-[1-methyl-1-(trimethylsilanyloxy)ethyl]pyridine

In a round-bottomed flask, 1.5 g of 2-(2-bromo-pyridin-4-yl)propan-2-ol obtained in 6.8 are placed in 35 ml of dichloromethane at 0° C. 2.4 ml of triethylamine and 1.9 ml of trimethylsilane chloride are added. The mixture is stirred for one hour at 0° C. and 20 h at ambient temperature. 20 ml of water are added and the mixture is extracted with 20 ml of dichloromethane. The organic phase is washed with 20 ml of a saturated solution of sodium chloride, dried over magnesium sulphate and then concentrated under reduced pressure. The residue is purified by silica gel chromatography, elution being carried out with a dichloromethane/methanol mixture. 0.7 g of compound are obtained.

$^1$H NMR (CDCl$_3$, δ in ppm): 0 (s, 9H); 1.4 (s, 6H); 7.1 (d, 1H); 7.35 (s, 1H); 8.1 (d, 1H).

6.10 2-(1-Phenylsulphonyl-1H-indol-6-yl)-6-[4-[1-methyl-1-(trimethylsilanyloxy)ethyl]pyridin-2-yl]imidazo[1,2-a]pyridine 0.2 g of compound obtained in 6.9 in 4 ml of tetrahydrofuran and 1 ml of water are placed in a round-bottomed flask and degassed under an argon stream for 10 min. 0.4 g of hydrobromide of the compound obtained in 6.5, 45 mg of [1,1'-bis(diphenyl-phosphino)ferrocene]dichloropalladium and 0.9 g of caesium carbonate are added thereto and the mixture is heated at 80° C. for 4 hours. After cooling, the reaction mixture is concentrated under reduced pressure. The residue obtained is purified by silica gel chromatography, elution being carried out with a heptane/ethyl acetate mixture. 200 mg of compound are obtained.

$^1$H NMR (CDCl$_3$, δ in ppm): 0 (s, 9H); 1.4 (s, 6H); 6.45 (d, 1H); 7.1 (m, 1H); 7.2 to 7.4 (m, 5H); 7.55 (m, 3H); 7.7 to 7.85 (m, 4H); 8.35 (s, 1H); 8.4 (d, 1H); 8.75 (s, 1H). M+H=581.

6.11 2-{2-[2-(1H-Indol-6-yl)imidazo[1,2-a]pyridin-6-yl]pyridin-4-yl}propan-2-ol 0.2 g of the compound obtained in 6.10 in 4 ml of ethanol are placed in a round-bottomed flask and 1.7 ml of a 1N solution of sodium hydroxide are added. The mixture is stirred at 80° C. for 20 h. The reaction mixture is concentrated under reduced pressure and the residue obtained is purified by silica gel chromatography, elution being carried out with a dichloromethane/methanol mixture. 64 mg of compound are obtained.

$^1$H NMR (DMSO-d6, δ in ppm): 1.55 (s, 6H); 5.35 (s, 1H); 6.45 (s, 1H); 7.4 (t, 1H); 7.45 (d, 1H); 7.65 (m, 2H); 7.7 (d, 1H); 8.0 (d, 1H); 8.1 (m, 2H); 8.45 (s, 1H); 8.6 (d, 1H); 9.3 (s, 1H); 11.2 (s, 1H).

EXAMPLE 7

2-{2-[2-(1H-Indazol-3-yl)imidazo[1,2-a]pyridin-6-yl]pyridin-4-yl}propan-2-ol (Compound 153 of the Table)

7.1 4-[1-Methyl-1-(trimethylsilanyloxy)ethyl][2,3']bipyridinyl-6'-ylamine 0.5 g of the compound obtained in 6.9, 8 ml of tetrahydrofuran and 2 ml of water are placed in a round-bottomed flask and degassed under an argon stream for 10 min. 10.4 g of 5-(4,4,5,5-tetramethyl-1,3,2-dioxaborolan-2-yl)pyridin-2-ylamine, 110 mg of [1,1'-bis(diphenylphosphino)ferrocene]dichloropalladium and 1.1 g of caesium carbonate are added thereto and the mixture is heated at 80° C. for 4 hours. After cooling, the reaction mixture is concentrated under reduced pressure. The residue obtained is purified by silica gel chromatography, elution being carried out with a heptane/ethyl acetate mixture. 240 mg of compound are obtained.

$^1$H NMR (CDCl$_3$, δ in ppm): 0 (s, 9H); 1.4 (s, 6H); 4.4 (s, 2H); 6.45 (d, 1H); 7.05 (m, 1H); 7.55 (s, 1H); 7.95 (m, 1H); 8.4 (d, 1H); 8.5 (m, 1H). M+H=302.

7.2 N-Methoxy-N-methyl-1H-indazole-3-carboxamide

In a round-bottomed flask, 4.0 g of 1H-indazole-3-carboxylic acid, 2.6 g of N,O-dimethylhydroxylamine hydrochloride, 9.4 g of 1-(3-dimethylaminopropyl)-3-ethylcarbodiimide and 8.4 ml of pyridine are placed in 120 ml of tetrahydrofuran. The mixture is stirred at ambient temperature for 20 h. The mixture is concentrated and the residue is taken up in water. The yellow precipitate obtained is washed with water and then dried under reduced pressure. 3.5 g of compound are obtained.

$^1$H NMR (DMSO-d6, δ in ppm): 3.5 (s, 3H); 3.8 (s, 3H); 7.25 (m, 1H); 7.45 (m, 1H); 7.65 (d, 1H); 8.05 (d, 1H); 13.65 (s, 1H). M+H=206.

7.3 1-(1H-Indazol-3-yl)ethanone

In a round-bottomed flask, 2.4 g of N-methoxy-N-methyl-1H-indazole-3-carboxamide are placed in 140 ml of tetrahydrofuran at 0° C. and under argon. 19 ml of methylmagnesium bromide (3M in ethyl ether) are added dropwise. The mixture is stirred for one hour at 0° C. and 20 h at ambient temperature. It is cooled to 0° C. and 80 ml of water and 40 ml of a saturated solution of ammonium chloride are added. The mixture is extracted with 40 ml of ethyl acetate. The organic phase is washed with 40 ml of a saturated solution of sodium chloride, dried over magnesium sulphate and then concentrated under reduced pressure. The residue is purified by silica gel chromatography, elution being carried out with a heptane/ethyl acetate mixture. 1.6 g of compound are obtained.

$^1$H NMR (DMSO-d6, δ in ppm): 2.65 (s, 3H); 7.35 (m, 1H); 7.55 (m, 1H); 7.7 (d, 1H); 8.2 (d, 1H); 13.9 (s, 1H). M+H=161.

7.4 2-Bromo-1-(1H-indazol-3-yl)ethanone

In a round-bottomed flask, 4.5 g of copper bromide are placed in 180 ml of ethyl acetate and the mixture is refluxed. 1.6 of 1-(1H-indazol-3-yl)ethanone are added. The mixture is stirred for 4 hours at reflux. The resulting mixture is filtered through paper and the filtrate is poured into 150 ml of a 20% solution of sodium thiosulphate. The mixture is extracted with 60 ml of ethyl acetate. The organic phase is washed with 40 ml of a saturated solution of sodium chloride, dried over magnesium sulphate and then concentrated under reduced pressure. 2.4 g of compound are obtained.

$^1$H NMR (DMSO-d6, δ in ppm): 4.95 (s, 2H); from 7.35 to 7.55 (m, 2H); 7.75 (d, 1H); 8.2 (d, 1H); 14.1 (s, 1H). M+H=239.

7.5 3-(6-{4-[1-Methyl-1-(trimethylsilanyloxy)ethyl]pyridin-2-yl}imidazo[1,2-a]pyridin-2-yl)-1H-indazole In a 50 ml round-bottomed flask, 140 mg of the compound obtained in 7.1 and 110 mg of the compound obtained in 7.4 are introduced into 4 ml of ethanol. 40 mg of sodium bicarbonate are added and the mixture is heated at 80° C. for 4 h. The solvent is evaporated off under reduced pressure and the residue is purified by chromatography, elution being carried out with a dichloromethane/methanol mixture. 137 mg of compound are obtained.

¹H NMR (CDCl₃, δ in ppm): 0 (s, 9H); 1.45 (s, 6H); 7.15 (m, 2H); 7.2 to 7.35 (m, 2H); 7.6 (m, 3H); 8.1 (s, 1H); 8.35 (d, 1H); 8.45 (d, 1H); 9.85 (s, 1H); 10.2 (s, 1H). M+H=370.

7.6 2-{2-[2-(1H-Indazol-3-yl)imidazo[1,2-a]pyridin-6-yl]pyridin-4-yl}propan-2-ol 130 mg of the compound obtained in 7.5 are dissolved in 2 ml of THF, 90 mg of tetrabutylammonium fluoride hydrate are added thereto and the mixture is stirred for 2 hours at ambient temperature. The solvent is then evaporated off under reduced pressure and the residue is purified by chromatography, elution being carried out with a dichloromethane/methanol mixture. 99 mg of compound are obtained.

¹H NMR (DMSO-d6, δ in ppm): 1.5 (s, 6H); 5.35 (s, 1H); 7.25 (t, 1H); 7.4 (t, 1H); 7.45 (d, 1H); 7.6 (d, 1H); 7.75 (d, 1H); 8.05 (m, 2H); 8.5 (d, 1H); 8.55 (s, 1H); 8.65 (d, 1H); 9.4 (s, 1H); 13.15 (s, 1H); Mp=255-259° C.

The tables which follow illustrate the chemical structures of general formula (I) (Table 2) and the physicochemical characteristics (Table 3) of some examples of compounds according to the invention.

In these tables:

"Ph" means phenyl;
"Cl" means chlorine;
"F" means fluorine;
"Br" means bromine;
"Me" means methyl;
"MeO" means methoxy;
"(F₂CH)O" means difluoromethoxy;
the "Mp" column gives the melting points of the products in degrees Celsius (° C.) or, when the products have been isolated in the form of an amorphous solid or of an oil, they are characterized by their mass [M+H];
in the "salt/base" column, "-" represents a compound in free base form, whereas "HCl" represents a compound in hydrochloride form, and the ratio between parentheses is the (acid:base) ratio.

TABLE 2

| Ex | R₁ | R | (Het/R₂R₃R₄O-CH-X group) | salt |
|----|------|---|---|---|
| 1 | 4-Cl—Ph | H | HO-CH₂-furan-2-yl | — |
| 2 | 4-Cl—Ph | H | HO-CH₂-thiophen-2-yl (3-linked) | — |
| 3 | 4-Cl—Ph | H | HO-CH₂-thiophen-2-yl | — |
| 4 | 4-Cl—Ph | H | HO-CH₂-pyridin-4-yl | — |
| 5 | 4-Cl—Ph | H | HO-CH₂-pyridin-3-yl | — |
| 6 | 4-Cl—Ph | H | HO-CH₂-furan-2-yl | — |
| 7 | 4-Cl—Ph | H | HO-CH₂-pyridin-2-yl | — |

TABLE 2-continued
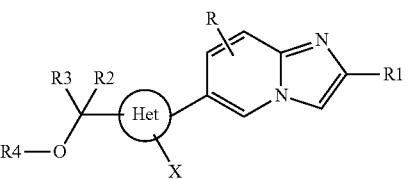
| Ex | R₁ | R | | salt |
|---|---|---|---|---|
| 8 | 4-Cl—Ph | H | 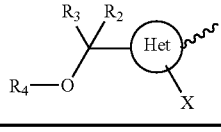 | — |
| 9 | 4-Cl—Ph | H | 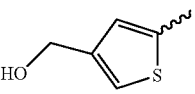 | — |
| 10 | 4-Cl—Ph | H | 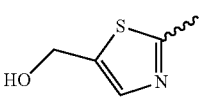 | — |
| 11 | 4-Cl—Ph | H | 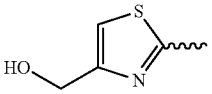 | — |
| 12 | 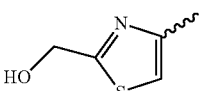 | H | 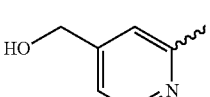 | HCl (1:1) |
| 13 |  | H | 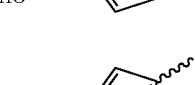 | HCl (2:1) |
| 14 | 4-Me—Ph | H | 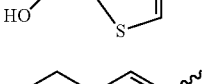 | — |
| 15 | 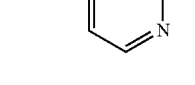 | H | 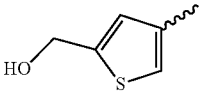 | HCl (3:2) |
| 16 | 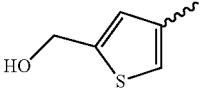 | H |  | HCl (2:1) |
| 17 |  | H |  | HCl (1:1) |
| 18 |  | H |  | HCl (1:1) |

TABLE 2-continued
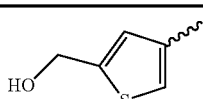
| Ex | R₁ | R | 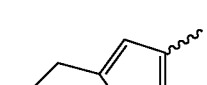 | salt |
|---|---|---|---|---|
| 19 | Ph | H | 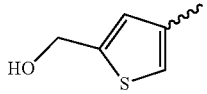 | HCl (1:1) |
| 20 | 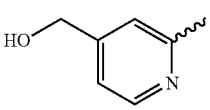 | H | 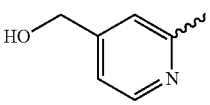 | HCl (1:1) |
| 21 | 3-MeO—Ph | H | 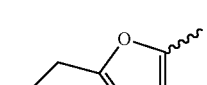 | HCl (1:1) |
| 22 | 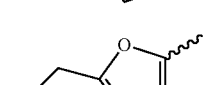 | H |  | HCl (1:1) |
| 23 | Ph | H | 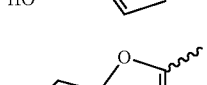 | — |
| 24 | 4-Me—Ph | H | 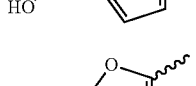 | HCl (1:1) |
| 25 | Ph | H | 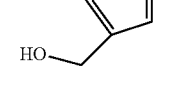 | — |
| 26 | 3-OMe—Ph | H |  | — |
| 27 | 2,4-diF—Ph | H |  | — |
| 28 | 4-Cl—Ph | H |  | — |
| 29 | 4-Cl—Ph | H |  | — |

TABLE 2-continued

| Ex | R₁ | R | (R₃R₂C(OR₄)–Het–X group) | salt |
|---|---|---|---|---|
| 30 | 4-(CH₂OH)—Ph | H | 5-(hydroxymethyl)furan-2-yl | — |
| 31 | 4-(CONMe₂)—Ph | H | 5-(hydroxymethyl)furan-2-yl | — |
| 32 | 1H-indol-6-yl | H | 5-(hydroxymethyl)furan-2-yl | — |
| 33 | 2-methoxypyridin-3-yl | H | 5-(hydroxymethyl)furan-2-yl | — |
| 34 | quinolin-5-yl | H | 5-(hydroxymethyl)furan-2-yl | — |
| 35 | 4-(N-morpholino)-Ph | H | 5-(hydroxymethyl)furan-2-yl | — |
| 36 | isoquinolin-5-yl | H | 5-(hydroxymethyl)furan-2-yl | — |
| 37 | 4-(1-(pyrrolidin-1-yl)ethyl)-Ph | H | 5-(hydroxymethyl)furan-2-yl | — |
| 38 | 4-(Me₂NCO)—Ph | H | 5-(hydroxymethyl)thiophen-2-yl | — |

TABLE 2-continued
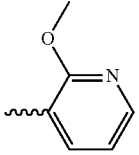
| Ex | R₁ | R | 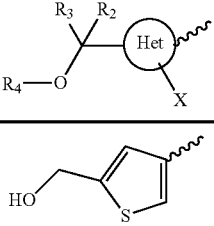 | salt |
|---|---|---|---|---|
| 39 | 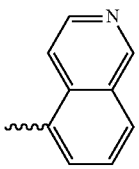 | H | 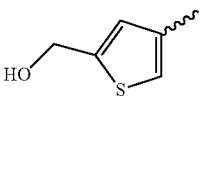 | — |
| 40 | 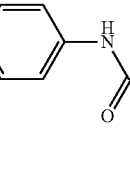 | H | 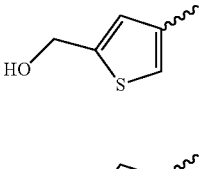 | — |
| 41 | 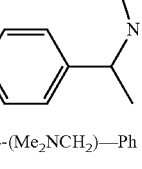 | H | 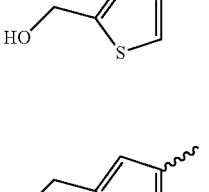 | — |
| 42 | 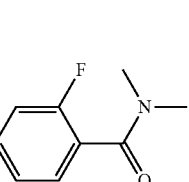 | H | 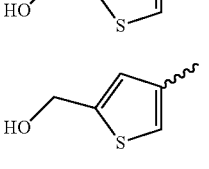 | — |
| 43 | 4-(Me₂NCH₂)—Ph | H | 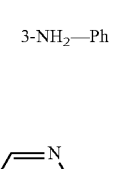 | — |
| 44 | 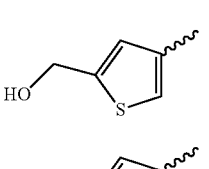 | H | 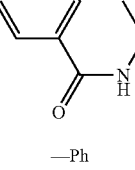 | — |
| 45 | 3-NH₂—Ph | H | 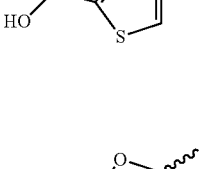 | — |
| 46 |  | H | 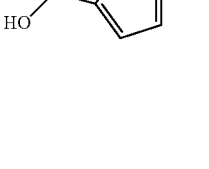 | — |
| 47 | —Ph | 3-Me |  | — |

TABLE 2-continued
| Ex | R₁ | R | 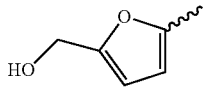 | salt |
|---|---|---|---|---|
| 48 | 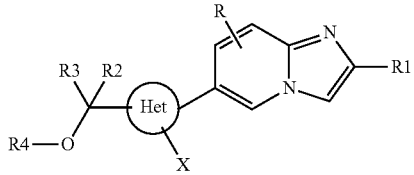 | 3-Me | 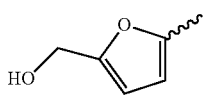 | — |
| 49 | 3-Cl—Ph | 3-Me | 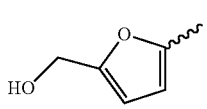 | — |
| 50 | 4-Pyrrolidino-Ph | H | 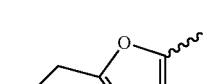 | — |
| 51 | 3-Cyano-Ph | H | 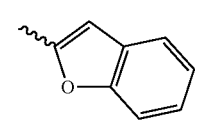 | — |
| 52 | 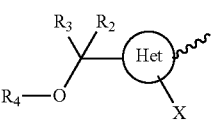 | H | 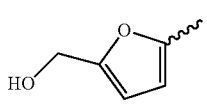 | — |
| 53 | 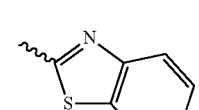 | H | 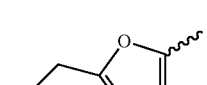 | — |
| 54 | 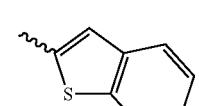 | H | 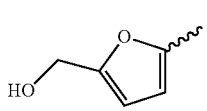 | — |
| 55 | 4-NO₂—Ph | H | 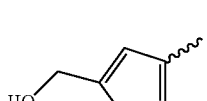 | — |
| 56 | 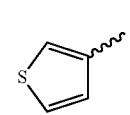 | H | 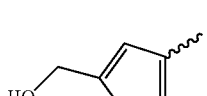 | — |
| 57 | 4-SMe—Ph | H | 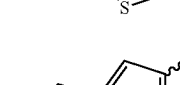 | — |
| 58 | 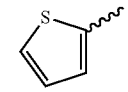 | H | 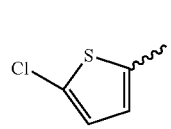 | — |
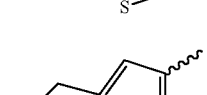

TABLE 2-continued

| Ex | R₁ | R | Het-X | salt |
|---|---|---|---|---|
| 59 | 4-MeSO₂—Ph | H | 2-(hydroxymethyl)thiophen-4-yl | — |
| 60 | benzothiophen-2-yl | H | 2-(hydroxymethyl)thiophen-4-yl | — |
| 61 | benzothiophen-5-yl | H | 2-(hydroxymethyl)thiophen-4-yl | — |
| 62 | Ph | 3-Me | 2-(hydroxymethyl)thiazol-4-yl | — |
| 63 | thiophen-2-yl | 3-Me | 2-(hydroxymethyl)thiazol-4-yl | — |
| 64 | 4-OMe—Ph | 3-Me | 2-(hydroxymethyl)thiazol-4-yl | — |
| 65 | 4-Pyrrolidino-Ph | H | 2-(hydroxymethyl)thiazol-4-yl | — |
| 66 | 2-F—Ph | H | 2-(hydroxymethyl)thiazol-4-yl | — |
| 67 | 4-MeSO₂—Ph | H | 2-(hydroxymethyl)thiazol-4-yl | — |
| 68 | benzofuran-2-yl | H | 2-(hydroxymethyl)thiazol-4-yl | — |
| 69 | benzothiophen-2-yl | H | 2-(hydroxymethyl)thiazol-4-yl | — |

TABLE 2-continued

| Ex | R₁ | R | X | salt |
|----|----|----|----|------|
| 70 | 2-furyl | H | 2-(hydroxymethyl)thiazol-4-yl | — |
| 71 | benzothiophen-5-yl | H | 2-(hydroxymethyl)thiazol-4-yl | — |
| 72 | 4-Pyrrolidino-Ph | H | 5-(hydroxymethyl)thiophen-2-yl | — |
| 73 | 4-Cl—Ph | H | 5-(1-hydroxyethyl)thiophen-2-yl | — |
| 74 | 4-Cl—Ph | H | 5-(2-hydroxypropan-2-yl)thiophen-2-yl | — |
| 75 | 4-OMe—Ph | 3-Me | 5-(hydroxymethyl)furan-2-yl | — |
| 76 | 4-CF3—Ph | H | 5-(hydroxymethyl)furan-2-yl | — |
| 77 | 4-OMe—Ph | H | 5-(hydroxymethyl)furan-2-yl | — |
| 78 | 4-F—Ph | H | 5-(hydroxymethyl)furan-2-yl | — |
| 79 | 3,4-diF—Ph | H | 5-(hydroxymethyl)furan-2-yl | — |
| 80 | thiophen-3-yl | H | 5-(hydroxymethyl)furan-2-yl | — |
| 81 | 5-Cl-thiophen-2-yl | H | 5-(hydroxymethyl)furan-2-yl | — |

TABLE 2-continued
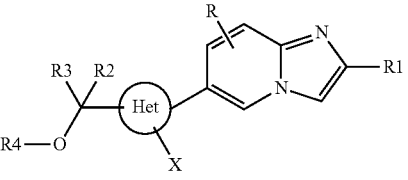
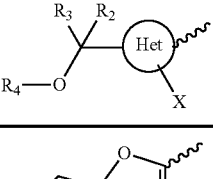
| Ex | R₁ | R | 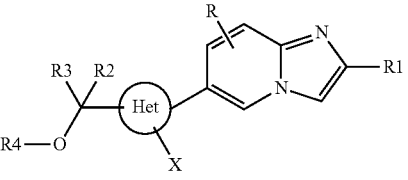 | salt |
|----|-----|---|---|------|
| 82 | 2-F—Ph | H | 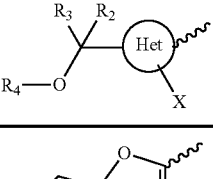 | — |
| 83 | 3-Br—Ph | H | 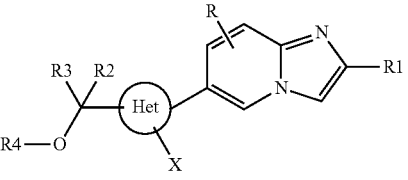 | — |
| 84 | 3-Me-4-Cl—Ph | H | 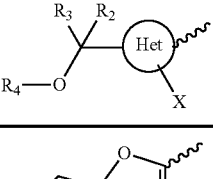 | — |
| 85 | 4-MeSO₂—Ph | H | 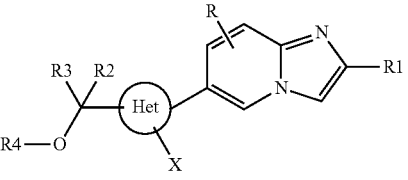 | — |
| 86 | 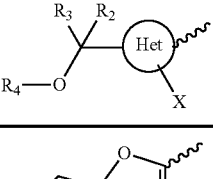 | H | 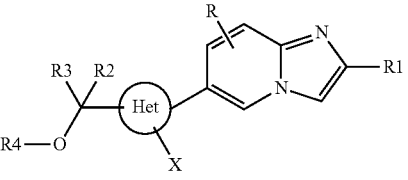 | — |
| 87 | 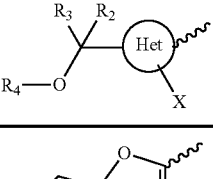 | H | 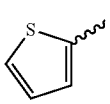 | — |
| 88 | 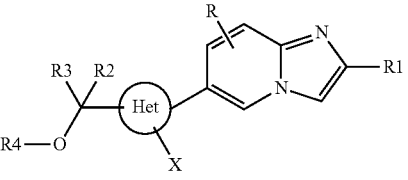 | H | 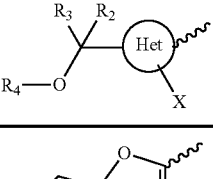 | — |
| 89 | 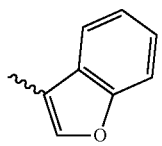 | H | 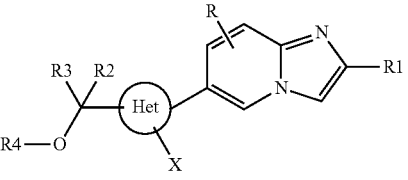 | — |
| 90 | 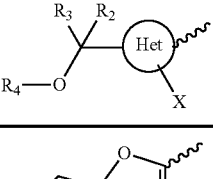 | H | 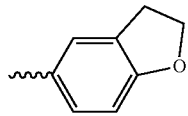 | — |
| 91 | 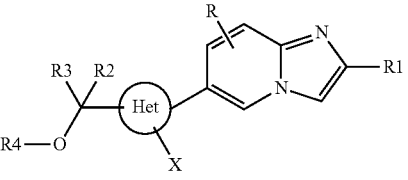 | H | 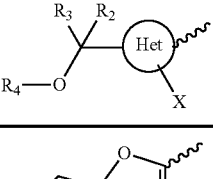 | — |
| 92 | 4-SMe—Ph | H | 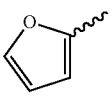 | — |

TABLE 2-continued
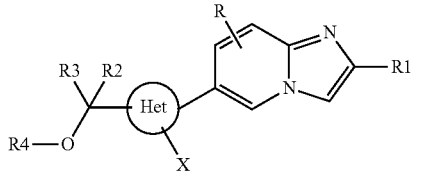
| Ex | R₁ | R | X | salt |
|---|---|---|---|---|
| 93 | 4-Cl—Ph | 3-Me | 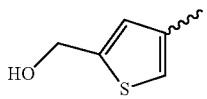 | — |
| 94 | 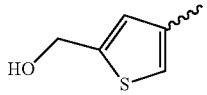 | 3-Me | 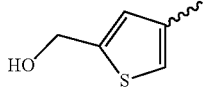 | — |
| 95 | 3-Cl—Ph | 3-Me | 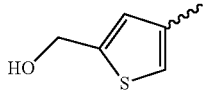 | — |
| 96 | 2,4-diF—Ph | 3-Me | 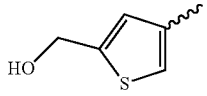 | — |
| 97 | 4-F—Ph | H | 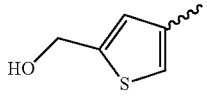 | — |
| 98 | 3,4-diF—Ph | H | 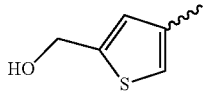 | — |
| 99 | 3-Cyano-Ph | H | 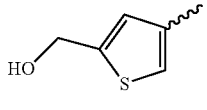 | — |
| 100 | 2-F—Ph | H | 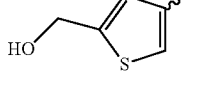 | — |
| 101 | 3-Br | H | 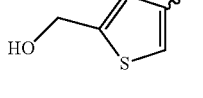 | — |
| 102 | 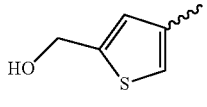 | H |  | — |
| 103 |  | H |  | — |

TABLE 2-continued

Structure (general):
- Imidazo[1,2-a]pyridine core with R at position (on pyridine ring), R1 at 2-position, and 6-position linked to Het(X) bearing C(R2)(R3)(OR4)
- Second depicted fragment: R4—O—C(R3)(R2)—Het—X (the "Het—X" group shown in the X column)

| Ex | R₁ | R | X | salt |
|---|---|---|---|---|
| 104 | benzofuran-3-yl | H | 2-(hydroxymethyl)thiophen-4-yl (HOCH₂-thiophene) | — |
| 105 | 1-methylbenzimidazol-2-yl | H | 2-(hydroxymethyl)thiophen-4-yl | — |
| 106 | 2,3-dihydrobenzofuran-5-yl | H | 2-(hydroxymethyl)thiophen-4-yl | — |
| 107 | furan-2-yl | H | 2-(hydroxymethyl)thiophen-4-yl | — |
| 108 | benzofuran-5-yl | H | 2-(hydroxymethyl)thiophen-4-yl | — |
| 109 | thiazol-2-yl | H | 2-(hydroxymethyl)thiophen-4-yl | — |
| 110 | 4-Cl—Ph | 3-Me | 2-(hydroxymethyl)thiazol-4-yl | — |
| 111 | 3-Cl—Ph | 3-Me | 2-(hydroxymethyl)thiazol-4-yl | — |
| 112 | 4-CF3—Ph | H | 2-(hydroxymethyl)thiazol-4-yl | — |
| 113 | 4-F—Ph | H | 2-(hydroxymethyl)thiazol-4-yl | — |
| 114 | 3,4-diF—Ph | H | 2-(hydroxymethyl)thiazol-4-yl | — |

TABLE 2-continued

[Structure: imidazo[1,2-a]pyridine core with R at position on pyridine ring, R1 at position 2, and a substituent at position 6 comprising -C(R2)(R3)(OR4)-Het-X]

[Fragment notation for R1/Het/X portions in table: R4O-C(R3)(R2)-Het-X]

| Ex | R₁ | R | —Het—X | salt |
|---|---|---|---|---|
| 115 | 3-thienyl | H | 2-(hydroxymethyl)thiazol-4-yl | — |
| 116 | 2-pyridyl | H | 2-(hydroxymethyl)thiazol-4-yl | — |
| 117 | 5-Cl-2-thienyl | H | 2-(hydroxymethyl)thiazol-4-yl | — |
| 118 | 3-Br—Ph | H | 2-(hydroxymethyl)thiazol-4-yl | — |
| 119 | 4-Cl-3-Me—Ph | H | 2-(hydroxymethyl)thiazol-4-yl | — |
| 120 | 2-thienyl | H | 2-(hydroxymethyl)thiazol-4-yl | — |
| 121 | 3-benzofuryl | H | 2-(hydroxymethyl)thiazol-4-yl | — |
| 122 | 2,3-dihydrobenzofuran-5-yl | H | 2-(hydroxymethyl)thiazol-4-yl | — |
| 123 | benzofuran-5-yl | H | 2-(hydroxymethyl)thiazol-4-yl | — |
| 124 | 2-thiazolyl | H | 2-(hydroxymethyl)thiazol-4-yl | — |
| 125 | 3-(CH₂OH)—Ph | H | 5-(hydroxymethyl)furan-2-yl | — |

TABLE 2-continued

| Ex | R₁ | R | R4—O group / X | salt |
|---|---|---|---|---|
| 126 | 3-(NHC(O)CH(CH₃)₂)-Ph | H | 5-(HOCH₂)-furan-2-yl | — |
| 127 | 4-(N(CH₃)₂C(O))-3-F-Ph | H | 5-(HOCH₂)-furan-2-yl | — |
| 128 | 1H-indol-6-yl | H | 2-(C(CH₃)₂OH)-thiophen-4-yl | — |
| 129 | 3-(NHC(O)CH₃)-Ph | H | 2-(HOCH₂)-thiazol-4-yl | — |
| 130 | 4-(CH₂OH)—Ph | H | 2-(HOCH₂)-thiazol-4-yl | — |
| 131 | 3-(CH₂OH)—Ph | H | 2-(HOCH₂)-thiazol-4-yl | — |
| 132 | 1H-indol-5-yl | H | 2-(HOCH₂)-thiazol-4-yl | — |
| 133 | 4-methyl-thiophen-2-yl | H | 2-(HOCH₂)-thiazol-4-yl | — |
| 134 | 1H-indol-4-yl | H | 2-(HOCH₂)-thiazol-4-yl | — |

TABLE 2-continued
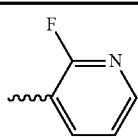
| Ex | R₁ | R | 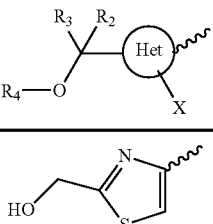 | salt |
|---|---|---|---|---|
| 135 | 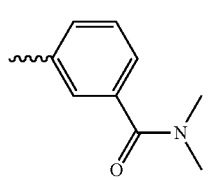 | H | 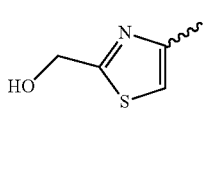 | — |
| 136 | 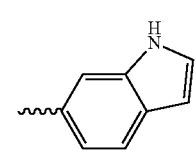 | H | 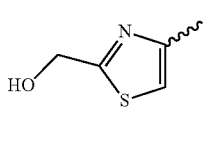 | — |
| 137 | 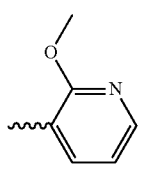 | H | 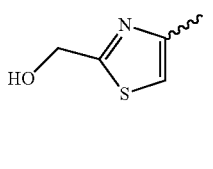 | — |
| 138 | 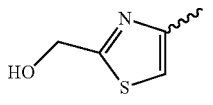 | H | 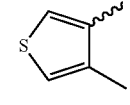 | — |
| 139 | 4-(CONHMe)—Ph | H | 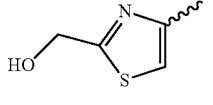 | — |
| 140 | 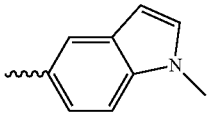 | H | 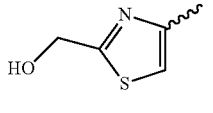 | — |
| 141 | 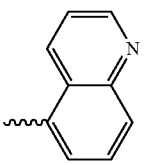 | H | | — |
| 142 | 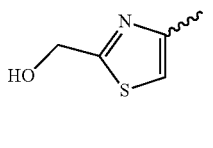 | H | | — |
| 143 | 4-(MeCONH)—Ph | H | 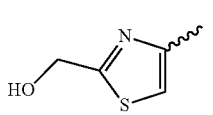 | — |

TABLE 2-continued

| Ex | R₁ | R | [Het-X group] | salt |
|---|---|---|---|---|
| 144 | 4-(N-Morpholino)-Ph | H | 2-(hydroxymethyl)thiazol-4-yl | — |
| 145 | isoquinolin-5-yl | H | 2-(hydroxymethyl)thiazol-4-yl | — |
| 146 | 3-(isobutyramido)-Ph | H | 2-(hydroxymethyl)thiazol-4-yl | — |
| 147 | 3-(Me₂NSO₂)—Ph | H | 2-(hydroxymethyl)thiazol-4-yl | — |
| 148 | 2,6-difluoropyridin-4-yl | H | 2-(hydroxymethyl)thiazol-4-yl | — |
| 149 | 1-isopentyl-1H-pyrazol-4-yl | H | 2-(hydroxymethyl)thiazol-4-yl | — |
| 150 | 1H-indol-6-yl | H | 3-(2-hydroxypropan-2-yl)-1H-pyrazol-4-yl | — |
| 151 | 1H-indol-6-yl | H | 5-fluoro-4-(2-hydroxypropan-2-yl)pyridin-2-yl | — |

TABLE 2-continued

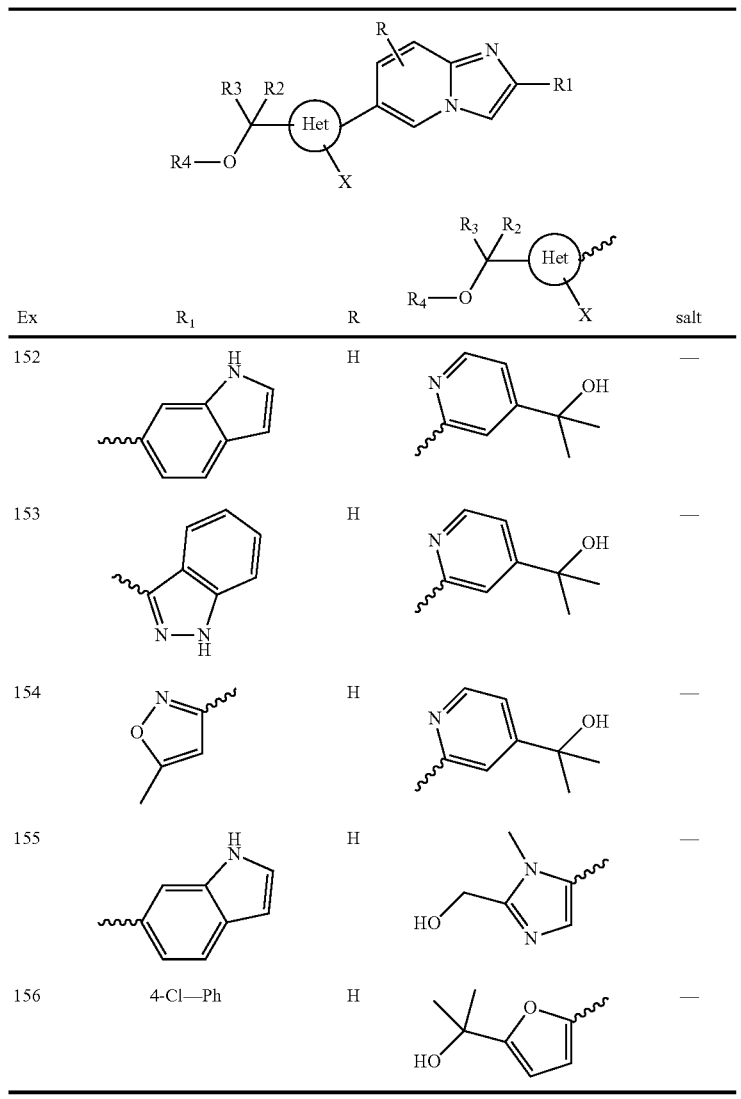

| Ex | R₁ | R | Het/X group | salt |
|---|---|---|---|---|
| 152 | 1H-indol-6-yl | H | 4-(2-hydroxypropan-2-yl)pyridin-2-yl | — |
| 153 | 1H-indazol-6-yl | H | 4-(2-hydroxypropan-2-yl)pyridin-2-yl | — |
| 154 | 5-methylisoxazol-3-yl | H | 4-(2-hydroxypropan-2-yl)pyridin-2-yl | — |
| 155 | 1H-indol-6-yl | H | 2-(hydroxymethyl)-1-methyl-1H-imidazol-5-yl | — |
| 156 | 4-Cl—Ph | H | 5-(2-hydroxypropan-2-yl)furan-2-yl | — |

TABLE 3

| Ex | Mp or [M + H] | ¹H NMR spectrum (DMSO-d6, δ in ppm) |
|---|---|---|
| 1 | 197-199 | 4.5 (d, 2H); 5.3 (t, 1H); 6.5 (m, 1H); 7.95 (m, 1H); 7.55 (m, 2H); from 7.60 to 7.70 (m, 2H); 8 (m, 2H); 8.5 (s, 1H); 8.85 (s, 1H). |
| 2 | 190-192° C. | 4.7 (d, 2H); 5.55 (t, 1H); 7.45 (s, 1H); 7.55 (d, 2H); from 7.60 to 7.70 (m, 2H); 7.85 (s, 1H); 8.05 (d, 2H); 8.4 (s, 1H); 8.95 (s, 1H). |
| 3 | 227-228° C. | 4.65 (d, 2H); 5.55 (t, 1H); 7.0 (d, 1H); 7.40 (d, 1H); from 7.50 to 7.70 (m, 4H); 8.0 (d, 2H); 8.45 (s, 1H); 8.85 (s, 1H). |
| 4 | 207.7-208.4 | 4.65 (d, 2H); 5.5 (t, 1H); 7.35 (d, 1H); 7.55 (d, 2H); 7.70 (d, 1H); 7.95 (s, 1H); from 8.0 to 8.10 (m, 3H); 8.55 (s, 1H); 8.65 (d, 1H); 9.35 (s, 1H). |
| 5 | 238.4-239.5 | 4.65 (d, 2H); 5.4 (t, 1H); 7.55 (d, 2H); from 7.65 to 7.75 (m, 2H); from 8.0 to 8.1 (m, 3H); 8.55 (s, 1H); 8.6 (s, 1H); 8.9 (s, 1H); 9.0 (s, 1H). |
| 6 | 194.7-195.2 | 4.4 (d, 2H); 5.3 (t, 1H); 6.8 (s, 1H); from 7.45 to 7.65 (m, 4H); 8.0 (d, 2H); 8.15 (s, 1H); 8.35 (s, 1H); 8.75 (s, 1H). |
| 7 | 197.4-198.2 | 4.7 (d, 2H); 5.5 (t, 1H); 7.5 (d, 1H); 7.55 (d, 2H); 7.7 (d, 1H); 7.9 (d, 1H); 7.95 (t, 1H); from 8.0 to 8.10 (m, 3H); 8.6 (s, 1H); 9.3 (s, 1H). |
| 8 | 211.3-211.9 | 4.5 (d, 2H); 5.2 (t, 1H); 7.35 (s, 1H); 7.5 (s, 1H); 7.55 (d, 2H); 7.6 (d, 1H); 7.65 (d, 1H); 8.0 (d, 2H); 8.45 (s, 1H); 8.9 (s, 1H). |
| 9 | 229-231 | 4.75 (d, 2H); 5.65 (t, 1H); 7.52 (2d, 2H); from 7.7 to 7.8 (m, 3H); 8.0 (d, 2H); 8.52 (s, 1H); 9.22 (s, 1H). |
| 10 | 193-194 | 4.65 (d, 2H); 5.4 (t, 1H); 7.5 (m, 3H); 7.7 (m, 2H); 8.0 (d, 2H); 8.55 (s, 1H); 9.3 (s, 1H). |

TABLE 3-continued

| Ex | Mp or [M + H] | ¹H NMR spectrum (DMSO-d6, δ in ppm) |
|---|---|---|
| 11 | 190-192 | 4.85 (s, 2H); 6.2 (t, 1H), from 7.50 to 7.60 (m, 2H); 7.7 (d, 1H); 7.85 (d, 1H); from 7.95 to 8.05 (m, 2H); 8.1 (s, 1H); 8.5 (s, 1H); 9.1 (s, 1H). |
| 12 | 268-273 | 4.7 (s, 2H); 7.2 (s, 1H); 7.5 (s, 1H); from 7.9 to 8.1 (m, 3H); from 8.5 to 8.6 (m, 3H); 8.7 (s, 1H); 9.65 (s, 1H). |
| 13 | 310-315 | 4.55 (s, 2H); 6.55 (s, 1H); 7.15 (s, 1H); 7.85 (m, 1H); 7.95 (m, 2H); 8.1 (m, 1H); 8.2 (m, 2H); 8.95 (s, 1H); 9.15 (s, 1H); 9.25 (s, 1H); 9.62 (s, 1H). |
| 14 | 197.5-198 | 2.35 (s, 3H); 4.7 (d, 2H); 5.55 (t, 1H); 7.25 (d, 2H); 7.45 (s, 1H); 7.6 (m, 2H); 7.8 (s, 1H); 7.87 (d, 2H); 8.3 (s, 1H); 8.9 (s, 1H). |
| 15 | 255-260 | 4.73 (s, 2H); 7.5 (d, 1H); 7.8 (t, 1H); 7.93 (t, 1H); 8.0 (d, 1H); 8.1 (s, 1H); 8.2 (m, 2H); 8.4 (d, 1H); 8.72 (d, 1H); 9.0 (s, 1H); 9.2 (s, 1H); 9.58 (s, 1H); 9.63 (s, 1H). |
| 16 | 310-315 | 4.75 (s, 2H); 7.55 (s, 1H); 7.8 (t, 1H); from 7.9 to 8.0 (m, 2H); 8.05 (s, 1H); from 8.17 to 8.25 (m, 3H); 8.9 (s, 1H); 9.328 (s, 1H); 9.32 (s, 1H); 9.67 (s, 1H). |
| 17 | 390-395 | 4.75 (s, 2H); 6.6 (s, 1H); 7.5 (m, 2H); 7.6 (d, 1H); 7.75 (d, 1H); 7.95 (d, 1H); 8.05 (s, 1H); 8.25 (m, 2H); 8.6 (s, 1H); 9.25 (s, 1H); 11.45 (s, 1H). |
| 18 | 390-395 | 4.55 (s, 2H); 6.55 (s, 1H); 6.6 (s, 1H); 7.15 (m, 1H); 7.5 (m, 1H); 7.6 (d, 1H); 7.7 (d, 1H); 7.95 (d, 1H); 8.15 (d, 1H); 8.25 (s, 1H); 8.65 (s, 1H); 9.1 (s, 1H); 11.45 (s, 1H). |
| 19 | 267 | 4.75 (s, 2H); from 7.5 to 7.6 (m, 2H); 7.65 (m, 2H); 8.0 (m, 2H); 8.1 (d, 2H); 8.3 (d, 1H); 8.7 (s, 1H); 9.3 (s, 1H). |
| 20 | 405-410 | 4.75 (s, 2H); 6.65 (m, 1H); 7.55 (s, 1H); 7.65 (m, 1H); 7.95 (d, 1H); 8.05 (s, 1H); 8.25 (d, 1H); 8.6 (s, 1H); 8.7 (s, 1H); 8.9 (s, 1H); 9.25 (s, 1H); 12.05 (s, 1H). |
| 21 | 305 | 3.9 (s, 3H); 4.7 (s, 2H); 7.1 (d, 1H); 7.55 (m, 2H); 7.65 (d, 1H); 7.7 (s, 1H); 7.95 (d, 1H); 8.0 (s, 1H); 8.25 (d, 1H); 8.7 (s, 1H); 9.2 (s, 1H). |
| 22 | 305-310 | 4.7 (s, 2H); 6.65 (m, 1H); 7.5 (m, 1H); 7.65 (m, 1H); 8.05 (s, 1H); 8.1 (s, 1H); 8.6 (d, 1H); 8.65 (d, 1H); 8.7 (d, 1H); 8.85 (s, 1H); 8.9 (s, 1H); 9.65 (s, 1H); 12.1 (s, 1H). |
| 23 | 225-226 | 4.65 (d, 2H); 5.55 (t, 1H); 7.35 (m, 2H); 7.5 (m, 2H); 7.7 (d, 1H); from 7.95 to 8.05 (m, 4H); 8.5 (s, 1H); 8.65 (d, 1H); 9.35 (s, 1H). |
| 24 | 248-254 | 2.4 (s, 3H); 4.5 (s, 2H); 6.55 (d, 1H); 7.15 (d, 1H); 7.45 (s, 1H); 7.6 (d, 2H); from 7.85 to 8.0 (m, 3H); 8.15 (d, 1H); 8.7 (s, 1H); 9.1 (s, 1H). |
| 25 | 202-204 | 4.5 (s, 2H); 5.3 (m, 1H); 6.45 (d, 1H); 6.95 (d, 1H); 7.35 (m, 1H); 7.5 (m, 2H); 7.65 (m, 2H); 7.95 (d, 1H); 8.5 (s, 1H); 8.9 (s, 1H). |
| 26 | 172-174 | 3.85 (s, 3H); 4.5 (s, 2H); 5.3 (s, 1H); 6.45 (d, 1H); 6.95 (m, 2H); 7.4 (m, 1H); 7.55 (m, 2H); 7.65 (m, 2H); 8.5 (s, 1H); 8.85 (s, 1H). |
| 27 | 207-208 | 4.5 (d, 2H); 5.3 (t, 1H); 6.5 (s, 1H); 6.95 (d, 1H); 7.25 (m, 1H); 7.4 (m, 1H); 7.65 (m, 2H); 8.3 (m, 1H); 8.45 (s, 1H); 8.95 (s, 1H). |
| 28 | 174-176 | 4.45 (d, 2H); 5.05 (t, 1H); 7.00 (s, 1H); from 7.55 (d, 2H); from 7.6 to 7.7 (m, 3H); 8.0 (d, 2H); 8.45 (s, 1H); 8.85 (s, 1H). |
| 29 | 176-178 | 3.3 (s, 3H); 4.3 (s, 2H); 7.0 (s, 1H); 7.5 (d, 2H); from 7.65 to 7.8 (m, 3H); 8.0 (d, 2H); 8.45 (s, 1H); 8.9 (s, 1H). |
| 30 | [321] | 4.47 (d, 2H); 4.55 (d, 2H); 5.2 (t, 1H); 5.31 (t, 1H); 6.42 (s, 1H); 6.91 (s, 1H); 7.4 (m, 2H); 7.6 (m, 2H); 7.91 (m, 2H); 8.41 (s, 1H); 8.82 (s, 1H). |
| 31 | [362] | 3 (m, 6H); 4.49 (m, 2H); 5.3 (m, 1H); 6.42 (s, 1H); 6.92 (s, 1H); 7.5 (m, 2H); 7.62 (m, 2H); 8 (m, 2H); 8.51 (s, 1H); 8.75 (s, 1H). |
| 32 | [330] | 4.45 (m, 2H); 5.3 (m, 1H); 6.45 (m, 2H); 6.9 (s, 1H); 7.4 (m, 1H); 7.55 to 7.65 (m, 4H); 8 (s, 1H); 8.4 (s, 1H); 8.85 (s, 1H); 11.2 (s, 1H). |
| 33 | [322] | 4.08 (s, 3H); 4.49 (m, 2H); 5.3 (m, 1H); 6.42 (s, 1H); 6.9 (d, 1H); 7.12 (m, 1H); 7.6 (m, 2H); 8.26 (m, 1H); 8.55 (m, 2H); 8.95 (s, 1H). |
| 34 | [342] | 4.5 (d, 2H); 5.32 (t, 1H); 6.49 (s, 1H); 6.94 (s, 1H); 7.6 (m, 1H); 7.68 (d, 1H); 7.76 (d, 1H); 7.83 (m, 1H); 7.95 (d, 1H); 8.07 (d, 1H); 8.5 (s, 1H); 8.92 (m, 2H); 9.31 (d, 1H). |
| 35 | [376] | 3.15 (m, 4H); 3.75 (m, 4H); 4.49 (m, 2H); 5.3 (m, 1H); 6.42 (d, 1H); 6.9 (d, 1H); 7 (m, 2H); 7.56 (m, 2H); 7.8 (m, 2H); 8.3 (s, 1H); 9.89 (s, 1H). |
| 36 | [342] | 4.5 (d, 2H); 5.32 (t, 1H); 6.49 (s, 1H); 6.99 (s, 1H); 7.69 (m, 1H); 7.73 (m, 2H); 8.18 (m, 2H); 8.51 (s, 1H); 8.58 (d, 1H); 8.29 (d, 1H); 8.94 (s, 1H); 9.4 (s, 1H). |
| 37 | [388] | 1.3 (d, 3H); 1.7 (m, 4H); 2.3 (m, 2H); 2.5 (m, 2H); 3.2 (q, 1H), 4.5 (d, 2H); 5.3 (t, 1H); 6.45 (d, 1H); 6.9 (d, 1H); 7.4 (m, 2H); 7.6 (m, 2H); 7.9 (m, 2H); 8.4 (s, 1H); 8.8 (s, 1H) |
| 38 | [378] | 3 (m, 6H); 4.7 (m, 2H); 5.59 (m, 1H); 7.42 (m, 1H); 7.5 (m, 2H); 7.65 (m, 2H); 7.81 (s, 1H); 8.01 (m, 2H); 8.41 (s, 1H); 8.91 (s, 1H). |
| 39 | [338] | 4.08 (s, 3H); 4.69 (s, 2H); 5.58 (m, 1H); 7.15 (m, 1H); 7.4 (m, 1H); 7.62 (m, 2H); 7.8 (s, 1H); 8.16 (m, 1H); 8.41 (s, 1H); 8.59 (d, 1H); 9.01 (s, 1H). |
| 40 | [358] | 4.7 (d, 2H); 5.59 (t, 1H); 7.44 (m, 1H); 7.75 (m, 3H); 7.85 (s, 1H); 8.15 (m, 2H); 8.4 (s, 1H); 8.58 (d, 1H); 8.9 (d, 1H); 9 (s, 1H); 9.39 (s, 1H). |

TABLE 3-continued

| Ex | Mp or [M + H] | $^1$H NMR spectrum (DMSO-d6, δ in ppm) |
|---|---|---|
| 41 | [392] | 1.11 (d, 6H); 2.51 (m, 1H); 4.68 (m, 2H); 5.57 (m, 1H); 7.33 (m, 1H); 7.41 (s, 1H); 7.6 (m, 4H); 7.8 (s, 1H); 8.29 (s, 2H); 8.9 (s, 1H); 9.9 (s, 1H). |
| 42 | [404] | 1.3 (d, 3H); 1.7 (m, 4H); 2.3 (m, 2H); 2.5 (m, 2H); 3.2 (q, 1H), 4.7 (d, 2H); 5.55 (t, 1H); 7.4 (m, 3H); 7.6 (m, 2H); 7.8 (s, 1H); 7.9 (d, 2H); 8.3 (s, 1H); 8.9 (s, 1H) |
| 43 | [364] | 2.18 (s, 6H); 3.4 (s, 2H); 4.68 (d, 2H); 5.58 (t, 1H); 7.32 (d, 2H); 7.41 (s, 1H); 7.6 (m, 2H); 7.71 (s, 1H); 7.92 (m, 2H); 8.31 (s, 1H); 8.9 (s, 1H). |
| 44 | [396] | 2.9 (s, 3H); 3.2 (s, 3H); 4.68 (m, 2H); 5.56 (m, 1H); 7.43 (m, 2H); 7.64 (m, 2H); 7.83 (s, 1H); 7.89 (m, 2H); 8.47 (s, 1H); 8.91 (s, 1H). |
| 45 | [322] | 4.68 (m, 2H); 5.11 (m, 2H); 5.55 (m, 1H); 6.5 (d, 1H); 7.05 (m, 2H); 7.22 (s, 1H); 7.41 (s, 1H); 7.59 (m, 1H); 7.8 (s, 1H); 8.18 (s, 1H); 8.9 (s, 1H). |
| 46 | [407] | 1.42 (s, 9H); 4.69 (m, 2H); 5.08 (m, 1H); 7.45 (s, 1H); 7.68 (m, 2H); 7.85 (s, 1H); 8.17 (s, 1H); 8.52 (s, 1H); 8.61 (m, 1H); 8.86 (s, 1H); 8.95 (s, 1H); 9.27 (s, 1H). |
| 47 | [305] | 2.71 (s, 3H); 4.5 (d, 2H); 5.32 (t, 1H); 6.44 (d, 1H); 6.99 (d, 1H); 7.35 (m, 1H); 7.48 (m, 2H); 7.63 (m, 2H); 7.8 (d, 2H); 8.49 (s, 1H). |
| 48 | [311] | 2.73 (s, 3H); 4.49 (d, 2H); 5.31 (t, 1H); 6.44 (d, 1H); 6.97 (d, 1H); 7.18 (m, 1H); 7.48 (m, 1H); 7.55 (m, 1H); 7.6 (m, 2H); 8.46 (s, 1H). |
| 49 | [339] | 2.72 (s, 3H); 4.49 (m, 2H); 5.31 (m, 1H); 6.44 (d, 1H); 6.99 (d, 1H); 7.41 (m, 1H); 7.51 (m, 1H); 7.65 (m, 2H); 7.77 (m, 1H); 7.82 (m, 1H); 8.5 (s, 1H). |
| 50 | [360] | 2 (m, 4H); 3.29 (m, 4H); 4.48 (d, 2H); 5.29 (t, 1H); 6.41 (d, 1H); 6.61 (m, 2H); 6.88 (d, 1H); 7.53 (m, 2H); 7.75 (m, 2H); 8.2 (s, 1H); 8.76 (s, 1H). |
| 51 | [316] | 4.48 (d, 2H); 5.31 (t, 1H); 6.45 (d, 1H); 6.95 (d, 1H); 7.65 (m, 3H); 7.77 (m, 1H); 8.29 (m, 1H); 8.37 (m, 1H); 8.51 (s, 1H); 8.85 (s, 1H). |
| 52 | [331] | 4.49 (m, 2H); 5.33 (m, 1H); 6.49 (d, 1H); 6.96 (d, 1H); 7.3 (m, 3H); 7.65 (m, 4H); 8.49 (s, 1H); 8.91 (s, 1H). |
| 53 | [348] | 4.49 (m, 2H); 5.35 (m, 1H); 6.49 (d, 1H); 7.01 (d, 1H); 7.45 (m, 1H); 7.55 (m, 1H); 7.72 (m, 2H); 8.05 (d, 1H); 8.15 (d, 1H); 8.76 (s, 1H); 8.96 (s, 1H). |
| 54 | [347] | 4.49 (m, 2H); 5.31 (m, 1H); 6.47 (d, 1H); 6.94 (d, 1H); 7.35 (m, 2H); 7.64 (m, 2H); 7.84 (m, 2H); 8 (d, 1H); 8.5 (s, 1H); 8.9 (s, 1H) |
| 55 | [352] | 4.7 (m, 2H); 5.6 (m, 1H); 7.45 (s, 1H); 7.7 (m, 2H); 7.85 (s, 1H); 8.3 (m, 4H); 8.6 (s, 1H); 8.95 (s, 1H). |
| 56 | [313] | 4.7 (m, 2H); 5.6 (m, 1H); 7.41 (s, 1H); 7.6 (m, 4H); 7.8 (s, 1H); 7.91 (s, 1H); 8.2 (s, 1H); 8.9 (s, 1H). |
| 57 | [353] | 2.51 (s, 3H); 4.7 (m, 2H); 5.58 (m, 1H); 7.31 (m, 2H); 7.42 (s, 1H); 7.6 (m, 2H); 7.8 (s, 1H); 7.91 (m, 2H); 8.31 (s, 1H); 8.88 (s, 1H). |
| 58 | [347] | 4.68 (m, 2H); 5.59 (m, 1H); 7.16 (m, 1H); 7.4 (m, 2H); 7.62 (m, 2H); 7.81 (s, 1H); 8.27 (s, 1H); 8.9 (s, 1H). |
| 59 | [385] | 3.25 (s, 3H); 4.7 (m, 2H); 5.6 (m, 1H); 7.45 s, 1H); 7.68 (m, 2H); 7.35 (s, 1H); 7.98 (d, 2H); 8.23 (d, 2H); 8.53 (s, 1H); 8.94 (s, 1H). |
| 60 | [363] | 4.7 (m, 2H); 5.58 (m, 1H); 7.35 (m, 2H); 7.43 (s, 1H); 7.65 (m, 2H); 7.85 (m, 2H); 7.9 (s, 1H); 7.98 (d, 1H); 8.4 (s, 1H); 8.95 (s, 1H). |
| 61 | [363] | 4.7 (m, 2H); 5.58 (m, 1H); 7.43 (s, 1H); 7.52 (d, 1H); 7.63 (m, 2H); 7.8 (m, 2H); 7.98 (m, 1H); 8.06 (m, 1H); 8.4 (s, 1H); 8.95 (s, 1H); 8.92 (s, 1H). |
| 62 | [322] | 2.72 (s, 3H); 4.85 (d, 2H); 6.15 (t, 1H); 7.35 (t, 1H); 7.48 (t, 2H); 7.65 (d, 1H); 7.84 (m, 3H); 8.15 (s, 1H); 8.75 (s, 1H) |
| 63 | [328] | 2.73 (s, 3H); 4.85 (d, 2H); 6.18 (t, 1H); 7.17 (d, 1H); 7.48 (d, 1H); 7.55 (d, 1H); 7.63 (m, 1H); 7.82 (d, 1H); 8.15 (s, 1H); 8.73 (s, 1H) |
| 64 | [352] | 2.70 (s, 3H); 3.82 (s, 3H); 4.82 (d, 2H); 6.16 (m, 1H); 7.05 (d, 2H); 7.63 (d, 1H); 7.75 (m, 2H); 7.82 (d, 1H); 8.15 (s, 1H); 8.75 (s, 1H) |
| 65 | [377] | 1.98 (t, 4H); 3.28 (t, 4H); 4.82 (d, 2H); 6.18 (t, 1H); 6.60 (d, 2H); 7.56 (d, 1H); 7.75 (m, 3H); 8.05 (s, 1H); 8.25 (s, 1H); 9.03 (s, 1H) |
| 66 | [326] | 4.82 (s, 2H); 6.19 (m, 1H); 7.31 (m, 2H); 7.38 (m, 1H); 7.67 (d, 1H); 7.84 (d, 1H); 8.08 (s, 1H); 8.38 (t, 1H); 8.45 (d, 1H); 9.22 (s, 1H) |
| 67 | [386] | 3.25 (s, 3H); 4.85 (s, 2H); 6.18 (m, 1H); 7.71 (d, 1H); 7.87 (d, 1H); 8.00 (d, 2H); 8.14 (s, 1H); 8.22 (d, 2H); 8.67 (s, 1H); 9.14 (s, 1H) |
| 68 | [348] | 4.83 (s, 2H); 6.19 (m, 1H); 7.28 (m, 2H); 7.35 (m, 1H); 7.67 (m, 3H); 7.79 (d, 1H); 8.12 (s, 1H) 8.53 (s, 1H); 9.20 (s, 1H) |
| 69 | [364] | 4.83 (s, 2H); 6.19 (m, 1H); 7.35 (m, 2H); 7.68 (d, 1H); 7.85 (m, 3H); 7.98 (d, 1H); 8.12 (s, 1H) 8.55 (s, 1H); 9.15 (s, 1H) |
| 70 | [298] | 4.82 (s, 2H); 6.18 (m, 1H); 6.60 (d, 1H); 6.82 (d, 1H); 7.60 (d, 1H); 7.74 (s, 1H); 7.82 (d, 1H); 8.08 (s, 1H); 8.38 (s, 1H); 9.14 (s, 1H) |
| 71 | [364] | 4.83 (s, 2H); 6.18 (m, 1H); 7.55 (d, 1H); 7.67 (d, 1H); 7.82 (m, 2H); 7.96 (d, 1H); 8.08 (d, 1H); 8.12 (s, 1H); 8.50 (s, 1H); 8.55 (s, 1H); 9.15 (s, 1H) |
| 72 | [376] | 2 (m, 4H); 3.32 (m, 4H); 4.68 (d, 2H); 5.58 (t, 1H); 6.6 (d, 2H); 7.41 (s, 1H); 7.55 (m, 2H); 7.75 (m, 3H); 8.11 (s, 1H); 8.82 (s, 1H). |
| 73 | 181.5-182 | 1.5 (d, 3H); from 4.95 to 5.05 (m, 1H); 5.65 (d, 1H); 7.45 (s, 1H); 7.55 (d, 2H); from 7.6 to 7.7 (m, 2H); 7.8 (s, 1H); 8.05 (d, 2H); 8.4 (s, 1H); 8.95 (s, 1H). |

TABLE 3-continued

| Ex | Mp or [M + H] | ¹H NMR spectrum (DMSO-d6, δ in ppm) |
|---|---|---|
| 74 | 206-210 | 1.6 (s, 6H); 5.5 (s, 1H); 7.4 (s, 1H); 7.5 (d, 2H); from 7.6 to 7.7 (m, 2H); 7.75 (s, 1H); 8.0 (d, 2H); 8.35 (s, 1H); 8.9 (s, 1H). |
| 75 | [335] | 2.68 (s, 3H); 3.81 (s, 3H); 4.49 (d, 2H); 5.32 (t, 1H); 6.45 (d, 1H); 6.98 (d, 1H); 7.06 (d, 2H); 7.61 (m, 2H); 7.75 (m, 2H); 8.48 (s, 1H). |
| 76 | [358] | 4.5 (d, 2H); 5.32 (t, 1H); 6.45 (d, 1H); 6.95 (d, 1H); 7.66 (m, 2H); 7.81 (m, 2H); 8.18 (m, 1H); 8.6 (s, 1H); 8.87 (s, 1H). |
| 77 | [321] | 3.8 (s, 3H); 4.48 (d, 2H); 5.31 (t, 1H); 6.42 (d, 1H); 6.9 (d, 1H); 7.02 (d, 2H); 7.6 (m, 2H); 7.89 (d, 2H); 8.32 (s, 1H); 8.81 (s, 1H). |
| 78 | [308] | 4.48 (d, 2H); 5.31 (t, 1H); 6.42 (d, 1H); 6.92 (d, 1H); 7.3 (m, 2H); 7.61 (m, 2H); 7.99 (m, 2H); 8.41 (s, 1H); 8.82 (s, 1H). |
| 79 | [327] | 4.48 (m, 2H); 5.31 (m, 1H); 6.43 (d, 1H); 6.93 (d, 1H); 7.51 (m, 1H); 7.65 (m, 2H); 7.8 (m, 1H); 7.97 (m, 1H); 8.49 (s, 1H); 8.82 (s, 1H). |
| 80 | [297] | 4.48 (d, 2H); 5.31 (t, 1H); 6.42 (d, 1H); 6.91 (d, 1H); 7.6 (m, 4H); 7.9 (d, 1H); 8.29 (s, 1H); 8.82 (s, 1H). |
| 81 | [331] | 4.48 (m, 2H); 5.31 (m, 1H); 6.42 (d, 1H); 6.92 (d, 1H); 7.16 (d, 1H); 7.4 (d, 1H); 7.6 (m, 2H); 8.33 (s, 1H); 8.82 (s, 1H). |
| 82 | [309] | 4.48 (m, 2H); 5.31 (m, 1H); 6.43 (d, 1H); 6.91 (d, 1H); 7.38 (m, 3H); 7.65 (m, 2H); 8.26 (d, 1H); 8.41 (s, 1H); 8.92 (s, 1H). |
| 83 | [369] | 4.48 (m, 2H); 5.31 (m, 1H); 6.45 (d, 1H); 6.94 (d, 1H); 7.42 (m, 1H); 7.51 (m, 1H); 7.62 (m, 2H); 7.96 (m, 1H); 8.15 (s, 1H); 8.52 (s, 1H); 8.82 (s, 1H). |
| 84 | [339] | 2.41 (s, 3H); 4.49 (m, 2H); 5.31 (m, 1H); 6.44 (d, 1H); 6.92 (d, 1H); 7.45 (m, 1H); 7.61 (m, 2H); 7.79 (m, 1H); 7.98 (m, 1H); 8.45 (s, 1H); 8.82 (s, 1H). |
| 85 | [369] | 3.25 (s, 3H). 4.49 (m, 2H); 5.31 (m, 1H); 6.44 (d, 1H); 6.95 (d, 1H); 7.69 (m, 2H); 8 (d, 2H); 8.21 (d, 2H); 8.62 (s, 1H); 8.87 (s, 1H). |
| 86 | [297] | 4.48 (m, 2H); 5.31 (m, 1H); 6.44 (d, 1H); 6.91 (d, 1H); 7.12 (m, 1H); 7.51 (m, 2H); 7.6 (m, 2H); 8.32 (s, 1H); 8.81 (s, 1H). |
| 87 | [331] | 4.49 (m, 2H); 5.31 (m, 1H); 6.45 (d, 1H); 6.92 (d, 1H); 7.41 (m, 2H); 7.66 (m, 3H); 8.19 (m, 1H); 8.51 (s, 1H); 8.56 (s, 1H); 8.88 (s, 1H). |
| 88 | [333] | 3.25 (t, 2H); 4.49 (m, 2H); 4.58 (t, 2H); 5.31 (m, 1H); 6.45 (d, 1H); 6.82 (d, 1H); 6.9 (d, 1H); 7.57 (m, 2H); 7.7 (d, 1H); 7.81 (s, 1H); 8.29 (s, 1H); 8.8 (s, 1H). |
| 89 | [281] | 4.49 (d, 2H); 5.31 (t, 1H); 6.45 (d, 1H); 6.6 (m, 1H); 6.83 (d, 1H); 6.91 (d, 1H); 7.61 (m, 2H); 7.76 (s, 1H); 8.25 (s, 1H); 8.88 (s, 1H). |
| 90 | [331] | 4.49 (m, 2H); 5.31 (m, 1H); 6.45 (d, 1H); 6.91 (s, 1H); 7.02 (s, 1H); 7.61 (m, 3H); 7.91 (d, 1H); 8.01 (s, 1H); 8.25 (s, 1H); 8.45 (s, 1H); 8.85 (s, 1H). |
| 91 | [298] | 4.48 (m, 2H); 5.31 (m, 1H); 6.44 (d, 1H); 6.94 (d, 1H); 7.67 (m, 2H); 7.75 (d, 1H); 7.91 (d, 1H); 8.52 (s, 1H); 8.91 (s, 1H). |
| 92 | [337] | 3.32 (s, 3H); 4.48 (m, 2H); 5.31 (m, 1H); 6.44 (d, 1H); 6.91 (d, 1H); 7.32 (d, 2H); 7.6 (m, 2H); 7.8 (m, 2H); 8.41 (s, 1H); 8.81 (s, 1H). |
| 93 | [355] | 2.72 (s, 3H); 4.7 (d, 2H); 5.59 (t, 1H); 7.52 (d, 2H); 7.62 (m, 3H); 7.85 (m, 3H); 8.6 (s, 1H). |
| 94 | [327] | 2.76 (s, 3H); 4.68 (d, 2H); 5.58 (t, 1H); 7.18 (m, 1H); 7.48 (d, 1H); 7.57 (m, 3H); 7.62 (m, 1H); 7.86 (s, 1H); 8.58 (s, 1H). |
| 95 | [355] | 2.72 (s, 3H); 4.68 (d, 2H); 5.58 (t, 1H); 7.41 (m, 1H); 7.51 (m, 1H); 7.65 (m, 3H); 7.79 (d, 1H); 7.86 (m, 2H); 8.61 (s, 1H). |
| 96 | [357] | 3.3 (s, 3H); 4.69 (m, 2H); 5.59 (m, 1H); 7.21 (m, 1H); 7.39 (m, 1H); 7.66 (m, 4H); 7.88 (s, 1H); 8.6 (s, 1H). |
| 97 | [325] | 4.68 (m, 2H); 5.57 (m, 1H); 7.28 (m, 2H); 7.41 (s, 1H); 7.61 (m, 2H); 7.81 (s, 1H); 8 (m, 2H); 8.31 (s, 1H); 8.9 (s, 1H). |
| 98 | [343] | 4.68 (m, 2H); 5.57 (m, 1H); 7.42 (s, 1H); 7.5 (m, 1H); 7.61 (m, 2H); 7.8 (m, 2H); 7.98 (m, 1H); 8.4 (s, 1H); 8.9 (s, 1H). |
| 99 | [332] | 4.7 (m, 2H); 5.58 (m, 1H); 7.48 (s, 1H); 7.66 (m, 3H); 7.79 (d, 1H); 7.85 (s, 1H); 8.32 (d, 1H); 8.41 (s, 1H); 8.5 (s, 1H); 8.92 (s, 1H). |
| 100 | [325] | 4.7 (m, 2H); 5.58 (m, 1H); 7.32 (m, 4H); 7.67 (m, 2H); 7.8 (s, 1H); 8.29 (m, 2H); 9 (s, 1H). |
| 101 | [384] | 4.68 (d, 2H); 5.57 (m, 1H); 7.41 (m, 2H); 7.50 (d, 1H); 7.64 (m, 2H); 7.82 (s, 1H); 7.97 (d, 1H); 8.15 (s, 1H); 8.43 (s, 1H); 8.88 (s, 1H) |
| 102 | [347] | 4.69 (s, 2H); 5.58 (m, 1H); 7.31 (m, 3H); 7.42 (s, 1H); 7.68 (m, 4H); 7.82 (s, 1H); 8.46 (s, 1H); 8.98 (s, 1H) |
| 103 | [313] | 4.68 (d, 2H); 5.57 (m, 1H); 7.13 (m, 1H); 7.41 (s, 1H); 7.57 (m, 4H); 7.80 (s, 1H); 8.22 (s, 1H); 8.88 (s, 1H) |
| 104 | [347] | 4.69 (d, 2H); 5.57 (m, 1H); 7.41 (m, 3H); 7.65 (m, 3H); 7.82 (s, 1H); 8.21(m, 1H); 8.44 (s, 1H); 8.53 (s, 1H); 8.95 (s, 1H) |
| 105 | [361] | 4.33 (s, 3H); 4.69 (s, 2H); 5.58 (m, 1H); 7.26 (m, 2H); 7.43 (s, 1H); 7.65 (dd, 2H); 7.75 (s, 2H); 7.86 (s, 1H); 8.56 (s, 1H); 9.04 (s, 1H) |
| 106 | [349] | 3.25 (t, 2H); 4.55 (t, 2H); 4.68 (s, 2H); 5.57 (m, 1H); 6.81 (d, 1H); 7.42 (s, 1H); 7.57 (m, 2H); 7.71 (d, 1H); 7.78 (s, 1H); 7.83 (s, 1H); 8.20 (s, 1H); 8.86 (s, 1H) |
| 107 | [297] | 4.65 (s, 2H); 5.57 (m, 1H); 6.60 (m, 1H); 6.82 (m, 1H); 7.40 (s, 1H); 7.57 (d, 1H); 7.65 (s, 1H); 7.75 (s, 1H); 7.80 (s, 1H); 8.12 (s, 1H); 8.92 (s, 1H) |
| 108 | [347] | 4.68 (s, 2H); 5.57 (m, 1H); 7.02 (d, 1H); 7.44 (s, 1H); 7.64 (m, 3H); 7.81 (s, 1H); 7.95 (d, 1H); 8.02 (s, 1H); 8.27 (s, 1H); 8.34 (s, 1H); 8.91 (s, 1H) |

TABLE 3-continued

| Ex | Mp or [M + H] | $^1$H NMR spectrum (DMSO-d6, δ in ppm) |
|---|---|---|
| 109 | [314] | 4.68 (s, 2H); 5.58 (m, 1H); 7.40 (s, 1H); 7.68 (dd, 2H); 7.75 (d, 1H); 7.83 (s, 1H); 7.92 (d, 1H); 8.40 (s, 1H); 8.98 (s, 1H) |
| 110 | [356] | 2.70 (s, 3H); 4.82 (s, 2H); 6.18 (m, 1H); 7.54 (d, 1H); 7.65 (d, 1H); 7.85 (m, 3H); 8.17 (s, 1H); 8.75 (s, 1H) |
| 11 | [356] | 2.72 (s, 3H); 4.82 (s, 2H); 6.19 (m, 1H); 7.42 (d, 1H); 7.52 (t, 1H); 7.67 (d, 1H); 7.78 (d, 1H); 7.85 (m, 2H); 8.16 (s, 1H); 8.77 (s, 1H). |
| 112 | [376] | 4.81 (s, 2H); 6.19 (m, 1H); 7.68 (d, 1H); 7.82 (m, 3H); 8.10 (s, 1H); 8.15 (d, 2H); 8.62 (s, 1H); 9.12 (s, 1H) |
| 113 | [326] | 4.81 (s, 2H); 6.19 (m, 1H); 7.29 (t, 2H); 7.65 (d, 1H); 7.81 (d, 1H); 7.99 (m, 2H); 8.10 (s, 1H); 8.47 (s, 1H); 9.11 (s, 1H) |
| 114 | [344] | 4.81 (s, 2H); 6.19 (m, 1H); 7.52 (q, 1H); 7.65 (d, 1H); 7.80 (m, 1H); 7.82 (d, 1H); 7.96 (m, 1H); 8.12 (s, 1H); 8.52 (s, 1H); 9.10 (s, 1H) |
| 115 | [314] | 4.81 (s, 2H); 6.19 (m, 1H); 7.60 (m, 3H); 7.79 (d, 1H); 7.90 (d, 1H); 8.07 (s, 1H); 8.32 (s, 1H); 9.09 (s, 1H) |
| 116 | [309] | 4.82 (s, 2H); 6.20 (m, 1H); 7.32 (m, 1H); 7.67 (d, 1H); 7.83 (d, 1H); 7.87 (t, 1H); 8.10 (m, 2H); 8.59 (m, 2H); 9.20 (s, 1H) |
| 117 | [348] | 4.80 (s, 2H); 6.20 (m, 1H); 7.15 (d, 1H); 7.39 (d, 1H); 7.61 (d, 1H); 7.82 (d, 1H); 8.10 (m, 1H); 8.39 (s, 1H); 9.08 (s, 1H) |
| 118 | [385] | 4.81 (s, 2H); 6.19 (m, 1H); 7.42 (t, 1H); 7.53 (d, 1H); 7.67 (d, 1H); 7.84 (d, 1H); 7.95 (d, 1H); 8.12 (m, 2H); 8.57 (s, 1H); 9.08 (s, 1H) |
| 119 | [356] | 2.4 (s, 3H); 4.82 (s, 2H); 6.20 (m, 1H); 7.48 (d, 1H); 7.63 (d, 1H); 7.80 (m, 2H); 7.95 (m, 1H); 8.10 (s, 1H); 8.47 (s, 1H); 9.08 (s, 1H) |
| 120 | [314] | 4.80 (s, 2H); 6.18 (m, 1H); 7.12 (m, 1H); 7.51 (m, 2H); 7.61 (m, 1H); 7.80 (d, 1H); 8.09 (s, 1H); 8.35 (s, 1H); 9.08 (s, 1H) |
| 121 | [347] | 4.82 (s, 2H); 6.18 (m, 1H); 7.40 (m, 2H); 7.67 (m, 2H); 7.83 (d, 1H); 8.10 (s, 1H); 8.19 (s, 1H); 8.50 (s, 1H); 8.59 (m, 1H); 9.17 (s, 1H) |
| 122 | [350] | 3.23 (t, 2H); 4.57 (t, 2H); 4.81 (s, 2H); 6.17 (m, 1H); 6.82 (d, 1H); 7.60 (d, 1H); 7.70 (d, 1H); 7.75 (d, 1H); 7.82 (s, 1H); 8.07 (s, 1H); 8.33 (s, 1H); 9.07 (s, 1H) |
| 123 | [348] | 4.82 (s, 2H); 6.17 (m, 1H); 7.03 (s, 1H); 7.65 (m, 2H); 7.80 (d, 1H); 7.92 (s, 1H); 8.02 (s, 1H); 8.09 (s, 1H); 8.35 (s, 1H); 8.49 (s, 1H); 9.11 (s, 1H) |
| 124 | [315] | 4.80 (d, 2H); 6.18 (t, 1H); 7.68 (d, 1H); 7.75 (s, 1H); 7.90 (m, 2H); 8.12 (s, 1H); 8.58 (s, 1H); 9.20 (s, 1H) |
| 125 | [321] | 4.48 (s, 2H); 4.56 (s, 2H); 5.25 (m, 1H); 5.31 (m, 1H); 6.44 (d, 1H); 6.92 (d, 1H); 7.28 (d, 1H); 7.40 (t, 1H); 7.60 (m, 2H); 7.81 (d, 1H); 7.95 (s, 1H); 8.45 (s, 1H); 8.85 (s, 1H) |
| 126 | [376] | 1.89 (s, 3H); 4.28 (d, 2H); 4.48 (s, 2H); 5.32 (m, 1H); 6.44 (d, 1H); 6.92 (d, 1H); 7.32 (d, 2H); 7.61 (m, 2H); 7.90 (d, 2H) 8.36 (t, 1H); 8.42 (s, 1H); 8.82 (s, 1H) |
| 127 | [380] | 2.9 (s, 3H); 3 (s, 3H); 4.5 (s, 2H); 5.3 (s, 1H); 6.45 (d, 1H); 6.95 (d, 1H); 7.45 (t, 1H); 7.65 (m, 2H); 7.85 (m, 2H); 8.55 (s, 1H); 8.85 (s, 1H) |
| 128 | 182-185 | 1.55 (s, 6H); 5.5 (s, 1H); 6.45 (s, 1H); 7.4 (m, 2H); 7.6 (m, 4H); 7.7 (s, 1H); 8.05 (s, 1H); 8.3 (s, 1H); 8.9 (s, 1H); 11.15 (s, 1H). |
| 129 | [365] | 2.07 (s, 3H); 4.31 (m, 2H); 6.18 (m, 1H); 7.38 (m, 1H); 7.59 (m, 3H); 7.67 (d, 1H); 7.85 (d, 1H); 8.11 (s, 1H); 8.21 (s, 1H); 8.42 (s, 1H); 9.15 (s, 1H). |
| 130 | [338] | 4.53 (m, 2H); 4.82 (m, 2H); 5.21 (m, 1H); 6.18 (m, 1H); 7.41 (d, 2H); 7.69 (m, 1H); 7.9 (m, 3H); 8.12 (s, 1H); 8.5 (s, 1H); 9.12 (s, 1H). |
| 131 | [338] | 4.59 (d, 2H); 4.83 (m, 2H); 5.28 (t, 1H); 6.19 (t, 1H); 7.29 (d, 1H); 7.4 (m, 1H); 7.65 (d, 1H); 7.8 (m, 2H); 7.94 (s, 1H); 8.1 (s, 1H); 8.48 (s, 1H); 9.1 (s, 1H). |
| 132 | [347] | 4.82 (m, 2H); 6.19 (m, 1H); 6.52 (s, 1H); 7.4 (m, 1H); 7.5 (d, 1H); 7.7 (m, 2H); 7.91 (m, 1H); 8.15 (m, 2H); 8.48 (s, 1H); 9.2 (s, 1H); 11.2 (s, 1H). |
| 133 | [328] | 2.25 (s, 3H); 4.81 (m, 2H); 6.18 (m, 1H); 7.1 (s, 1H); 7.35 (s, 1H); 7.61 (d, 1H); 7.81 (d, 1H); 8.1 (s, 1H); 8.32 (s, 1H); 9.11 (s, 1H). |
| 134 | [347] | 4.85 (m, 2H); 6.2 (m, 1H); 7 (s, 1H); 7.25 (m, 1H); 7.5 (m, 2H); 7.6 (d, 2H); 7.7 (d, 1H); 7.9 (d, 1H); 8.11 (d, 1H); 9.11 (s, 1H); 11.3 (s, 1H). |
| 135 | [327] | 4.83 (d, 2H); 6.2 (t, 1H); 7.5 (m, 1H); 7.7 (d, 1H); 7.9 (d, 1H); 8.11 (m, 1H); 8.21 (d, 1H); 8.52 (d, 1H); 8.7 (m, 1H); 9.25 (s, 1H). |
| 136 | [379] | 3 (broad peak, 6H); 4.81 (d, 2H); 6.18 (t, 1H); 7.49 (m, 2H); 7.65 (d, 1H); 7.83 (d, 1H); 8 (d, 2H); 8.11 (s, 1H); 8.52 (s, 1H); 9.11 (s, 1H). |
| 137 | [347] | 4.83 (d, 2H); 6.18 (t, 1H); 6.43 (s, 1H); 7.4 (m, 1H); 7.6 (m, 3H); 7.85 (m, 1H); 8.02 (s, 1H); 8.11 (s, 1H); 8.48 (s, 1H); 9.15 (s, 1H); 11.3 (s, 1H). |
| 138 | [339] | 4.09 (s, 3H); 4.81 (d, 2H); 6.18 (t, 1H); 7.1 (m, 1H); 7.63 (d, 1H); 7.81 (d, 1H); 8.09 (s, 1H); 8.18 (m, 1H); 8.55 (m, 2H); 9.21 (s, 1H). |
| 139 | [365] | 2.8 (d, 3H); 4.81 (m, 2H); 6.18 (m, 1H); 7.69 (d, 1H); 7.9 (m, 3H); 8.05 (m, 2H); 8.11 (s, 1H); 8.48 (s, 1H); 8.58 (s, 1H); 9.12 (s, 1H). |
| 140 | [328] | 2.48 (s, 3H); 4.81 (d, 2H); 6.18 (t, 1H); 7.18 (m, 1H); 7.62 (d, 1H); 7.82 (m, 2H); 8.09 (s, 1H); 8.3 (s, 1H); 9.18 (s, 1H). |
| 141 | [359] | 3.83 (s, 3H); 4.82 (m, 2H); 6.21 (m, 1H); 6.55 (d, 1H); 7.4 (d, 1H); 7.58 (d, 1H); 7.75 (d, 2H); 8.02 (m, 1H); 8.18 (m, 2H); 8.55 (s, 1H); 9.2 (s, 1H). |

TABLE 3-continued

| Ex | Mp or [M + H] | $^1$H NMR spectrum (DMSO-d6, δ in ppm) |
|---|---|---|
| 142 | [359] | 4.82 (m, 2H); 6.18 (m, 1H); 7.6 (m, 1H); 7.79 (d, 1H); 7.9 (m, 2H); 8.06 (d, 1H); 8.12 (m, 1H); 8.52 (s, 1H); 8.95 (m, 1H); 9.11 (s, 1H); 9.21 (s, 1H); 9.35 (d, 1H). |
| 143 | [365] | 2.08 (s, 3H); 4.82 (m, 2H); 6.18 (m, 1H); 7.29 (m, 1H); 7.55 (d, 1H); 7.68 (d, 2H); 7.85 (d, 2H); 8.11 (s, 1H); 8.42 (s, 1H); 9.11 (s, 1H); 10.1 (s, 1H). |
| 144 | [393] | 3.2 (m, 4H); 3.75 (m, 4H); 4.82 (m, 2H); 6.2 (m, 1H); 7.06 (d, 1H); 7.65 (m, 1H); 7.8 (d, 2H); 7.85 (m, 1H); 8.12 (m, 2H); 8.4 (m, 1H); 9.11 (m, 1H). |
| 145 | [359] | 4.82 (m, 2H); 6.18 (m, 1H); 7.85 (m, 2H); 8.18 (m, 3H); 8.6 (m, 2H); 8.81 (d, 1H); 9.11 (s, 1H); 9.25 (s, 1H); 9.45 (s, 1H). |
| 146 | [393] | 1.12 (d, 6H); 2.62 (m, 1H); 4.82 (d, 2H); 6.18 (t, 1H); 7.35 (m, 1H); 7.61 (m, 3H); 7.81 (d, 1H); 8.09 (s, 1H); 8.26 (s, 1H); 8.42 (s, 1H); 9.12 (s, 1H); 10 (s, 1H). |
| 147 | [415] | 2.68 (broad peak, 6H); 4.82 (m, 2H); 6.18 (m, 1H); 7.69 (m, 3H); 7.85 (d, 1H); 8.11 (s, 1H); 8.26 (d, 1H); 8.32 (s, 1H); 8.68 (s, 1H); 9.12 (m, 1H). |
| 148 | [345] | 4.82 (d, 2H); 6.19 (t, 1H); 7.63 (s, 2H); 7.72 (d, 1H); 7.91 (d, 1H); 8.18 (s, 1H); 8.8 (s, 1H); 9.13 (m, 1H). |
| 149 | [368] | 0.92 (d, 6H); 1.51 (m, 1H); 1.72 (m, 2H); 4.2 (m, 2H); 4.81 (m, 2H); 6.21 (m, 1H); 7.79 (d, 1H); 7.95 (s, 1H); 8.1 (m, 1H); 8.21 (s, 1H); 8.31 (s, 2H); 9.27 (s, 1H). |
| 150 | 185-190 | 1.55 (s, 6H); 6.5 (d, 1H); 7.4 (d, 1H); from 7.55 to 7.8 (m, 6H); 8.0 (s, 1H); 8.8 (s, 1H); 11.4 (s, 1H); 12.8 (s, 1H) |
| 151 | 200-205 | 1.6 (s, 6H); 5.7 (s, 1H); 6.45 (s, 1H); 7.4 (m, 1H); 7.6 (m, 2H); 7.7 (d, 1H); 7.9 (d, 1H); 8.1 (s, 1H); 8.15 (d, 1H); 8.5 (s, 1H); 8.6 (s, 1H); 9.25 (s, 1H); 11.2 (s, 1H). |
| 152 | 228-232 | 1.55 (s, 6H); 5.35 (s, 1H); 6.45 (s, 1H); 7.4 (t, 1H); 7.45 (d, 1H); 7.65 (m, 2H); 7.7 (d, 1H); 8.0 (d, 1H); 8.1 (m, 2H); 8.45 (s, 1H); 8.6 (d, 1H); 9.3 (s, 1H); 11.2 (s, 1H). |
| 153 | 255-259 | 1.5 (s, 6H); 5.35 (s, 1H); 7.25 (t, 1H); 7.4 (t, 1H); 7.45 (d, 1H); 7.6 (d, 1H); 7.75 (d, 1H); 8.05 (m, 2H); 8.5 (d, 1H); 8.55 (s, 1H); 8.65 (d, 1H); 9.4 (s, 1H); 13.15 (s, 1H) |
| 154 | 195-198 | 1.55 (s, 6H); 2.5 (s, 3H); 5.35 (s, 1H); 6.7 (s, 1H); 7.5 (m, 1H); 7.75 (d, 1H); 8.05 (m, 2H); 8.55 (s, 1H); 8.65 (d, 1H); 9.4 (s, 1H). |
| 155 | 263-266 | 3.7 (s, 3H); 4.55 (d, 2H); 5.35 (t, 1H); 6.45 (m, 1H); 7.05 (s, 1H); 7.35 (d, 1H); 7.4 (m, 1H); 7.65 (m, 3H); 8.05 (s, 1H); 8.35 (s, 1H); 8.65 (s, 1H); 11.15 (s, 1H). |
| 156 | 210-210.5 (dec) | 1.55 (s, 6H); 5.2 (s, 1H); 6.35 (d, 1H); 6.9 (d, 1H); 7.55 (d, 2H); 7.65 (m, 2H); 8.0 (d, 2H); 8.5 (s, 1H); 8.85 (s, 1H). |

The compounds according to the invention were the subject of pharmacological tests for determining their modulatory effect on NOT.

Evaluation of the In Vitro Activity on N2A Cells

The activity of the compounds according to the invention was evaluated on a cell line (N2A) endogenously expressing the mouse Nurr1 receptor and stably transfected with the NOT binding response element (NBRE) coupled to the luciferase reporter gene. The $EC_{50}$ values are between 0.1 nM and 10 μM. The tests were carried out according to the procedure described below.

The Neuro-2A cell line comes from a standard commercial source (ATCC). The Neuro-2A clone was obtained from a spontaneous tumour originating from a mouse A albino strain by R. J Klebe et al. This Neuro-2A line is subsequently stably transfected with 8NBRE-luciferase. The N2A-8NBRE cells are cultured to confluence in 75 cm$^2$ culture flasks containing DMEM supplemented with 10% of foetal calf serum, 4.5 g/l of glucose and 0.4 mg/ml of Geneticin. After one week of culture, the cells are recovered with 0.25% trypsin for 30 seconds and then resuspended in DMEM without phenol red, containing 4.5 g/l of glucose, 10% of Hyclone defatted serum, and deposited in white, transparent-bottom, 96-well plates. The cells are deposited at a rate of 60 000 per well in 75 μl for 24 hours before the addition of the products. The products are applied in 25 μl and incubated for a further 24 hours. On the day of the measurement, an equivalent volume (100 μl) of Steadylite is added to each well, followed by a waiting period of 30 minutes in order to obtain complete lysis of the cells and maximum production of the signal. The plates are then measured in a microplate luminescence counter after having been sealed with an adhesive film. The products are prepared in the form of a stock solution at $10^{-2}$ M, and then diluted in 100% of DMSO. Each product concentration is diluted beforehand in culture medium before incubation with the cells thus containing a final concentration of 0.625% of DMSO.

For example, compound Nos 4, 10, 30, 36, 59 and 64 showed an $EC_{50}$ of 4.5; 2; 48; 137; 74 and 102 nM, respectively.

It therefore appears that the compounds according to the invention have a NOT-modulating effect.

The compounds according to the invention can therefore be used for the preparation of medicaments for their therapeutic use in the treatment and prevention of diseases involving NOT receptors.

Thus, according to another of its aspects, a subject of the invention is medicaments which comprise a compound of formula (I), or an addition salt of the latter with a pharmaceutically acceptable acid.

These medicaments are of use in therapeutics, in particular in the treatment and prevention of neurodegenerative diseases such as, for example, Parkinson's disease, Alzheimer's disease, tauopathies (for example, progressive supranuclear paralysis, frontotemporal dementia, corticobasal degeneration, Pick's disease); cerebral traumas such as ischaemia and cranial traumas and epilepsy; psychiatric diseases such as schizophrenia, depression, substance dependence, attention deficit hyperactivity disorders; inflammatory diseases of the central nervous system, such as multiple sclerosis, encephalitis, myelitis and encephalomyelitis and other inflammatory diseases such as vascular pathologies, atherosclerosis, joint inflammations, arthritis, rheumatoid arthritis, osteoarthritis, Crohn's disease, ulcerative colitis; allergic inflammatory diseases such as asthma, autoimmune diseases such as type 1 diabetes, lupus, scleroderma, Guillain-Barré syndrome, Addison's disease and other immunomediated diseases; osteoporosis; cancers.

These compounds could also be used as a treatment combined with stem cell transplantations and/or grafts.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, intratracheal, intranasal, transdermal or rectal administration, the active ingredient of formula (I) above, or salt thereof, may be administered in unit administration form, as a mixture with conventional pharmaceutical excipients, to animals and to humans for the prophylaxis or the treatment of the disorders or diseases above.

The suitable unit administration forms comprise oral administration forms such as tablets, soft or hard capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating the pathologies indicated above, which comprises the administration, to a patient, of an effective dose of a compound according to the invention, or a pharmaceutically acceptable salt thereof.

What is claimed is:

1. A method for modulating NOT receptors comprising administering to a patient in need thereof an effective amount of a compound of formula (I):

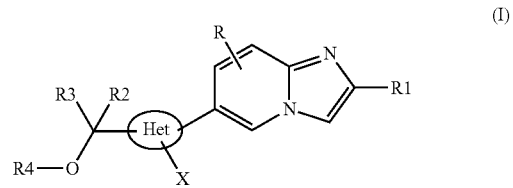

wherein:

$R_1$ represents:
a phenyl or naphthyl group, a heteroaryl group or a heterocyclic group, wherein these groups are optionally substituted with one or more atoms or groups chosen, independently of one another, from the following atoms or groups: halogen, $(C_1-C_{10})$alkyl, halo$(C_1-C_{10})$alkyl, $(C_1-C_{10})$alkoxy, halo$(C_1-C_{10})$alkoxy, $(C_1-C_{10})$thioalkyl, —S(O)$(C_1-C_{10})$alkyl, —S(O)$_2$$(C_1-C_{10})$-alkyl), hydroxyl, oxo, cyano, nitro, hydroxy$(C_1-C_{10})$alkylene, NRaRb$(C_1-C_{10})$alkylene, $(C_1-C_{10})$alkoxy$(C_1-C_{10})$alkyleneoxy, NRaRb, CONRaRb, SO$_2$NRaRb, NRcCORd, OC(O)NRaRb, OCO$(C_1-C_{10})$alkyl, NRcC(O)ORe, NRcSO$_2$Re, aryl $(C_1-C_{10})$alkylene, monocyclic heteroaryl and aryl, wherein the monocyclic heteroaryl or aryl are optionally substituted with one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, oxo, nitro, cyano or OCO$(C_1-C_{10})$alkyl group, and $R_1$ is linked to the imidazo[1,2-a]pyridine by an aromatic carbon;

Het represents a monocyclic heteroaryl group containing from 5 to 6 atoms, including from 1 to 3 heteroatoms chosen from N, O and S;

X represents from 1 to 3 substituents, which are identical to or different from one another, chosen from a hydrogen, a halogen, $(C_1-C_{10})$alkyl, $(C_1-C_{10})$alkoxy, NRaRb, nitro and cyano, wherein the $(C_1-C_{10})$alkyl is optionally substituted with one or more groups chosen from a halogen, $(C_1-C_{10})$alkoxy, $(C_1-C_{10})$haloalkoxy, NRaRb and hydroxyl;

R represents, at position 3, 5, 7 or 8 of the imidazo[1,2-a] pyridine, from 1 to 4 substituents, which are identical to or different from one another, chosen from a hydrogen, a halogen, $(C_1-C_{10})$alkyl, halo$(C_1-C_{10})$alkyl and $(C_1-C_{10})$alkoxy;

$R_2$ and $R_3$ represent, independently of one another,
a hydrogen atom,
a $(C_1-C_{10})$alkyl group, optionally substituted with an Rf group; or
an aryl group, optionally substituted with one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;

$R_4$ represents:
a hydrogen atom,
a $(C_1-C_{10})$alkyl group, optionally substituted with an Rf group; or
an aryl group, optionally substituted with one or more substituents chosen from a halogen and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano, $(C_1-C_{10})$alkyl(CO)—, CONRaRb, NRcCORd, OC(O)NRaRb, OCO$(C_1-C_{10})$alkyl, NRcC(O)ORe or aryl group, wherein the aryl is optionally substituted with one or more substituents chosen from a halogen and a ($C_1$-$C_{10}$)alkyl, halo($C_1$-$C_{10}$)alkyl, ($C_1$-$C_{10}$)alkoxy, halo($C_1$-$C_{10}$)alkoxy, NRaRb, hydroxyl, nitro or cyano group;

Ra and Rb represent, independently of one another, a hydrogen atom or a ($C_1$-$C_{10}$)alkyl, aryl($C_1$-$C_{10}$)alkylene or aryl group;

or Ra and Rb form, together with the nitrogen atom which bears them, an azetidine, pyrrolidine, piperidine, azepine, morpholine, thiomorpholine, piperazine or homopiperazine group, this group being optionally substituted with a ($C_1$-$C_{10}$)alkyl, aryl or aryl ($C_1$-$C_{10}$)alkylene group;

Rc and Rd represent, independently of one another, a hydrogen atom or a ($C_1$-$C_{10}$)alkyl, aryl($C_1$-$C_{10}$)alkylene or aryl group;

or Rc and Rd together form a ($C_2$-$C_5$)alkylene group;

Re represents a ($C_1$-$C_{10}$)alkyl, aryl ($C_1$-$C_{10}$)alkylene or aryl group;

or Rc and Re together form a ($C_2$-$C_5$)alkylene group; and

Rf represents a halogen atom or a ($C_1$-$C_{10}$)alkoxy, halo($C_1$-$C_{10}$)alkoxy, hydroxyl, cyano, NRaRb, C(O)NRaRb, NRcCORd, OC(O)NRaRb, OCO($C_1$-$C_{10}$)alkyl, NRc-COORe, SO$_2$NRaRb, NRcSO$_2$Re, aryl($C_1$-$C_{10}$)alkylene or aryl group, wherein the aryl is optionally substituted with one or more substituents chosen from a halogen and a ($C_1$-$C_{10}$)alkyl, halo($C_1$-$C_{10}$)alkyl, ($C_1$-$C_{10}$)alkoxy, halo($C_1$-$C_{10}$)alkoxy, NRaRb, hydroxyl, nitro, cyano or OCO($C_1$-$C_{10}$)alkyl group;

or a pharmaceutically acceptable salt thereof.

2. The method according to claim 1, wherein, for the compound of formula (I) or pharmaceutically acceptable salt thereof:

$R_1$ represents a phenyl, furyl, quinolinyl, indolyl, pyrrolopyridinyl, pyridinyl, isoquinolinyl, thienyl, benzofuranyl, benzothiazolyl, benzothienyl, dihydrobenzofuranyl, thiazolyl, pyrazolyl, isoxazolyl, benzimidazolyl or indazolyl group, wherein these groups are optionally substituted with one or more groups or atoms chosen, independently of one another, from halogen, ($C_1$-$C_{10}$) alkyl, ($C_1$-$C_{10}$)alkoxy, CONRaRb, NRaRb, ($C_1$-$C_{10}$) thioalkyl, —S(O)$_2$($C_1$-$C_{10}$-alkyl), halo($C_1$-$C_{10}$)alkyl, hydroxy($C_1$-$C_{10}$)alkylene, NRaRb($C_1$-$C_{10}$)alkylene, NRcCORd, SO$_2$NRaRb, cyano and nitro;

Ra and Rb represent, independently of one another, a hydrogen atom or a ($C_1$-$C_{10}$)alkyl group; and Rc and Rd represent, independently of one another, a hydrogen atom or a ($C_1$-$C_{10}$)alkyl group.

3. The method according to claim 1, wherein, for the compound of formula (I) or pharmaceutically acceptable salt thereof:

X represents from 1 to 3 substituents, which are identical to or different from one another, chosen from a hydrogen, a halogen and ($C_1$-$C_{10}$)alkyl groups.

4. The method according to claim 1, wherein, for the compound of formula (I) or pharmaceutically acceptable salt thereof:

R represents, at position 3, 5, 7 or 8 of the imidazo[1,2-a] pyridine, from 1 to 4 substituents, which are identical to or different from one another, chosen from hydrogen and ($C_1$-$C_{10}$)alkyl.

5. The method according to claim 1, wherein, for the compound of formula (I) or pharmaceutically acceptable salt thereof:

$R_2$ and $R_3$ represent, independently of one another, a hydrogen atom or a ($C_1$-$C_{10}$)alkyl group.

6. The method according to claim 1, wherein, for the compound of formula (I) or pharmaceutically acceptable salt thereof:

$R_4$ represents a hydrogen atom or a ($C_1$-$C_{10}$)alkyl group.

7. The method according to claim 1, wherein, for the compound of formula (I) or pharmaceutically acceptable salt thereof:

R represents, at position 3 of the imidazo[1,2-a]pyridine, 1 hydrogen atom or 1 methyl group.

8. The method according to claim 1, wherein, for the compound of formula (I) or pharmaceutically acceptable salt thereof:

$R_1$ represents a phenyl, furyl or quinolinyl group, wherein these groups are optionally substituted with one or more atoms or groups chosen, independently of one another, from halogen and ($C_1$-$C_{10}$)alkyl;

Het represents a furyl group, a thienyl group, a pyridinyl group or a thiazolyl group;

X represents a hydrogen;

R is a hydrogen;

$R_2$ and $R_3$ represent, independently of one another, a hydrogen atom; and $R_4$ represents a hydrogen atom.

9. The method according to claim 1, wherein, for compound of formula (I) is selected from the group consisting of:

{5-[2-(4-Chlorophenyl)imidazo[1,2-a]pyridin-6-yl]furan-2-yl}methanol;

{4-[2-(4-Chlorophenyl)imidazo[1,2-a]pyridin-6-yl]thien-2-yl}methanol;

{5-[2-(4-Chlorophenyl)imidazo[1,2-a]pyridin-6-yl]thien-2-yl}methanol;

{2-[2-(4-Chlorophenyl)imidazo[1,2-a]pyridin-6-yl]pyridin-4-yl}methanol;

{5-[2-(4-Chlorophenyl)imidazo[1,2-a]pyridin-6-yl]pyridin-3-yl}methanol;

{4-[2-(4-Chlorophenyl)imidazo[1,2-a]pyridin-6-yl]furan-2-yl}methanol;

{6-[2-(4-Chlorophenyl)imidazo[1,2-a]pyridin-6-yl]pyridin-2-yl}methanol;

{5-[2-(4-Chlorophenyl)imidazo[1,2-a]pyridin-6-yl]thien-3-yl}methanol;

{2-[2-(4-Chlorophenyl)imidazo[1,2-a]pyridin-6-yl]thiazol-5-yl}methanol;

{2-[2-(4-Chlorophenyl)imidazo[1,2-a]pyridin-6-yl]thiazol-4-yl}methanol;

{4-[2-(4-Chlorophenyl)imidazo[1,2-a]pyridin-6-yl]thiazol-2-yl}methanol;

[2-(2-Furan-3-ylimidazo[1,2-a]pyridin-6-yl)pyridin-4-yl] methanol and the hydrochloride thereof;

[5-(2-Quinolin-3-ylimidazo[1,2-a]pyridin-6-yl)furan-2-yl]methanol and the hydrochloride thereof;

[4-(2-p-Tolylimidazo[1,2-a]pyridin-6-yl)thien-2-yl] methanol;

[2-(2-Quinolin-3-ylimidazo[1,2-a]pyridin-6-yl)pyridin-4-yl]methanol and the hydrochloride thereof;

[4-(2-Quinolin-3-ylimidazo[1,2-a]pyridin-6-yl)thien-2-yl]methanol and the hydrochloride thereof;

{4-[2-(1H-Indol-5-yl)imidazo[1,2-a]pyridin-6-yl]thien-2-yl}methanol;

{5-[2-(1H-Indol-5-yl)imidazo[1,2-a]pyridin-6-yl]furan-2-yl}methanol and the hydrochloride thereof;

[4-(2-Phenylimidazo[1,2-a]pyridin-6-yl)thien-2-yl] methanol and the hydrochloride thereof;

{4-[2-(1H-Pyrrolo[2,3-b]pyridin-5-yl)imidazo[1,2-a]pyridin-6-yl]thien-2-yl}methanol and the hydrochloride thereof;

{4-[2-(3-Methoxyphenyl)imidazo[1,2-a]pyridin-6-yl]thien-2-yl}methanol and the hydrochloride thereof;
{2-[2-(1H-Pyrrolo[2,3-b]pyridin-5-yl)imidazo[1,2-a]pyridin-6-yl]pyridin-4-yl}methanol and the hydrochloride thereof;
[2-(2-Phenylimidazo[1,2-a]pyridin-6-yl)pyridin-4-yl]methanol;
[5-(2-p-Tolylimidazo[1,2-a]pyridin-6-yl)furan-2-yl]methanol;
[5-(2-Phenylimidazo[1,2-a]pyridin-6-yl)furan-2-yl]methanol;
{5-[2-(3-Methoxyphenyl)imidazo[1,2-a]pyridin-6-yl]furan-2-yl}methanol;
{5-[2-(2,4-Difluorophenyl)imidazo[1,2-a]pyridin-6-yl]furan-2-yl}methanol;
{5-[2-(4-Chlorophenyl)imidazo[1,2-a]pyridin-6-yl]furan-3-yl}methanol;
2-(4-Chlorophenyl)-6-(4-methoxymethyl-furan-2-yl)imidazo[1,2-a]pyridine;
{5-[2-(4-Hydroxymethylphenyl)imidazo[1,2-a]pyridin-6-yl]furan-2-yl}methanol;
4-[6-(5-Hydroxymethylfuran-2-yl)imidazo[1,2-a]pyridin-2-yl]-N,N-dimethylbenzamide;
{5-[2-(1H-Indol-6-yl)imidazo[1,2-a]pyridin-6-yl]furan-2-yl}methanol;
{5-[2-(2-Methoxypyridin-3-yl)imidazo[1,2-a]pyridin-6-yl]furan-2-yl}methanol;
[5-(2-Quinolin-5-ylimidazo[1,2-a]pyridin-6-yl)furan-2-yl]methanol;
{5-[2-(4-Morpholin-4-ylphenyl)imidazo[1,2-a]pyridin-6-yl]furan-2-yl}methanol;
[5-(2-Isoquinolin-5-ylimidazo[1,2-a]pyridin-6-yl)furan-2-yl]methanol;
(5-{2-[4-(1-Pyrrolidin-1-ylethyl)phenyl]imidazo[1,2-a]pyridin-6-yl}furan-2-yl)methanol;
4-[6-(5-Hydroxymethylthien-3-yl)imidazo[1,2-a]pyridin-2-yl]-N,N-dimethylbenzamide;
{4-[2-(2-Methoxypyridin-3-yl)imidazo[1,2-a]pyridin-6-yl]thien-2-yl}methanol;
[4-(2-Isoquinolin-5-ylimidazo[1,2-a]pyridin-6-yl)thien-2-yl]methanol;
N-{3-[6-(5-Hydroxymethylthien-3-yl)imidazo[1,2-a]pyridin-2-yl]phenyl}isobutyramide;
(4-{2-[4-(1-Pyrrolidin-1-ylethyl)phenyl]imidazo[1,2-a]pyridin-6-yl}thien-2-yl)methanol;
{4-[2-(4-Dimethylaminomethylphenyl)imidazo[1,2-a]pyridin-6-yl]thien-2-yl}methanol;
2-Fluoro-4-[6-(5-hydroxymethylthien-3-yl)imidazo[1,2-a]pyridin-2-yl]-N,N-dimethylbenzamide;
{4-[2-(3-Aminophenyl)imidazo[1,2-a]pyridin-6-yl]thien-2-yl}methanol;
N-tert-Butyl-5-[6-(5-hydroxymethylthien-3-yl)imidazo[1,2-a]pyridin-2-yl]nicotinamide;
[5-(3-Methyl-2-phenylimidazo[1,2-a]pyridin-6-yl)furan-2-yl]methanol;
[5-(3-Methyl-2-thien-2-ylimidazo[1,2-a]pyridin-6-yl)furan-2-yl]methanol;
{5-[2-(3-Chlorophenyl)-3-methylimidazo[1,2-a]pyridin-6-yl]furan-2-yl}methanol;
{5-[2-(4-Pyrrolidin-1-ylphenyl)imidazo[1,2-a]pyridin-6-yl]furan-2-yl}methanol;
3-[6-(5-Hydroxymethylfuran-2-yl)imidazo[1,2-a]pyridin-2-yl]benzonitrile;
[5-(2-Benzofuran-2-ylimidazo[1,2-a]pyridin-6-yl)furan-2-yl]methanol;
[5-(2-Benzothiazol-2-ylimidazo[1,2-a]pyridin-6-yl)furan-2-yl]methanol;
[5-(2-Benzo[b]thien-2-ylimidazo[1,2-a]pyridin-6-yl)furan-2-yl]methanol;
{4-[2-(4-Nitrophenyl)imidazo[1,2-a]pyridin-6-yl]thien-2-yl}methanol;
[4-(2-Thien-3-ylimidazo[1,2-a]pyridin-6-yl)thien-2-yl]methanol;
{4-[2-(4-Methylthiophenyl)imidazo[1,2-a]pyridin-6-yl]thien-2-yl}methanol;
{4-[2-(5-Chlorothien-2-yl)imidazo[1,2-a]pyridin-6-yl]thien-2-yl}methanol;
{4-[2-(4-Methylsulphonylphenyl)imidazo[1,2-a]pyridin-6-yl]thien-2-yl}methanol;
[4-(2-Benzo[b]thien-2-ylimidazo[1,2-a]pyridin-6-yl)thien-2-yl]methanol;
[4-(2-Benzo[b]thien-5-ylimidazo[1,2-a]pyridin-6-yl)thien-2-yl]methanol;
[4-(3-Methyl-2-phenylimidazo[1,2-a]pyridin-6-yl)thiazol-2-yl]methanol;
[4-(3-Methyl-2-thien-2-ylimidazo[1,2-a]pyridin-6-yl)thiazol-2-yl]methanol;
{4-[2-(4-Methoxyphenyl)-3-methylimidazo[1,2-a]pyridin-6-yl]thiazol-2-yl}methanol;
{4-[2-(4-Pyrrolidin-1-ylphenyl)imidazo[1,2-a]pyridin-6-yl]thiazol-2-yl}methanol;
{4-[2-(2-Fluorophenyl)imidazo[1,2-a]pyridin-6-yl]thiazol-2-yl}methanol;
{4-[2-(4-Methylsulphonylphenyl)imidazo[1,2-a]pyridin-6-yl]thiazol-2-yl}methanol;
[4-(2-Benzofuran-2-ylimidazo[1,2-a]pyridin-6-yl)thiazol-2-yl]methanol;
[4-(2-Benzo[b]thien-2-ylimidazo[1,2-a]pyridin-6-yl)thiazol-2-yl]methanol;
[4-(2-Furan-2-ylimidazo[1,2-a]pyridin-6-yl)thiazol-2-yl]methanol;
[4-(2-Benzo[b]thien-5-ylimidazo[1,2-a]pyridin-6-yl)thiazol-2-yl]methanol;
{4-[2-(4-Pyrrolidin-1-ylphenyl)imidazo[1,2-a]pyridin-6-yl]thien-2-yl}methanol;
1-{4-[2-(4-Chlorophenyl)imidazo[1,2-a]pyridin-6-yl]thien-2-yl}ethanol;
2-{4-[2-(4-Chlorophenyl)imidazo[1,2-a]pyridin-6-yl]thien-2-yl}propan-2-ol;
{5-[2-(4-Methoxyphenyl)-3-methylimidazo[1,2-a]pyridin-6-yl]furan-2-yl}methanol;
{5-[2-(4-Trifluoromethylphenyl)imidazo[1,2-a]pyridin-6-yl]furan-2-yl-methanol;
{5-[2-(4-Methoxyphenyl)imidazo[1,2-a]pyridin-6-yl]furan-2-yl}methanol;
{5-[2-(4-Fluorophenyl)imidazo[1,2-a]pyridin-6-yl]furan-2-yl}methanol;
{5-[2-(3,4-Difluorophenyl)imidazo[1,2-a]pyridin-6-yl]furan-2-yl}methanol;
[5-(2-Thien-3-ylimidazo[1,2-a]pyridin-6-yl)furan-2-yl]methanol;
{5-[2-(5-Chlorothien-2-yl)imidazo[1,2-a]pyridin-6-yl]furan-2-yl}methanol;
{5-[2-(2-Fluorophenyl)imidazo[1,2-a]pyridin-6-yl]furan-2-yl}methanol;
{5-[2-(3-Bromophenyl)imidazo[1,2-a]pyridin-6-yl]furan-2-yl}methanol;
{5-[2-(4-Chloro-3-methylphenyl)imidazo[1,2-a]pyridin-6-yl]furan-2-yl}methanol;
{5-[2-(4-Methylsulphonylphenyl)imidazo[1,2-a]pyridin-6-yl]furan-2-yl}methanol;
[5-(2-Thien-2-ylimidazo[1,2-a]pyridin-6-yl)furan-2-yl]methanol;

[5-(2-Benzofuran-3-ylimidazo[1,2-a]pyridin-6-yl)furan-2-yl]methanol;
{5-[2-(2,3-Dihydrobenzofuran-5-yl)imidazo[1,2-a]pyridin-6-yl]furan-2-yl}methanol;
[5-(2-Furan-2-ylimidazo[1,2-a]pyridin-6-yl)furan-2-yl]methanol;
[5-(2-Benzofuran-5-ylimidazo[1,2-a]pyridin-6-yl)furan-2-yl]methanol;
[5-(2-Thiazol-2-ylimidazo[1,2-a]pyridin-6-yl)furan-2-yl]methanol;
{5-[2-(4-Methylthiophenyl)imidazo[1,2-a]pyridin-6-yl]furan-2-yl}methanol;
{4-[2-(4-Chlorophenyl)-3-methylimidazo[1,2-a]pyridin-6-yl]thien-2-yl}methanol;
[4-(3-Methyl-2-thien-2-ylimidazo[1,2-a]pyridin-6-yl)thien-2-yl]methanol;
{4-[2-(3-Chlorophenyl)-3-methylimidazo[1,2-a]pyridin-6-yl]thien-2-yl}methanol;
{4-[2-(2,4-Difluorophenyl)-3-methylimidazo[1,2-a]pyridin-6-yl]thien-2-yl}methanol;
{4-[2-(4-Fluorophenyl)imidazo[1,2-a]pyridin-6-yl]thien-2-yl}methanol;
{4-[2-(3,4-Difluorophenyl)imidazo[1,2-a]pyridin-6-yl]thien-2-yl}methanol;
3-[6-(5-Hydroxymethylthien-3-yl)imidazo[1,2-a]pyridin-2-yl]benzonitrile;
{4-[2-(2-Fluorophenyl)imidazo[1,2-a]pyridin-6-yl]thien-2-yl}methanol;
{4-[2-(3-Bromophenyl)imidazo[1,2-a]pyridin-6-yl]thien-2-yl}methanol;
[4-(2-Benzofuran-2-ylimidazo[1,2-a]pyridin-6-yl)thien-2-yl]methanol;
[4-(2-Thien-2-ylimidazo[1,2-a]pyridin-6-yl)thien-2-yl]methanol;
[4-(2-Benzofuran-3-ylimidazo[1,2-a]pyridin-6-yl)thien-2-yl]methanol;
{4-[2-(1-Methyl-1H-benzimidazol-2-yl)imidazo[1,2-a]pyridin-6-yl]thien-2-yl}methanol;
{4-[2-(2,3-Dihydrobenzofuran-5-yl)imidazo[1,2-a]pyridin-6-yl]thien-2-yl}methanol;
[4-(2-Furan-2-ylimidazo[1,2-a]pyridin-6-yl)thien-2-yl]methanol;
[4-(2-Benzofuran-5-ylimidazo[1,2-a]pyridin-6-yl)thien-2-yl]methanol;
[4-(2-Thiazol-2-ylimidazo[1,2-a]pyridin-6-yl)thien-2-yl]methanol;
{4-[2-(4-Chlorophenyl)-3-methylimidazo[1,2-a]pyridin-6-yl]thiazol-2-yl}methanol;
{4-[2-(3-Chlorophenyl)-3-methylimidazo[1,2-a]pyridin-6-yl]thiazol-2-yl}methanol;
{4-[2-(4-Trifluoromethylphenyl)imidazo[1,2-a]pyridin-6-yl]thiazol-2-yl}methanol;
{4-[2-(4-Fluorophenyl)imidazo[1,2-a]pyridin-6-yl]thiazol-2-yl}methanol;
{4-[2-(3,4-Difluorophenyl)imidazo[1,2-a]pyridin-6-yl]thiazol-2-yl}methanol;
[4-(2-Thien-3-ylimidazo[1,2-a]pyridin-6-yl)thiazol-2-yl]methanol;
[4-(2-Pyridin-2-ylimidazo[1,2-a]pyridin-6-yl)thiazol-2-yl]methanol;
{4-[2-(5-Chlorothien-2-yl)imidazo[1,2-a]pyridin-6-yl]thiazol-2-yl}methanol;
{4-[2-(3-Bromophenyl)imidazo[1,2-a]pyridin-6-yl]thiazol-2-yl}methanol;
{4-[2-(4-Chloro-3-methylphenyl)imidazo[1,2-a]pyridin-6-yl]thiazol-2-yl}methanol;
[4-(2-Thien-2-ylimidazo[1,2-a]pyridin-6-yl)thiazol-2-yl]methanol;
[4-(2-Benzofuran-3-ylimidazo[1,2-a]pyridin-6-yl)thiazol-2-yl]methanol;
{4-[2-(2,3-Dihydrobenzofuran-5-yl)imidazo[1,2-a]pyridin-6-yl]thiazol-2-yl}methanol;
[4-(2-Benzofuran-5-ylimidazo[1,2-a]pyridin-6-yl)thiazol-2-yl]methanol;
[4-(2-Thiazol-2-ylimidazo[1,2-a]pyridin-6-yl)thiazol-2-yl]methanol;
{5-[2-(3-Hydroxymethylphenyl)imidazo[1,2-a]pyridin-6-yl]furan-2-yl}methanol;
N-{3-[6-(5-Hydroxymethylfuran-2-yl)imidazo[1,2-a]pyridin-2-yl]phenyl}isobutyramide;
2-Fluoro-4-[6-(5-hydroxymethylfuran-2-yl)imidazo[1,2-a]pyridin-2-yl]-N,N-dimethylbenzamide;
2-{4-[2-(1H-Indol-6-yl)imidazo[1,2-a]pyridin-6-yl]thien-2-ylpropan-2-ol;
N-{3-[6-(2-Hydroxymethylthiazol-4-yl)imidazo[1,2-a]pyridin-2-yl]phenyl}acetamide;
{4-[2-(4-Hydroxymethylphenyl)imidazo[1,2-a]pyridin-6-yl]thiazol-2-yl}methanol;
{4-[2-(3-Hydroxymethylphenyl)imidazo[1,2-a]pyridin-6-yl]thiazol-2-yl}methanol;
{4-[2-(1H-Indol-5-yl)imidazo[1,2-a]pyridin-6-yl]thiazol-2-yl}methanol;
{4-[2-(4-Methylthien-2-yl)imidazo[1,2-a]pyridin-6-yl]thiazol-2-yl}methanol;
{4-[2-(1H-Indol-4-yl)imidazo[1,2-a]pyridin-6-yl]thiazol-2-yl}methanol;
{4-[2-(2-Fluoropyridin-3-yl)imidazo[1,2-a]pyridin-6-yl]thiazol-2-yl}methanol;
3-[6-(2-Hydroxymethylthiazol-4-yl)imidazo[1,2-a]pyridin-2-yl]-N,N-dimethylbenzamide;
{4-[2-(1H-Indol-6-yl)imidazo[1,2-a]pyridin-6-yl]thiazol-2-yl}methanol;
{4-[2-(2-Methoxypyridin-3-yl)imidazo[1,2-a]pyridin-6-yl]thiazol-2-yl}methanol;
4-[6-(2-Hydroxymethylthiazol-4-yl)imidazo[1,2-a]pyridin-2-yl]-N-methylbenzamide;
{4-[2-(4-Methylthien-3-yl)imidazo[1,2-a]pyridin-6-yl]thiazol-2-yl}methanol;
{4-[2-(1-Methyl-1H-indol-5-yl)imidazo[1,2-a]pyridin-6-yl]thiazol-2-yl}methanol;
[4-(2-Quinolin-5-ylimidazo[1,2-a]pyridin-6-yl)-thiazol-2-yl]methanol;
N-{4-[6-(2-Hydroxymethylthiazol-4-yl)imidazo[1,2-a]pyridin-2-yl]phenyl}acetamide;
{4-[2-(4-Morpholin-4-ylphenyl)imidazo[1,2-a]pyridin-6-yl]thiazol-2-yl}methanol;
[4-(2-Isoquinolin-5-ylimidazo[1,2-a]pyridin-6-yl)thiazol-2-yl]methanol;
N-{3-[6-(2-Hydroxymethyl-thiazol-4-yl)imidazo[1,2-a]pyridin-2-yl]phenyl}isobutyramide;
3-[6-(2-Hydroxymethylthiazol-4-yl)imidazo[1,2-a]pyridin-2-yl]-N,N-dimethylbenzenesulphonamide;
{4-[2-(2,6-Difluoropyridin-4-yl)imidazo[1,2-a]pyridin-6-yl]thiazol-2-yl}methanol;
(4-{2-[1-(3-Methylbutyl)-1H-pyrazol-4-yl]imidazo[1,2-a]pyridin-6-yl}thiazol-2-yl)methanol;
2-{4-[2-(1H-Indol-6-yl)imidazo[1,2-a]pyridin-6-yl]-1H-pyrazol-3-yl}propan-2-ol;
2-{5-Fluoro-2-[2-(1H-indol-6-yl)imidazo[1,2-a]pyridin-6-yl]pyridin-4-yl}propan-2-ol;
2-{2-[2-(1H-Indol-6-yl)imidazo[1,2-a]pyridin-6-yl]pyridin-4-yl}propan-2-ol;

2-{2-[2-(1H-Indazol-3-yl)imidazo[1,2-a]pyridin-6-yl]pyridin-4-yl}propan-2-ol;
2-{2-[2-(5-Methylisoxazol-3-yl)imidazo[1,2-a]pyridin-6-yl]pyridin-4-yl}propan-2-ol;
{5-[2-(1H-Indol-6-yl)imidazo[1,2-a]pyridin-6-yl]-methyl-1H-imidazol-2-yl}methanol; and
2-{5-[2-(4-Chlorophenyl)imidazo[1,2-a]pyridin-6-yl]furan-2-yl}propan-2-ol;
or a pharmaceutically acceptable salt thereof.

* * * * *